(12) United States Patent
McDevitt et al.

(10) Patent No.: US 12,279,762 B2
(45) Date of Patent: *Apr. 22, 2025

(54) METHOD AND APPARATUS FOR SECURING AN OBJECT TO BONE, INCLUDING THE PROVISION AND USE OF A NOVEL SUTURE ASSEMBLY FOR SECURING AN OBJECT TO BONE

(71) Applicant: Linvatec Corporation, Largo, FL (US)

(72) Inventors: Dennis McDevitt, Semora, NC (US); Vincent Novak, Raleigh, NC (US)

(73) Assignee: Linvatec Corporation, Largo, FL (US)

( * ) Notice: Subject to any disclaimer, the term of this patent is extended or adjusted under 35 U.S.C. 154(b) by 292 days.

This patent is subject to a terminal disclaimer.

(21) Appl. No.: 17/144,351

(22) Filed: Jan. 8, 2021

(65) Prior Publication Data

US 2021/0121172 A1   Apr. 29, 2021

Related U.S. Application Data

(60) Continuation of application No. 15/890,868, filed on Feb. 7, 2018, now Pat. No. 10,888,310, which is a
(Continued)

(51) Int. Cl.
*A61B 17/04* (2006.01)
*A61B 17/17* (2006.01)
(Continued)

(52) U.S. Cl.
CPC ...... *A61B 17/0401* (2013.01); *A61B 17/1796* (2013.01); *A61F 2/08* (2013.01); *A61L 17/04* (2013.01); *A61B 2017/0406* (2013.01); *A61B 2017/0409* (2013.01); *A61B 2017/0496* (2013.01); *A61B 2017/06185* (2013.01);
(Continued)

(58) Field of Classification Search
CPC ........ A61B 17/6166; A61B 2017/0496; A61B 2017/0406
See application file for complete search history.

(56) References Cited

U.S. PATENT DOCUMENTS 6,500,184 B1 * 12/2002 Chan .................. A61B 17/0485
606/232
9,307,977 B2 * 4/2016 McDevitt ........... A61B 17/1796
(Continued)

*Primary Examiner* — Alexander J Orkin
(74) *Attorney, Agent, or Firm* — Bond, Schoeneck & King, PLLC; Frederick J. M. Price

(57) ABSTRACT

A suture assembly including a first suture having a generally O-shaped configuration having a first arm, a second arm, a first bridge connecting the first arm to the second arm, and a second bridge connecting the first arm to the second arm. The first bridge opposes the second bridge so that the first suture includes a closed loop. A second suture having a first arm, a second arm and a bridge connecting the first arm to the second arm. The first arm of the second suture is wrapped around the first arm of the first suture in a first direction, and the second arm of the second suture is wrapped around the second arm of the first suture in a second, opposite direction. The suture assembly is capable of assuming (i) a longitudinally-extended, radially-contracted first configuration, and (ii) a longitudinally-contracted, radially-expanded second configuration.

7 Claims, 56 Drawing Sheets

Related U.S. Application Data division of application No. 14/842,183, filed on Sep. 1, 2015, now abandoned, which is a continuation of application No. 13/398,589, filed on Feb. 16, 2012, now Pat. No. 9,119,893, which is a continuation-in-part of application No. 13/093,634, filed on Apr. 25, 2011, now Pat. No. 9,307,977.

(60) Provisional application No. 61/443,342, filed on Feb. 16, 2011, provisional application No. 61/443,325, filed on Feb. 16, 2011, provisional application No. 61/422,859, filed on Dec. 14, 2010, provisional application No. 61/419,334, filed on Dec. 3, 2010, provisional application No. 61/410,027, filed on Nov. 4, 2010.

(51) Int. Cl.
*A61F 2/08* (2006.01)
*A61L 17/04* (2006.01)
*A61B 17/06* (2006.01)

(52) U.S. Cl.
CPC ............... *A61F 2002/0852* (2013.01); *A61F 2002/0882* (2013.01)

(56) References Cited

U.S. PATENT DOCUMENTS

| | | | |
|---|---|---|---|
| 10,888,310 B2* | 1/2021 | McDevitt | A61B 17/1796 |
| 2003/0167071 A1* | 9/2003 | Martin | A61B 17/0487 606/232 |
| 2005/0119696 A1* | 6/2005 | Walters | A61B 17/06166 606/228 |
| 2006/0155328 A1* | 7/2006 | Foerster | A61B 17/06166 606/228 |
| 2007/0010857 A1* | 1/2007 | Sugimoto | A61B 17/00234 606/232 |
| 2008/0065114 A1* | 3/2008 | Stone | A61B 17/0401 606/279 |
| 2008/0140093 A1* | 6/2008 | Stone | A61B 17/0469 606/228 |
| 2008/0312689 A1* | 12/2008 | Denham | D04C 1/06 606/228 |
| 2009/0082805 A1* | 3/2009 | Kaiser | A61B 17/06166 606/228 |
| 2011/0022083 A1* | 1/2011 | DiMatteo | A61B 17/06166 606/228 |
| 2011/0270278 A1* | 11/2011 | Overes | A61B 17/0487 606/228 |

* cited by examiner

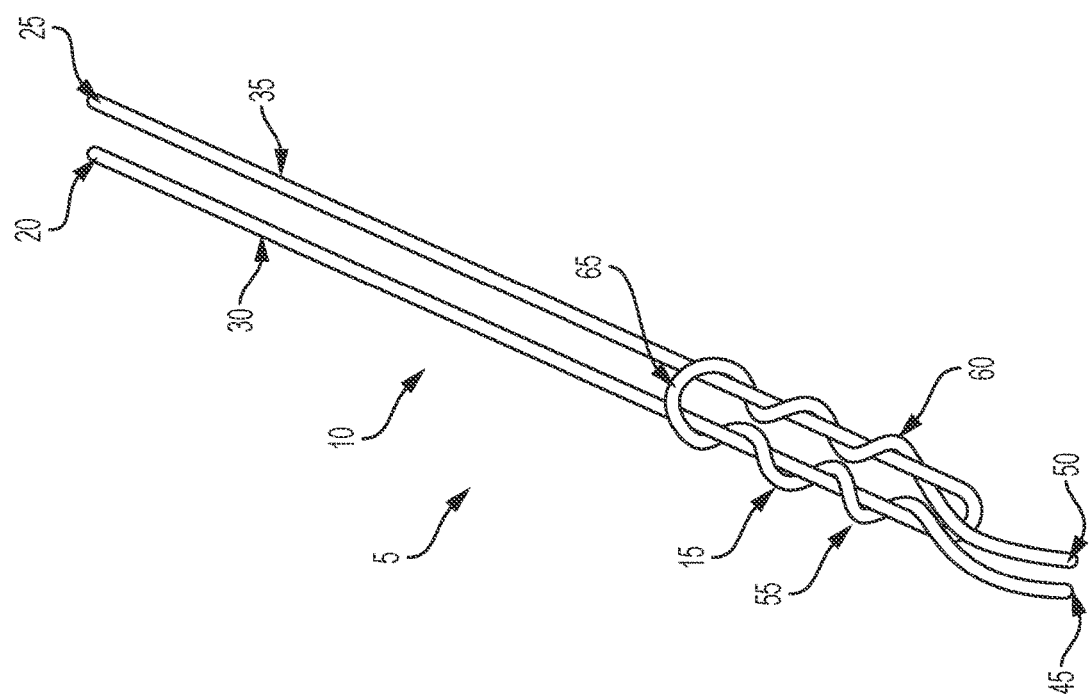
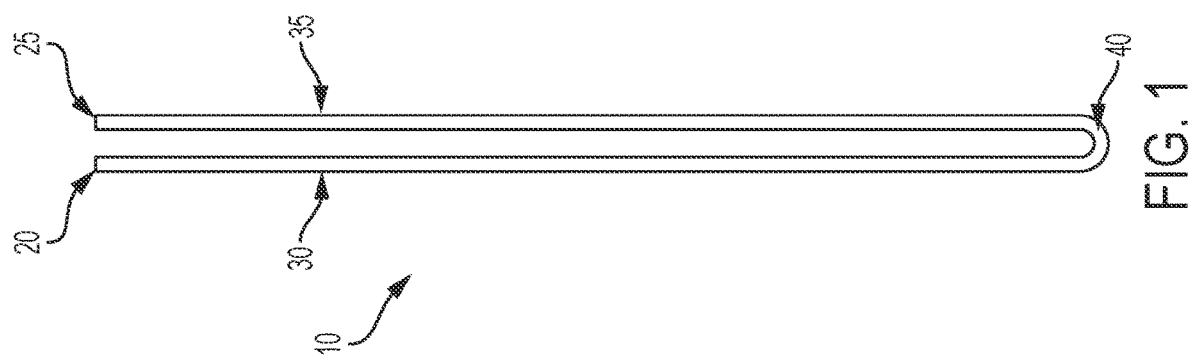

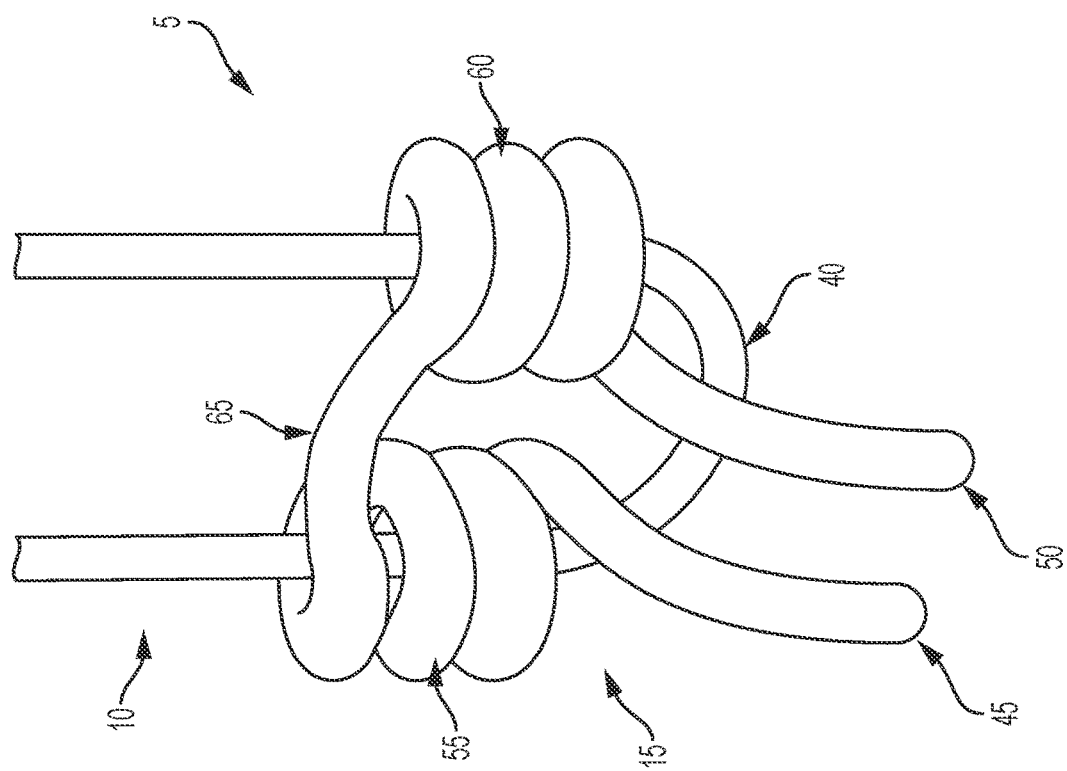
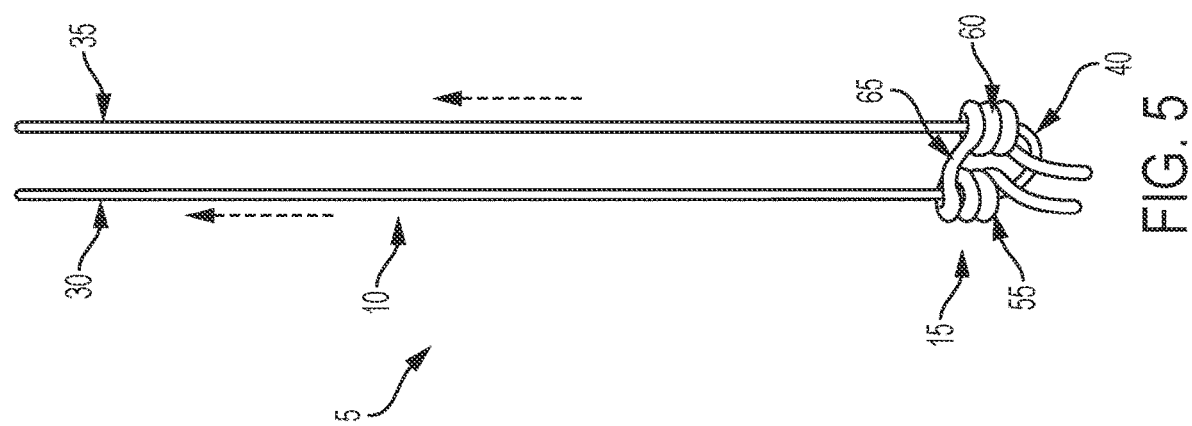

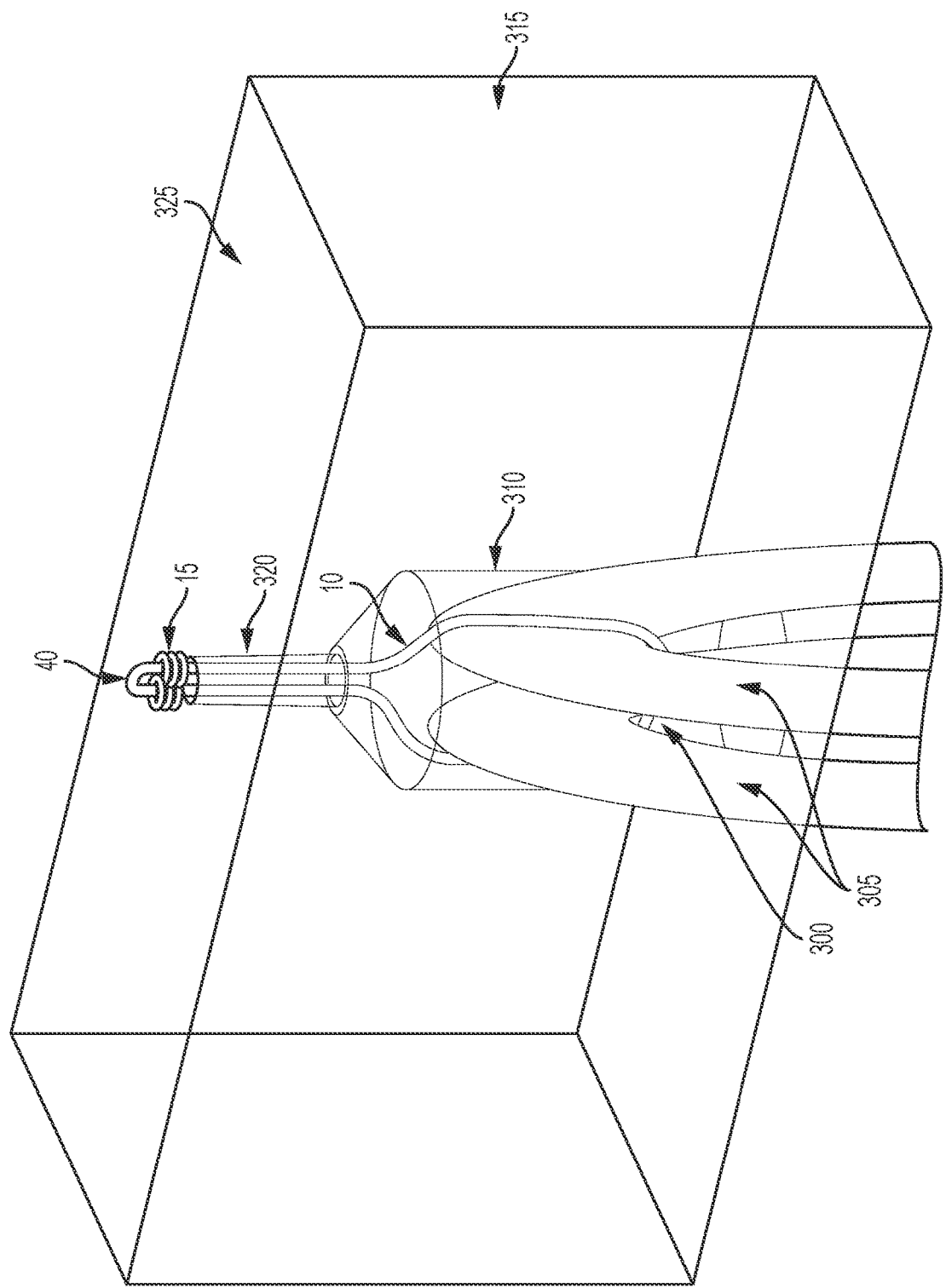

METHOD AND APPARATUS FOR SECURING AN OBJECT TO BONE, INCLUDING THE PROVISION AND USE OF A NOVEL SUTURE ASSEMBLY FOR SECURING AN OBJECT TO BONE

REFERENCE TO PENDING PRIOR PATENT APPLICATIONS

This patent application is a continuation of U.S. patent application Ser. No. 15/890,868 filed on Feb. 7, 2018, which is a divisional of U.S. patent application Ser. No. 14/842,183 filed Sep. 1, 2015 by Dennis McDevitt for METHOD AND APPARATUS FOR SECURING AN OBJECT TO BONE, INCLUDING THE PROVISION AND USE OF A NOVEL SUTURE ASSEMBLY FOR SECURING AN OBJECT TO BONE which patent application in turn is a continuation-in-part of pending prior U.S. patent application Ser. No. 13/093,634, filed Apr. 25, 2011 by Dennis McDevitt et al. for METHOD AND APPARATUS FOR SECURING AN OBJECT TO BONE, INCLUDING THE PROVISION AND USE OF A NOVEL SUTURE ASSEMBLY FOR SECURING SUTURE TO BONE, which patent application in turn claims benefit of (a) prior U.S. Provisional Patent Application Ser. No. 61/410,027, filed Nov. 4, 2010 by Dennis McDevitt et al. for APPARATUS ASSEMBLY AND METHOD FOR SOFT TISSUE REPAIR; (b) prior U.S. Provisional Patent Application Ser. No. 61/419,334, filed Dec. 3, 2010 by Dennis McDevitt et al. for APPARATUS ASSEMBLY AND METHOD FOR SOFT TISSUE REPAIR; (c) prior U.S. Provisional Patent Application Ser. No. 61/422,859, filed Dec. 14, 2010 by Dennis McDevitt et al. for APPARATUS ASSEMBLY AND METHOD FOR SOFT TISSUE REPAIR; and (d) pending prior U.S. Provisional Patent Application Ser. No. 61/443,325, filed Feb. 16, 2011 by Dennis McDevitt et al. for APPARATUS ASSEMBLY AND METHOD FOR SOFT TISSUE REPAIR; and claims benefit of pending prior U.S. Provisional Patent Application Ser. No. 61/443,342, filed Feb. 16, 2011 by Dennis McDevitt et al. for APPARATUS ASSEMBLY AND METHOD FOR SOFT TISSUE REPAIR.

The six (6) above-identified patent applications are hereby incorporated herein by reference.

FIELD OF THE INVENTION

This invention relates to surgical methods and apparatus in general, and more particularly to surgical methods and apparatus for securing an object to bone.

BACKGROUND OF THE INVENTION

Numerous devices are currently available to secure an object to bone. More particularly, screws, staples, cement and sutures have all been used to secure soft tissue (e.g., ligaments, tendons, muscles, etc.), bone and inanimate objects (e.g., prostheses) to bone.

In certain situations it can be desirable to attach a segment of a suture to bone, such that another segment of that suture can be used to secure an object (e.g., soft tissue) to the bone. This is generally accomplished by attaching a segment of the suture to a suture anchor, and then securing the suture anchor to the bone, such that the suture anchor attaches the suture to the bone. Then another segment of that suture can be used to secure an object (e.g., soft tissue) to the bone. In this respect it should be appreciated that it is common to attach a central segment of the suture to the suture anchor, so as to leave two free ends of the suture available for use in securing an object (e.g., soft tissue) to the bone.

Among other things, such suture anchors have found widespread application in procedures for re-attaching ligaments to bone, e.g., so as to restore a torn rotator cuff in the shoulder.

The aforementioned suture anchors generally comprise substantially rigid bodies to which the suture is attached, either at the time of manufacture or at the time of use. The substantially rigid bodies of the suture anchors may be formed out of a variety of materials (e.g., metal, plastic, bone, etc.) according to their particular form and function. By way of example but not limitation, a screw-type suture anchor is typically formed out of metal or plastic, a toggle-type suture anchor is typically formed out of plastic, an expansion-type suture anchor is typically formed out of plastic, etc. In any case, however, the body of the suture anchor is generally formed out of a substantially rigid material which must be reliably secured to the bone, whereby to reliably attach the suture to the bone.

Prior art suture anchors all suffer from one or more deficiencies. These deficiencies include, but are not limited to: (i) various difficulties and/or inconveniences associated with a particular manner of securing the suture anchor to the bone (e.g., screw-type suture anchors require rotational motion, toggle-type suture anchors require toggling within a hole formed in the bone, expansion-type screw anchors require some sort of anchor deformation within a hole formed in the bone, etc.); (ii) difficulties in ensuring that the body of the suture anchor is securely attached to the bone (e.g., toggle-type suture anchors can sometimes fail to properly set in a bone hole and may "skid" back out of the bone hole, expansion-type suture anchors may not expand properly within the bone hole and may pull back out of the bone hole, etc.); (iii) complications associated with a possible failure of the suture anchor (and the possible subsequent migration of the substantially rigid body of the suture anchor out of the bone hole and into the working portion of a joint); (iv) an inability to scale the suture anchor down to a size small enough to allow the suture anchor to be used in and around delicate anatomical structures; (v) the need to form relatively large holes in the anatomy in order to secure the suture anchor to the bone; (vi) inadequate holding power (e.g., limits to the holding strength which can be provided by a screw-type suture anchor, or the holding strength which can be provided by a toggle-type suture anchor, etc.); and/or (vii) inconveniences associated with attaching the suture to the suture anchor (either during manufacture or at the time of use), etc.

In addition to the foregoing, in some circumstances an object (e.g., soft tissue) may be attached to a bone using a device other than a suture anchor. By way of example but not limitation, a graft ligament (e.g., a graft anterior cruciate ligament, also known as an ACL) may be attached to bone (e.g., the femur) by fixing a portion of the graft ligament in a bone tunnel formed in the bone, e.g., by using an interference screw to wedge the graft ligament against an opposing side wall of the bone tunnel, or by using a crosspin to suspend the graft ligament in the bone tunnel, or by using a suture sling (formed by a button and suture) to suspend the graft ligament in the bone tunnel, etc.

Such graft ligament fixation devices all suffer from one or more deficiencies, e.g., interference screws prevent bone/soft tissue ingrowth about the entire circumference of the bone hole, crosspins can be difficult to accurately deploy, suture slings can present problems when deploying the button on the far side of the bone, etc.

As a result, one object of the present invention is to provide a novel suture assembly for securing suture to bone.

Another object of the present invention is to provide a novel suture assembly for securing suture to bone which does not suffer from the deficiencies associated with the prior art.

Another object of the present invention is to provide a novel suture assembly for securing an object (e.g., soft tissue) to bone.

Another object of the present invention is to provide a novel method for securing an object (e.g., soft tissue) to bone.

SUMMARY OF THE INVENTION

These and other objects of the present invention are addressed by the provision and use of a novel suture assembly for securing suture to bone, such that the suture may be used to secure an object (e.g., soft tissue) to the bone.

In one preferred form of the present invention, there is provided a suture assembly comprising: a first suture having a generally U-shaped configuration comprising a first arm, a second arm and a bridge connecting the first arm to the second arm; a second suture comprising a first arm, a second arm and a bridge connecting the first arm to the second arm; the first arm of the second suture being wrapped around the first arm of the first suture in a first direction, and the second arm of the second suture being wrapped around the second arm of the first suture in a second, opposite direction; the suture assembly being capable of assuming (i) a longitudinally-extended, radially-contracted first configuration, and (ii) a longitudinally-contracted, radially-expanded second configuration.

In another preferred form of the present invention, there is provided a method for attaching an object to an anatomical structure, the method comprising: providing a suture assembly comprising: a first suture having a generally U-shaped configuration comprising a first arm, a second arm and a bridge connecting the first arm to the second arm; a second suture comprising a first arm, a second arm and a bridge connecting the first arm to the second arm; the first arm of the second suture being wrapped around the first arm of the first suture in a first direction, and the second arm of the second suture being wrapped around the second arm of the first suture in a second, opposite direction; the suture assembly being capable of assuming (i) a longitudinally-extended, radially-contracted first configuration, and (ii) a longitudinally-contracted, radially-expanded second configuration; inserting the suture assembly into an opening in the anatomical structure while the suture assembly is in its longitudinally-extended, radially-contracted first configuration, with the first and second arms of the first suture extending from the opening in the anatomical structure; and transforming the suture assembly from its longitudinally-extended, radially-contracted first configuration to its longitudinally-contracted, radially-expanded second configuration in order to secure the suture assembly to the anatomical structure.

In another preferred form of the present invention, there is provided a system for securing an object to an anatomical structure, the system comprising: a suture assembly comprising: a first suture having a generally U-shaped configuration comprising a first arm, a second arm and a bridge connecting the first arm to the second arm; a second suture comprising a first arm, a second arm and a bridge connecting the first arm to the second arm; the first arm of the second suture being wrapped around the first arm of the first suture in a first direction, and the second arm of the second suture being wrapped around the second arm of the first suture in a second, opposite direction; the suture assembly being capable of assuming (i) a longitudinally-extended, radially-contracted first configuration, and (ii) a longitudinally-contracted, radially-expanded second configuration; and an inserter assembly for deploying the suture assembly in the anatomical structure, the inserter assembly comprising: an insertion tube for carrying at least a portion of the suture assembly within the insertion tube when the suture assembly is in its longitudinally-extended, radially-contracted first configuration; and a push rod for engaging the suture assembly when the suture assembly is disposed within the insertion tube.

In another preferred form of the present invention, there is provided an assembly comprising: a first suture having a generally O-shaped configuration comprising a first arm, a second arm, a first bridge connecting the first arm to the second arm, and a second bridge connecting the first arm to the second arm, the first bridge opposing the second bridge so that the first suture comprises a closed loop; a second suture comprising a first arm, a second arm and a bridge connecting the first arm to the second arm; the first arm of the second suture being wrapped around the first arm of the first suture in a first direction, and the second arm of the second suture being wrapped around the second arm of the first suture in a second, opposite direction; the assembly being capable of assuming (i) a longitudinally-extended, radially-contracted first configuration, and (ii) a longitudinally-contracted, radially-expanded second configuration.

In another preferred form of the present invention, there is provided a method for attaching an elongated object to an anatomical structure, the method comprising: providing a suture assembly comprising: a first suture having a generally O-shaped configuration comprising a first arm, a second arm, a first bridge connecting the first arm to the second arm, and a second bridge connecting the first arm to the second arm, the first bridge opposing the second bridge so that the first suture comprises a closed loop; a second suture comprising a first arm, a second arm and a bridge connecting the first arm to the second arm; the first arm of the second suture being wrapped around the first arm of the first suture in a first direction, and the second arm of the second suture being wrapped around the second arm of the first suture in a second, opposite direction; the suture assembly being capable of assuming (i) a longitudinally-extended, radially-contracted first configuration, and (ii) a longitudinally-contracted, radially-expanded second configuration; looping the elongated object through the closed loop of the first suture; passing the suture assembly along an opening in the anatomical structure while the suture assembly is in its longitudinally-extended, radially-contracted first configuration, so that a first portion of the suture assembly extends out of the opening on a far side of the anatomical structure; and transforming the suture assembly from its longitudinally-extended, radially-contracted first configuration to its longitudinally-contracted, radially-expanded second configuration so as to attach the elongated object to the anatomical structure when the elongated object is held under tension.

In another preferred form of the present invention, there is provided a method for attaching an elongated object to an anatomical structure, the method comprising: looping the elongated object through a closed loop of a suture assembly; passing the suture assembly along an opening in the anatomical structure so that a first portion of the suture assembly extends out of the opening on a far side of the anatomical structure; and transforming the suture assembly from a first configuration to a second configuration so that the first portion of the suture assembly is unable to be retracted back into the opening so as to attach the elongated object to the anatomical structure when the elongated object is held under tension.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 1 and 2 are schematic views showing how the novel suture assembly of the present invention is assembled;

FIGS. 5 and 6 are schematic views showing the novel suture assembly of FIG. 2 in a longitudinally-contracted, radially-expanded second configuration for lodging in a bone hole;

FIGS. 57-59 are schematic views showing the novel suture assembly of FIG. 55 being used to suspend a plurality of graft ligaments in a bone tunnel.

DETAILED DESCRIPTION OF THE PREFERRED EMBODIMENTS

The Novel Suture Assembly in General

Figure 4:
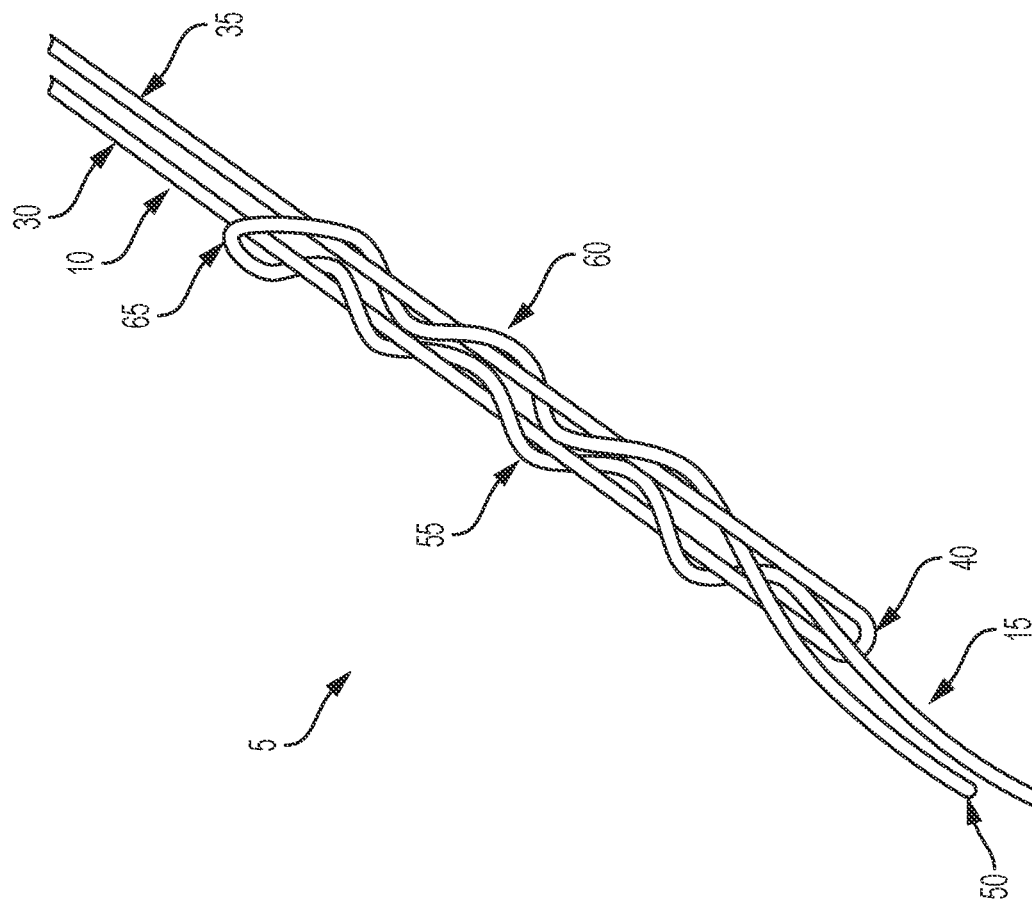
FIGS. 3 and 4 are schematic views showing the novel suture assembly of FIG. 2 in longitudinally-expanded, radially-contracted first configuration for insertion into a bone hole.

Looking first at FIGS. 1 and 2, there is shown a novel suture assembly 5 for securing suture to bone, such that the suture may be used to secure an object (e.g., soft tissue) to the bone.

More particularly, novel suture assembly 5 generally comprises a first length of suture ("first suture") 10 (FIGS. 1 and 2) and a second length of suture ("second suture") 15 (FIG. 2).

First suture 10 comprises a first end 20 and second end 25 such that when first suture 10 is folded back on itself, it forms a first arm 30 which includes first end 20, and a second arm 35 which includes second end 25, with first arm 30 being connected to second arm 35 via a bridge 40.

Second suture 15 comprises a first end 45 and second end 50 such that when second suture 15 is folded back on itself, it forms a first arm 55 which includes first end 45, and a second arm 60 which includes second end 50, with first arm 55 being connected to second arm 60 via a bridge 65.

Second suture 15 is wrapped around first suture 10 by (i) folding second suture 15 back on itself so as to provide first arm 55 and second arm 60, with first arm 55 being connected to second arm 60 via a bridge 65; (ii) positioning bridge 65 of second suture 15 across first arm 30 and second arm 35 of first suture 10, with bridge 65 of second suture 15 being spaced from bridge 40 of first suture 10; and (iii) wrapping first arm 55 of second suture 15 around first arm 30 of first suture 10, and wrapping second arm 60 of second suture 15 around second arm 35 of first suture 10, in the manner shown in FIG. 2.

More particularly, first arm 55 of second suture 15 is wrapped around first arm 30 of first suture 10 in a first direction, and second arm 60 of second suture 15 is wrapped around second arm 35 of first suture 10 in a second, opposite direction. In other words, first arm 55 of second suture 15 is arranged in a first helical configuration about first arm 30 of first suture 10, and second arm 60 of second suture 15 is arranged in a second, oppositely wound helical configuration about second arm 35 of first suture 10. This opposite winding of first arm 55 and second arm 65 is a very significant aspect of the present invention, since it provides the novel suture assembly with a highly defined, appropriately shaped and consistently reproducible structure when the novel suture assembly is subsequently transformed from its longitudinally-expanded, radially-contracted first configuration into its longitudinally-contracted, radially-expanded second configuration, as will hereinafter be discussed in further detail.

In one preferred form of the present invention, first arm 55 of second suture 15 is wrapped three times around first arm 30 of first suture 10 in a clockwise direction (when viewed from the frame of reference of bridge 65), and second arm 60 of second suture 15 is wrapped three times around second arm 35 of first suture 10 in a countereclockwise direction (when viewed from the frame of reference of bridge 65), in the manner shown in FIG. 2.

In another preferred form of the present invention, first arm 55 of second suture 15 is wrapped four times around first arm 30 of first suture 10 in a clockwise direction (when viewed from the frame of reference of bridge 65), and second arm 60 of second suture 15 is wrapped four times around second arm 35 of first suture 10 in a countereclockwise direction (when viewed from the frame of reference of bridge 65).

And in another preferred form of the present invention, first arm 55 of second suture 15 is wrapped two times around first arm 30 of first suture 10 in a clockwise direction (when viewed from the frame of reference of bridge 65), and second arm 60 of second suture 15 is wrapped two times around second arm 35 of first suture 10 in a countereclockwise direction (when viewed from the frame of reference of bridge 65).

On account of the foregoing construction, novel suture assembly 5 can assume a first configuration in which second suture 15 is wrapped loosely around first suture 10, i.e., so that the suture assembly assumes a longitudinally-elongated, radially-contracted first configuration (FIGS. 3 and 4) which is suitable for insertion into a hole formed in bone. However, when first arm 30 and second arm 35 of first suture 10 are thereafter tensioned while holding bridge 65 of second suture 15 stationary (or by applying some other holding force to second suture 15, e.g., friction from the adjacent side wall of a bone hole containing suture assembly 5), suture assembly 5 can be transformed from the aforementioned longitudinally-elongated, radially-contracted first configuration into a longitudinally-contracted, radially-expanded second configuration (FIGS. 5 and 6) which is suitable for securing the suture assembly in the hole formed in bone. Significantly, and as will hereinafter be discussed in further detail, when novel suture assembly 5 is so disposed in a hole formed in bone, first arm 30 and second arm 35 of first suture 10 will extend out of the hole formed in the bone and be available for securing an object (e.g., soft tissue) to the bone.

And significantly, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), it is possible to form the highly defined, appropriately shaped structure shown in FIGS. 5 and 6 in a highly consistent manner when suture assembly 5 is transformed from its longitudinally-expanded, radially-contracted first configuration (FIGS. 3 and 4) into its longitudinally-contracted, radially-expanded second configuration (FIGS. 5 and 6).

And significantly, the highly defined, appropriately shaped and consistently reproducible structure shown in FIGS. 5 and 6 is capable of carrying substantial loads without losing its defined shape when loads are applied to the first and second ends 20, 25 of first suture 10. As a result, when suture assembly 5 is inserted into a bone hole while in its longitudinally-expanded, radially-contracted first configuration and is thereafter transformed into its longitudinally-contracted, radially-expanded second configuration, novel suture assembly 5 will provide an excellent suture anchor with high holding strength.

Among other things, it should be appreciated that, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively; which yield, as shown in this example, a plurality of holes formed by the first arm of the solid and cylindrically shaped second suture through which the first arm of the first suture is passed, and a plurality of holes formed by the second arm of the second suture through which the second arm of the first suture is passed), the novel suture assembly 5 does not form a knot in either its longitudinally-expanded, radially-contracted first configuration (FIGS. 3 and 4) or its longitudinally-contracted, radially-expanded second configuration (FIGS. 5 and 6). In either configuration, the novel suture assembly 5 may be disassembled by simply pulling first arm 30 of first suture 10, or by pulling second arm 35 of first suture 10, away from second suture 15, whereby to "undo" the suture assembly.

In one preferred form of the present invention, first suture 10 comprises a first length of woven suture, and second suture 15 comprises a second length of woven suture.

Thus it will be seen that novel suture assembly 5 constitutes an all-suture construct which can assume (i) a longitudinally-expanded, radially-contracted first configuration for insertion into a hole formed in a bone, and (ii) a longitudinally-contracted, radially-expanded second configuration for lodging in the hole formed in the bone, with the suture assembly providing a pair of free suture arms extending out of the hole formed in the bone for use in securing an object (e.g., soft tissue) to the bone. Significantly, by forming the novel suture assembly 5 in the specific manner discussed above, the longitudinally-contracted, radially-expanded second configuration of the suture assembly constitutes a highly defined, appropriately shaped and consistently reproducible structure which is able to carry substantial loads without losing its defined shape, whereby to provide a suture anchor with high holding strength. And significantly, by forming the novel suture assembly 5 in the specific manner discussed above, the novel suture assembly 5 does not form a knot in either its longitudinally-expanded, radially-contracted first configuration (FIGS. 3 and 4) or its longitudinally-contracted, radially-expanded second configuration (FIGS. 5 and 6). In either configuration, the novel suture assembly 5 may be disassembled by simply pulling first arm 30 of first suture 10, or by pulling second arm 35 of first suture 10, away from second suture 15, whereby to "undo" the suture assembly.

Novel Inserter Assembly for Deploying the Novel Suture Assembly in Bone

Looking next at FIGS. 7-11, there is shown an inserter assembly 70 and associated cannulated drill guide assembly 75 which may be used to deploy novel suture assembly 5 in bone. Inserter assembly 70 in turn comprises an insertion tube assembly 80 and a push rod assembly 85.

More particularly, cannulated drill guide assembly 75 generally comprises an elongated drill guide tube 86 having a distal end 90 carrying distal end prongs 95, and a proximal end 100 carrying a drill guide handle 105. A lumen 106 extends through elongated drill guide tube 86 and drill guide handle 105.

Insertion tube assembly 80 generally comprises an elongated insertion tube 107 having a distal end 110 sized to receive novel suture assembly 5 (either loosely or, more preferably, tightly compressed) when the novel suture assembly is in its aforementioned longitudinally-expanded, radially-contracted first configuration (FIGS. 3, 4, 10 and 11). Elongated insertion tube 107 of insertion tube assembly 80 also comprises a proximal end 115 carrying an insertion tube handle 120. A lumen 121 extends through elongated tube insertion 107 and insertion tube handle 120.

Push rod assembly 85 generally comprises a push rod 122 having a distal end 125 terminating in a distal end surface 130, and a proximal end 135 carrying a push rod handle 140.

Insertion tube assembly 80 is sized so that its elongated insertion tube 107 can be received within lumen 106 of cannulated drill guide assembly 75 such that, when cannulated drill guide assembly 75 is used to form a hole in a bone, the distal end of insertion tube assembly 80 can be delivered to that hole in a bone, as will hereinafter be discussed.

Push rod assembly 85 is sized so that its push rod 122 can be slidably received within lumen 121 of insertion tube assembly 80 such that, when novel suture assembly 5 is disposed within the distal end 110 of elongated insertion tube 107 of insertion tube assembly 80, advancement of push rod assembly 85 relative to insertion tube assembly 80, and/or retraction of insertion tube assembly 80 while holding push rod assembly 85 stationary, will cause novel suture assembly 5 to be released from distal end 110 of elongated insertion tube 107 of insertion tube assembly 80, as will hereinafter be discussed. Once novel suture assembly 5 has been released from distal end 110 of elongated insertion tube 107 of insertion tube assembly 80, tensioning first arm 30 and second arm 35 of first suture 10, while push rod assembly 85 holds bridge 65 of second suture 15 from moving proximally, will cause novel suture assembly 5 to transform from its longitudinally-elongated, radially-contracted first configuration (FIGS. 3, 4, 10 and 11) into its longitudinally-contracted, radially-expanded second configuration (FIGS. 5 and 6).

Insertion tube assembly 80 is also sized so that its lumen 121 will accommodate first and second arms 30, 35 of first suture 10 alongside push rod 122 of push rod assembly 85 when push rod 122 is disposed in lumen 121 of insertion tube assembly 80.

Novel suture assembly 5 is intended to be disposed within the distal end of insertion tube assembly 80, distal to push rod assembly 85, with first arm 30 and second arm 35 of first suture 10 extending out the proximal end of inserter assembly 70 via lumen 121 of insertion tube assembly 80, with first arm 30 and second arm 35 of first suture 10 extending alongside push rod 122 of push rod assembly 85. Preferably novel suture assembly 5 is tightly compressed within the distal end of insertion tube assembly 80, so as to provide the largest possible differential between the diameter of the radially-elongated, radially-contracted first configuration (FIGS. 3, 4, 10 and 11) and the longitudinally-contracted, radially-expanded second configuration (FIGS. 5 and 6), whereby to minimize the size of the bone hole and thereby increase holding power in the bone. In this respect it should be appreciated that by winding first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively, it is possible for the first and second sutures 10, 15 to "self-accommodate" within the interior of insertion tube assembly 80, thereby permitting maximum compression of the novel suture assembly within the insertion tube assembly. Furthermore, by leaving first end 45 and second end 50 of second suture 15 free (i.e., unconnected) relative to one another, the first and second sutures 10, 15 can further self-accommodate within the interior of insertion tube assembly 80, thereby permitting maximum compression of the novel suture assembly within the insertion tube assembly. Thus it will be appreciated that, by forming novel suture assembly 5 in the specific manner discussed above, the suture assembly is capable of self-accommodating itself into the smallest possible diameter within the insertion tube assembly, thereby permitting maximum compression of the novel suture assembly within the insertion tube assembly, and hence permitting use of a smaller bone hole and thus providing maximum holding power within the bone.

Using the Novel Suture Assembly to Secure Suture to Bone, in Order to Secure an Object to Bone Novel suture assembly 5 may be used to secure suture to bone, such that the suture may be used to secure an object (e.g., soft tissue) to the bone.

In one preferred form of the invention, inserter assembly 70 and its associated cannulated drill guide assembly 75 may be used to deploy novel suture assembly 5 in bone, in order to secure an object to bone.

More particularly, in one preferred form of the present invention, and looking now at FIGS. 12-18, the distal end of cannulated drill guide assembly 75 is first placed against the surface of a bone 145 (FIG. 12) which is to have suture secured thereto. As this occurs, prongs 95 on the distal end of cannulated drill guide assembly 75 help stabilize the cannulated drill guide assembly against the bone. Then a bone drill (not shown) of the sort well known in the art is advanced through lumen 106 of the cannulated drill guide assembly 75 and into the bone so that a bone hole 150 of appropriate size (diameter and depth) is formed in the bone. Note that bone hole 150 extends through the cortical layer 155 of bone 145 and into the cancellous region 160 of the bone. Then the bone drill is removed from cannulated drill guide assembly 75 while leaving the drill guide in position against bone 145.

Figure 13:
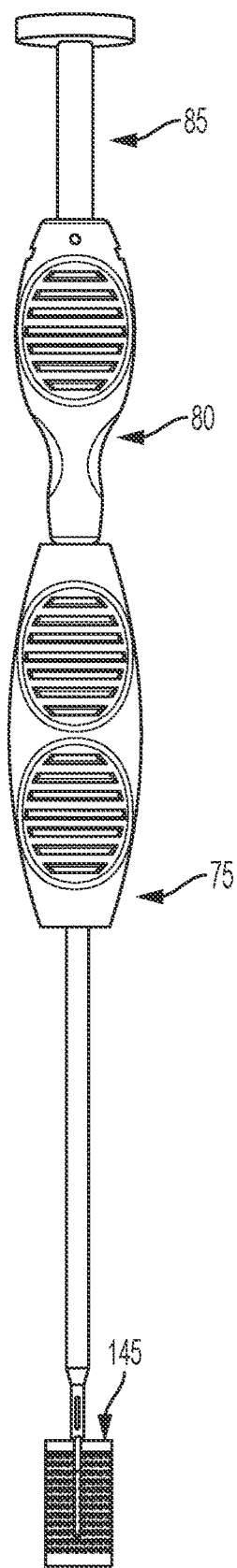
Figure 14:
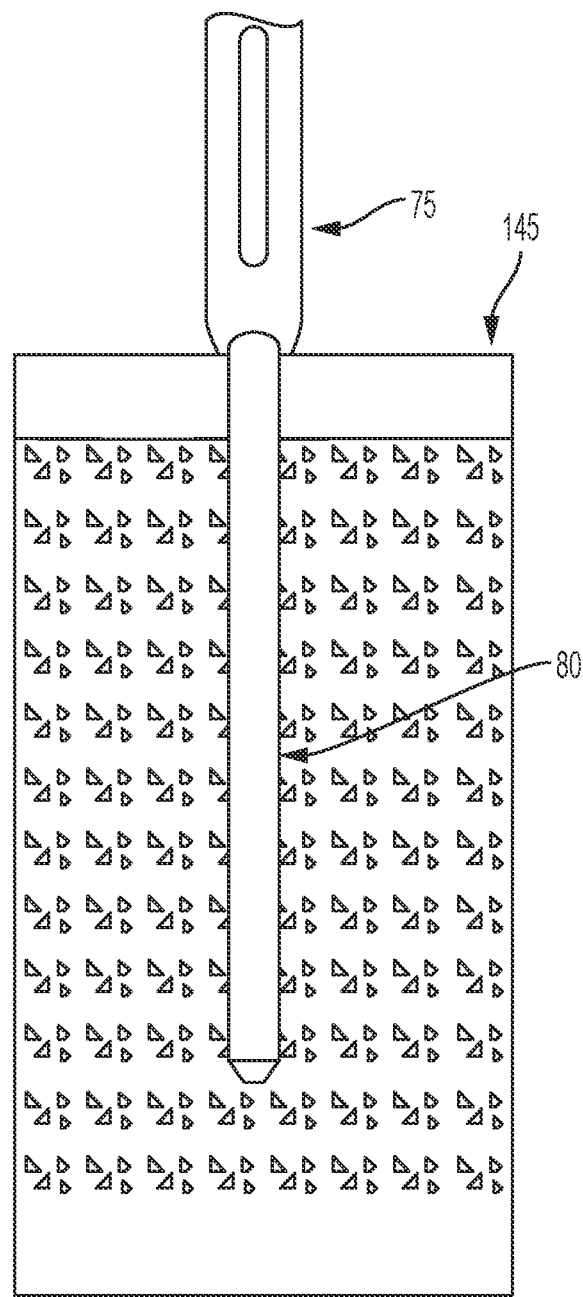

Next, the distal end 110 of insertion tube assembly 80, carrying novel repair contruct 5 therein, is advanced through cannulated drill guide assembly 75 and into bone hole 150 formed in bone 145 (FIGS. 13 and 14). Preferably, push rod 122 of push rod assembly 85 is already disposed within lumen 121 of insertion tube assembly 80 as this occurs, with distal end 130 of push rod assembly 85 sitting against bridge 65 of second suture 15. Alternatively, push rod 122 of push rod assembly 85 can be inserted into lumen 121 of insertion tube assembly 80 after the distal end of insertion tube assembly 80 has been inserted into bone hole 150 so that distal end 130 of push rod assembly 85 sits against bridge 65 of second suture 15.

Figure 15:
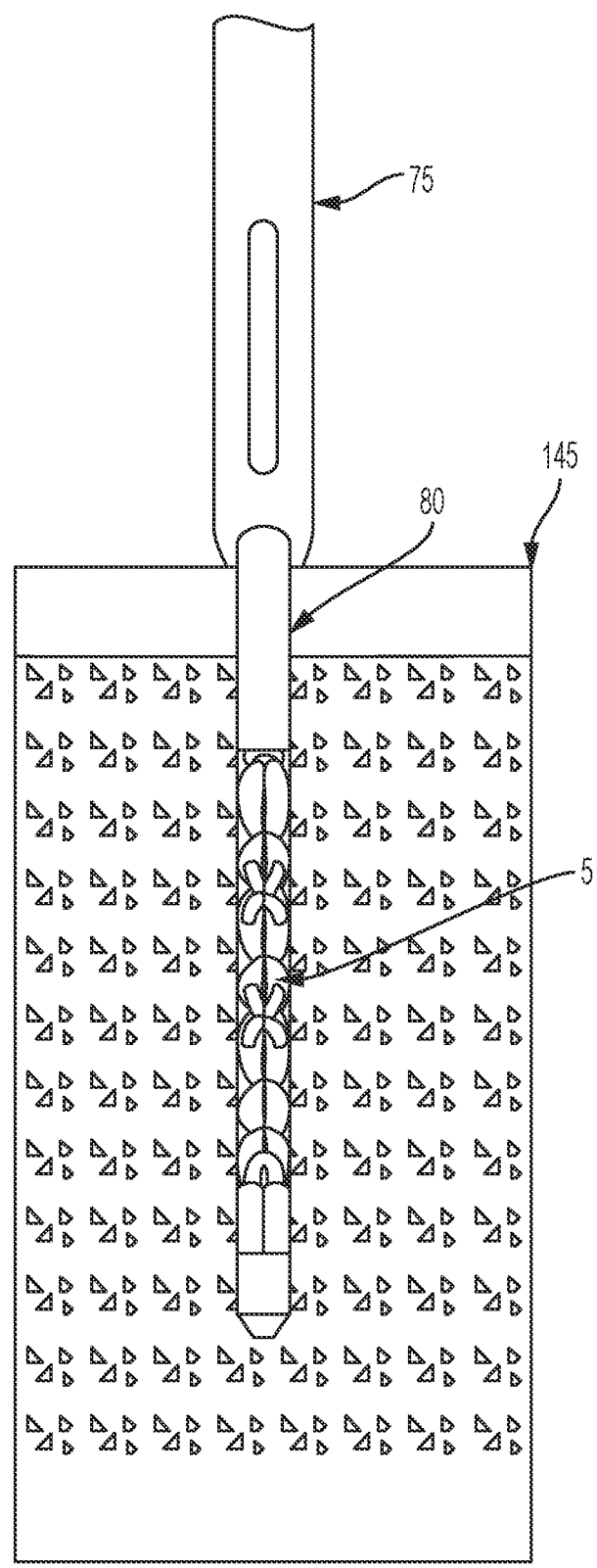
Figure 16:
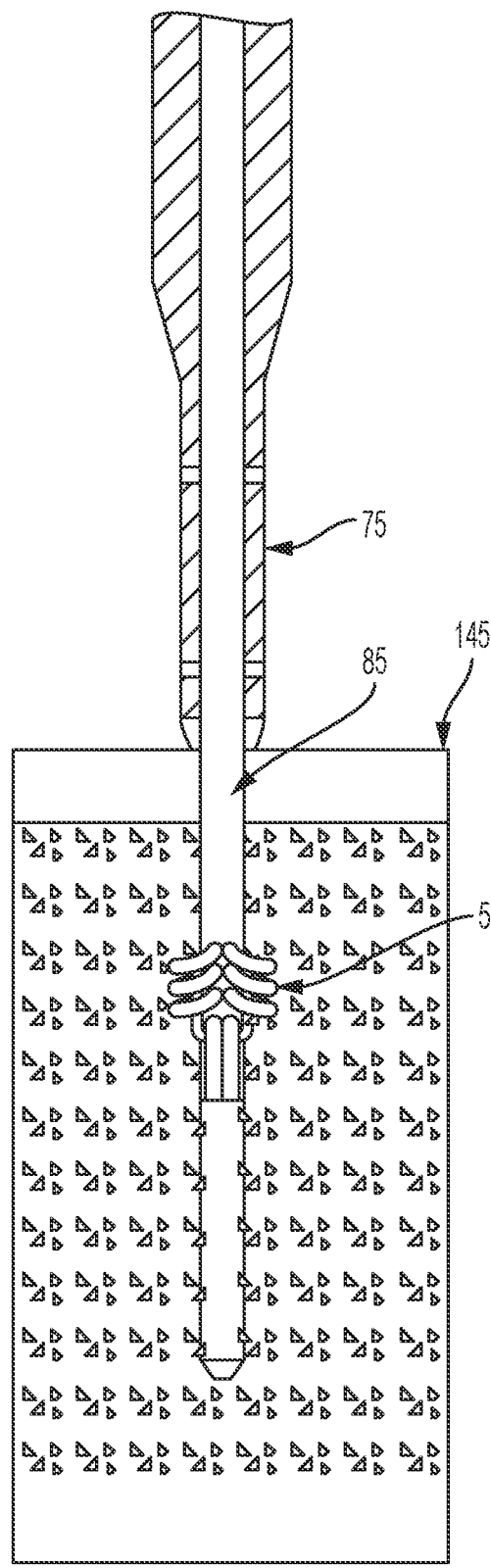
Figure 17:
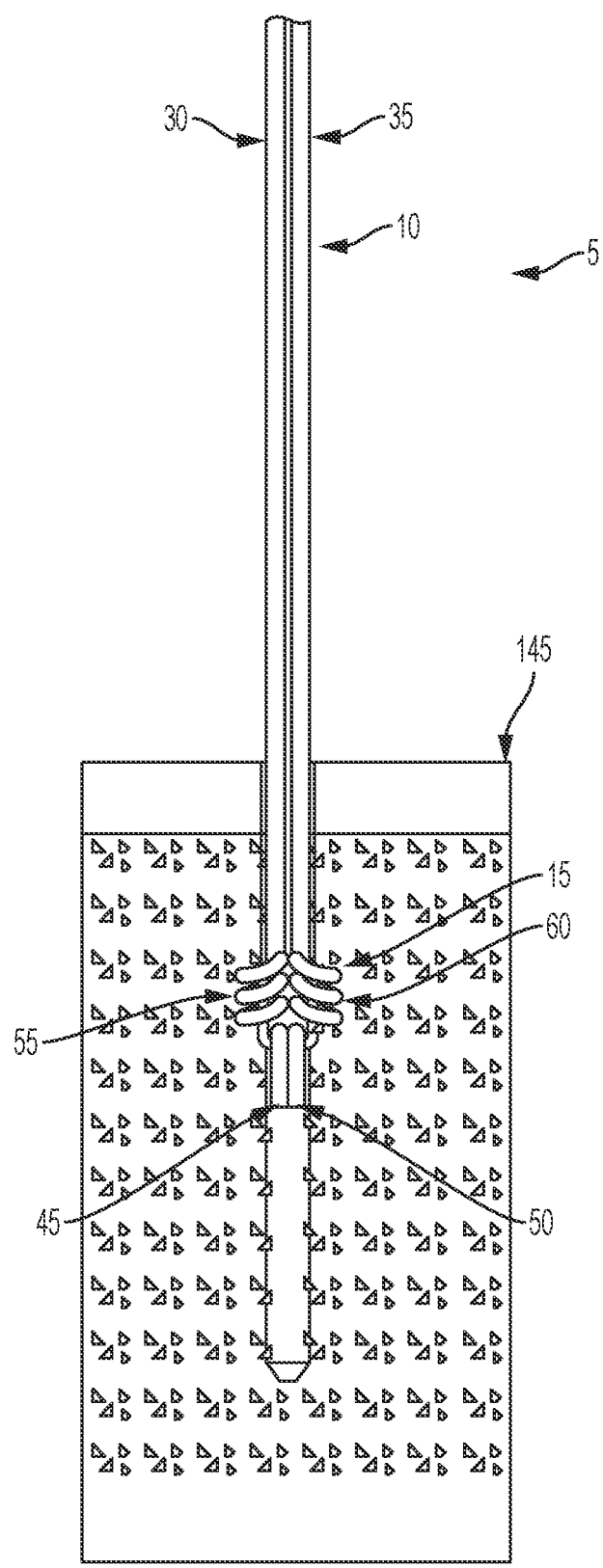
Figure 18:
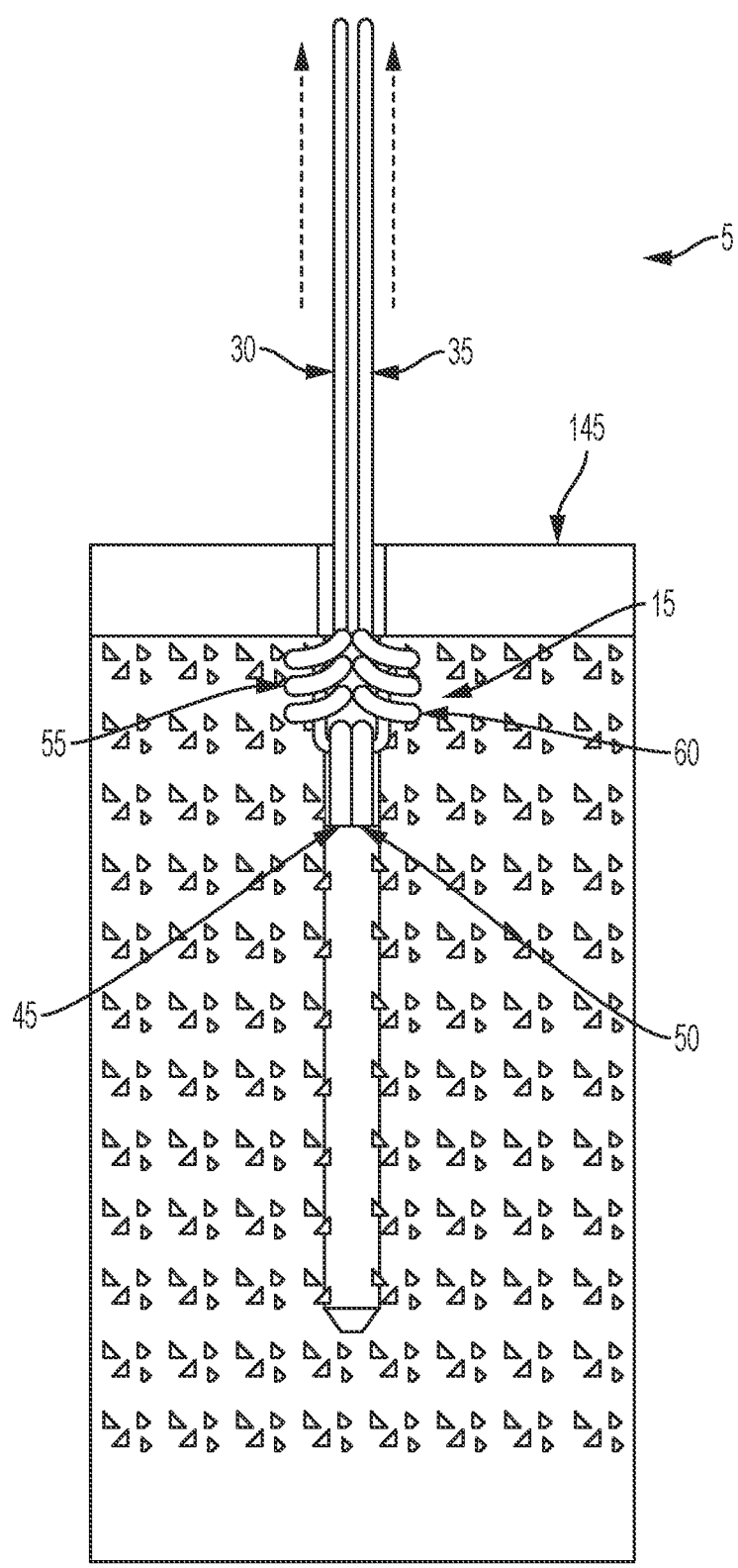

Next, insertion tube assembly 80 is retracted while holding distal end 130 of push rod assembly 85 stationary, so that novel suture assembly 5 is released from the distal end 110 of insertion tube assembly 80 (FIG. 15).

Then, with push rod assembly 85 still in position against bridge 65 of second suture 15, first arm 30 and second arm 35 of first suture 10 are tensioned, thereby transforming novel suture assembly 5 from its longitudinally-extended, radially-contracted first configuration into its longitudinally-contracted, radially-expanded second configuration (FIG. 16), whereby to expand novel suture assembly 5 laterally into the cancellous region 160 of bone 145.

At this point, inserter assembly 70 and cannulated drill guide assembly 75 are removed from the surgical site (FIG. 17), and first arm 30 and second arm 35 of first suture 10 are tensioned further so as to further laterally expand novel suture assembly 5 and cause the laterally-expanded novel suture assembly to seat against the underside of cortical layer 155 of bone 145 (FIG. 18), whereby to secure the novel suture assembly 5 within bone hole 150 (FIG. 18), with first arm 30 and second arm 35 of first suture 10 extending out of the bone hole.

Significantly, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), it is possible to form the highly defined, appropriately shaped structure shown in FIGS. 5 and 6 in a highly consistent manner when suture assembly 5 is transformed from its longitudinally-expanded, radially-contracted first configuration (FIGS. 3 and 4) into its longitudinally-contracted, radially-expanded second configuration (FIGS. 5 and 6).

And significantly, the highly defined, appropriately shaped and consistently reproducible structure shown in FIGS. 5 and 6 is capable of carrying substantial loads without losing its defined shape when loads are applied to the first and second ends 20, 25 of first suture 10. As a result, when suture assembly 5 is inserted into a bone hole while in its longitudinally-expanded, radially-contracted first configuration and is thereafter transformed into its longitudinally-contracted, radially-expanded second configuration, novel suture assembly 5 will provide an excellent suture anchor with high holding strength.

Thereafter, one or both of first arm 30 and second arm 35 of first suture 10 may be used to secure an object (e.g., soft tissue) to the bone. By way of example but not limitation, one or both of first arm 30 and second arm 35 may be passed through a piece of soft tissue (e.g., a ligament) and then tied together so as to secure the soft tissue to bone.

Significantly, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), the novel suture assembly 5 does not form a knot in either its longitudinally-expanded, radially-contracted first configuration (FIGS. 3 and 4) or its longitudinally-contracted, radially-expanded second configuration (FIGS. 5 and 6). In either configuration, the novel suture assembly 5 may be disassembled by simply pulling first arm 30 of first suture 10, or by pulling second arm 35 of first suture 10, away from second suture 15, whereby to "undo" the suture assembly. As a result, if at any time it should be desired to remove the novel suture assembly 5 from bone hole 150, first arm 30 of first suture 10, or second arm 35 of first suture 10, is simply pulled away from second suture 15, whereby to "undo" the suture assembly. Once first suture 10 has been pulled clear of the surgical site, second suture 15 may be extracted from bone hole 150 (e.g., with a narrow suture grasper) and removed from the surgical site.

Figure 19:
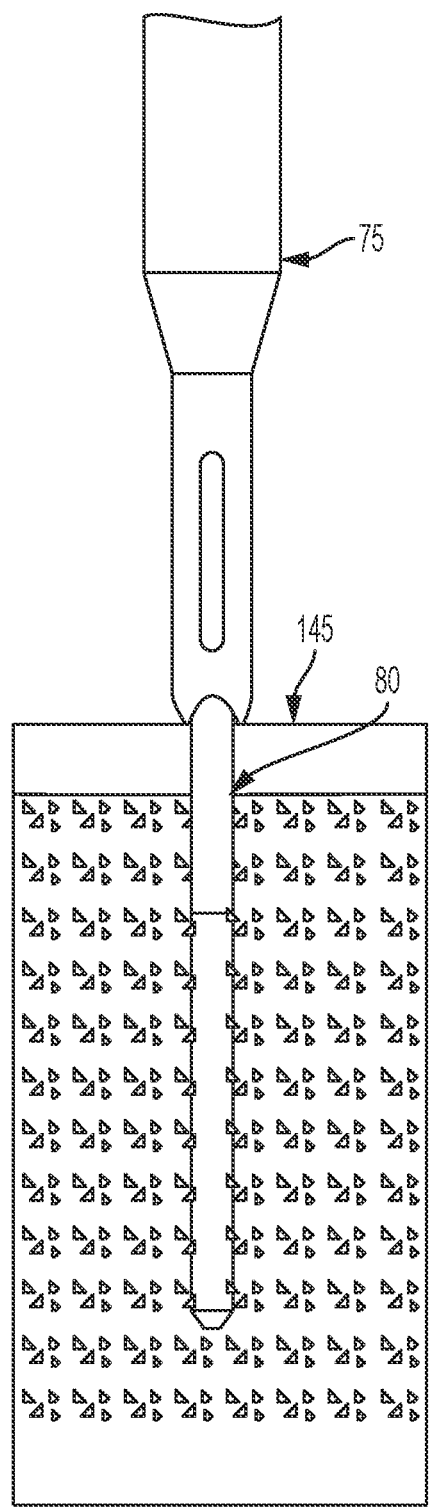
FIGS. 19-26 are schematic views showing another manner in which the inserter assembly and associated cannulated drill guide assembly of FIG. 7 can be used to deploy the novel suture assembly of FIG. 2 in a bone, with FIG. 26 showing the novel suture assembly released from the inserter assembly and in its longitudinally-contracted, radially-expanded second configuration so as to be secured to the bone.
Figure 20:
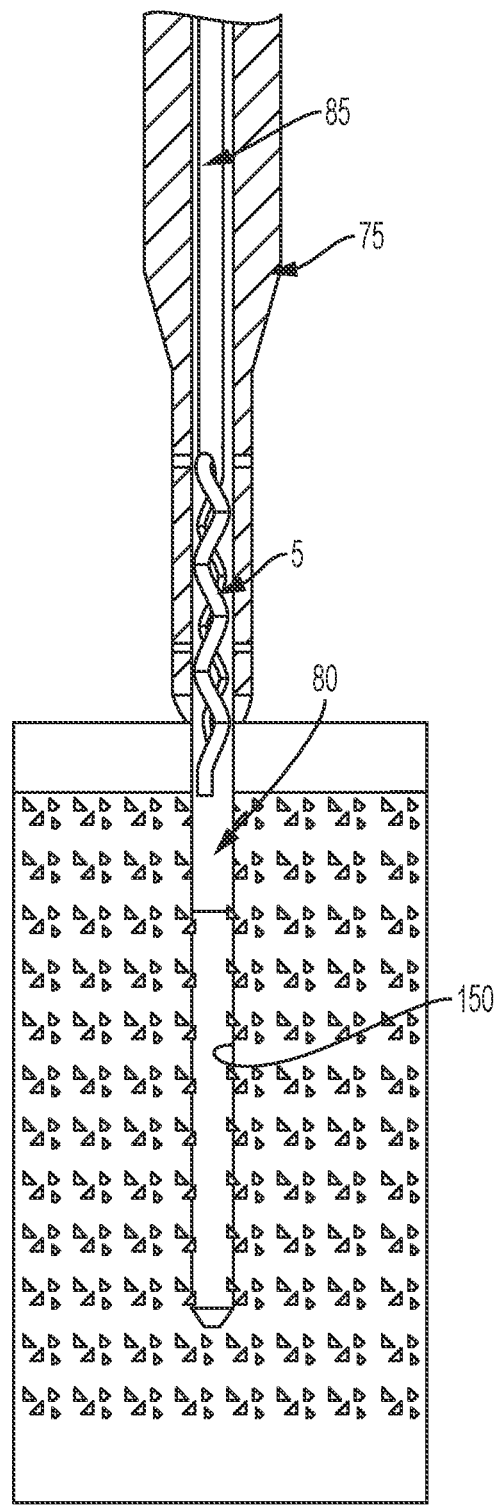

In another preferred form of the present invention, and looking now at FIGS. 19-26, the distal end of cannulated drill guide assembly 75 is first placed against the surface of bone 145, then a bone drill (not shown) is advanced through lumen 106 of the cannulated drill guide assembly 75 and into the bone so that a bone hole 150 of appropriate size (diameter and depth) is formed in the bone, then the bone drill is removed from cannulated drill guide assembly 75 while leaving the cannulated drill guide assembly in position against bone 145, and then the distal end 110 of insertion tube assembly 80, carrying novel suture assembly 5 therein, is advanced through cannulated drill guide assembly 75 and into bone hole 150 formed in bone 145 (FIGS. 19 and 20). Preferably, push rod 122 of push rod assembly 85 is already disposed within lumen 121 of insertion tube assembly 80 as this occurs, with distal end 130 of push rod assembly 85 sitting against bridge 65 of second suture 15. Alternatively, push rod 122 of push rod assembly 85 can be inserted into lumen 121 of insertion tube assembly 80 after the distal end of insertion tube assembly 80 has been inserted into bone hole 150 so that distal end 130 of push rod assembly 85 sits against bridge 65 of second suture 15.

Figure 21:
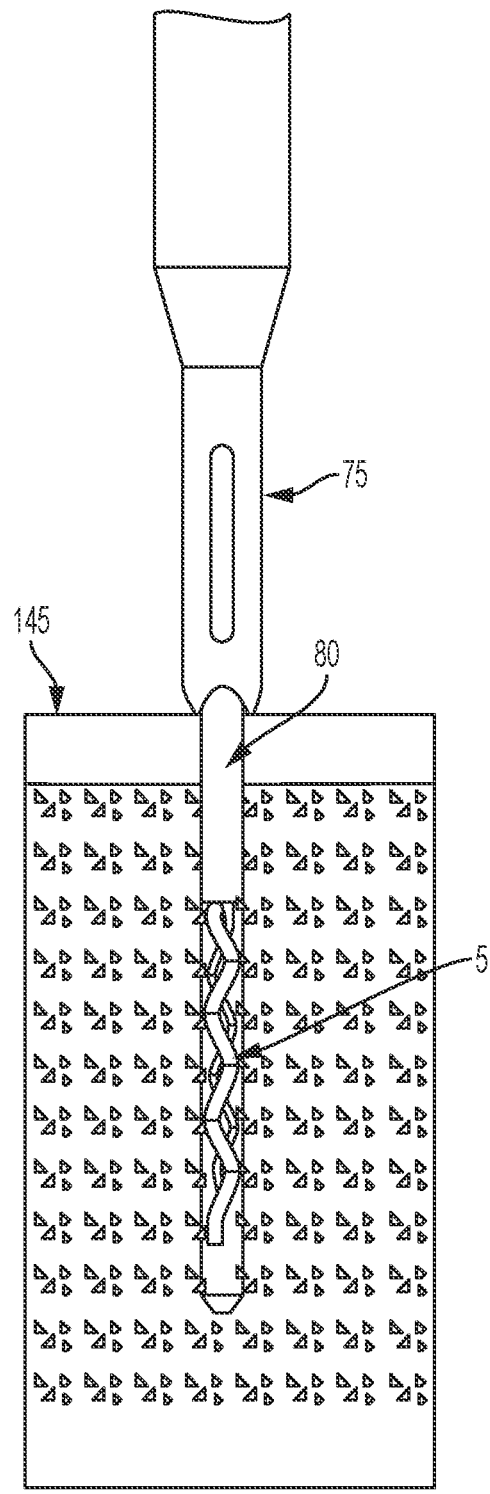
Figure 22:
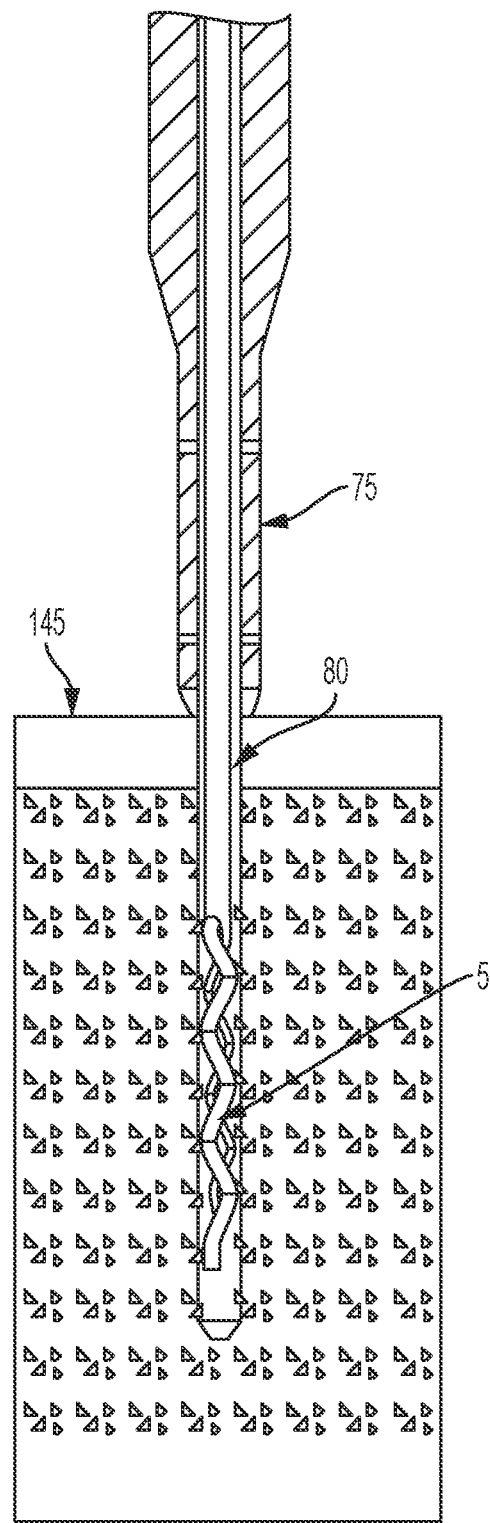
Figure 23:
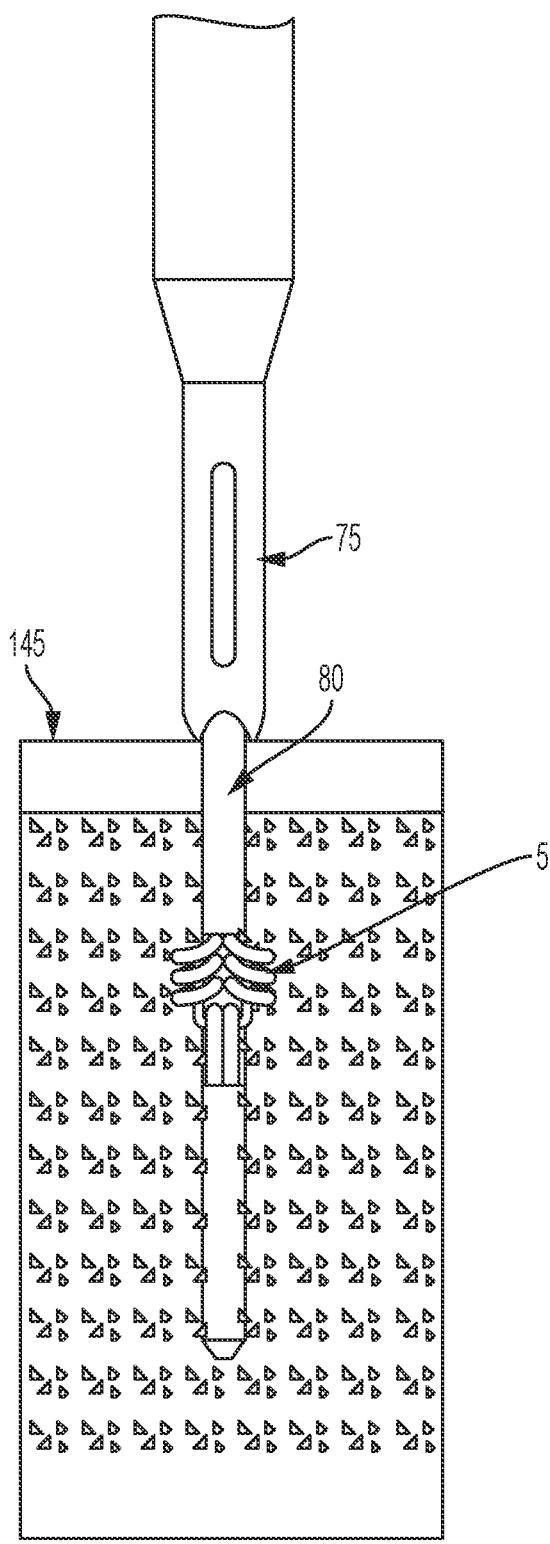
Figure 24:
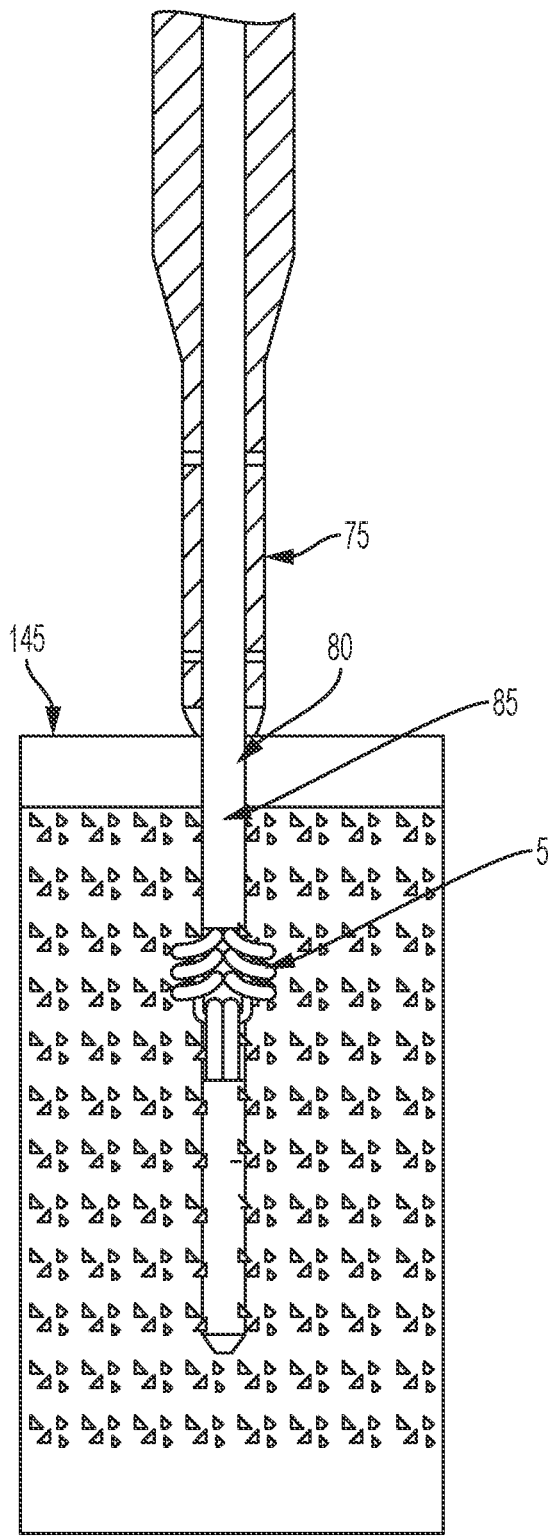
Figure 25:
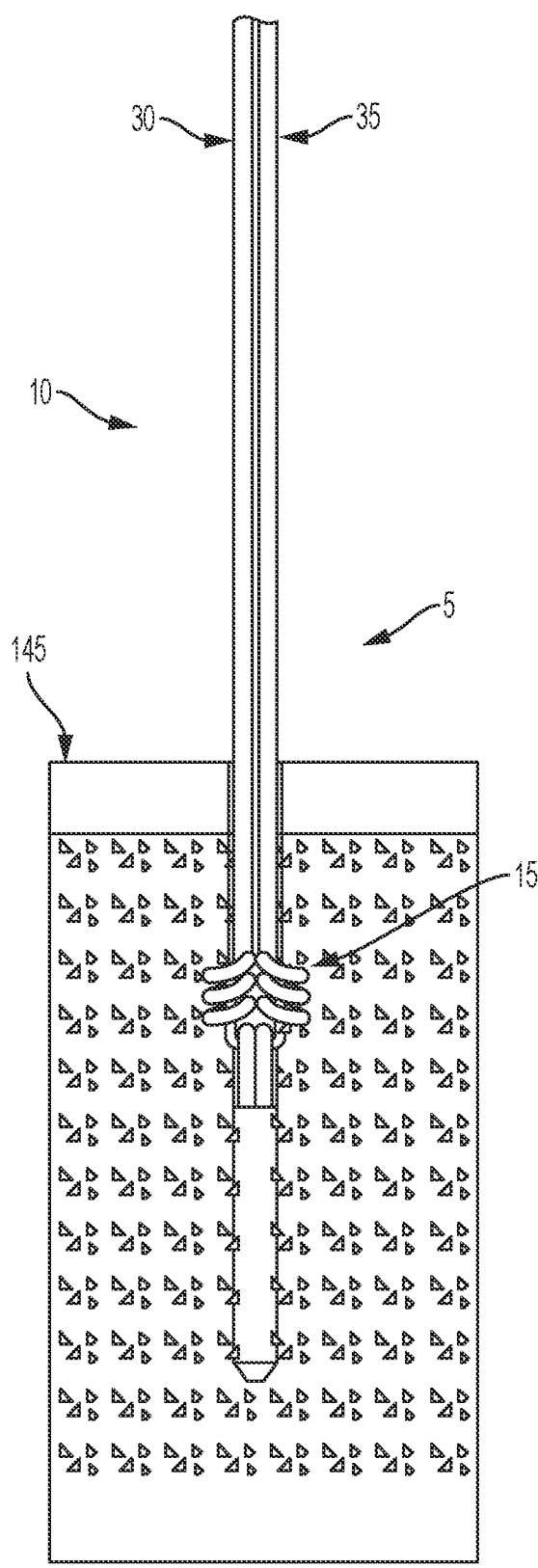
Figure 26:
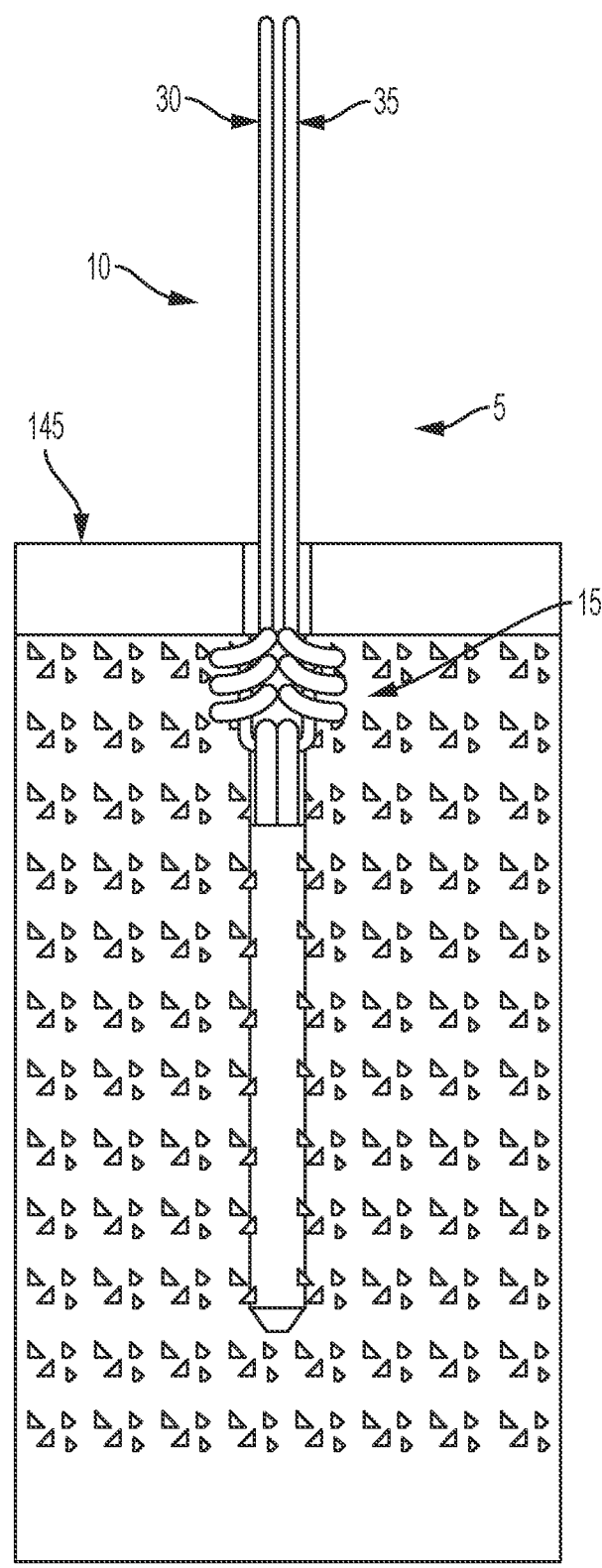
Figure 27:
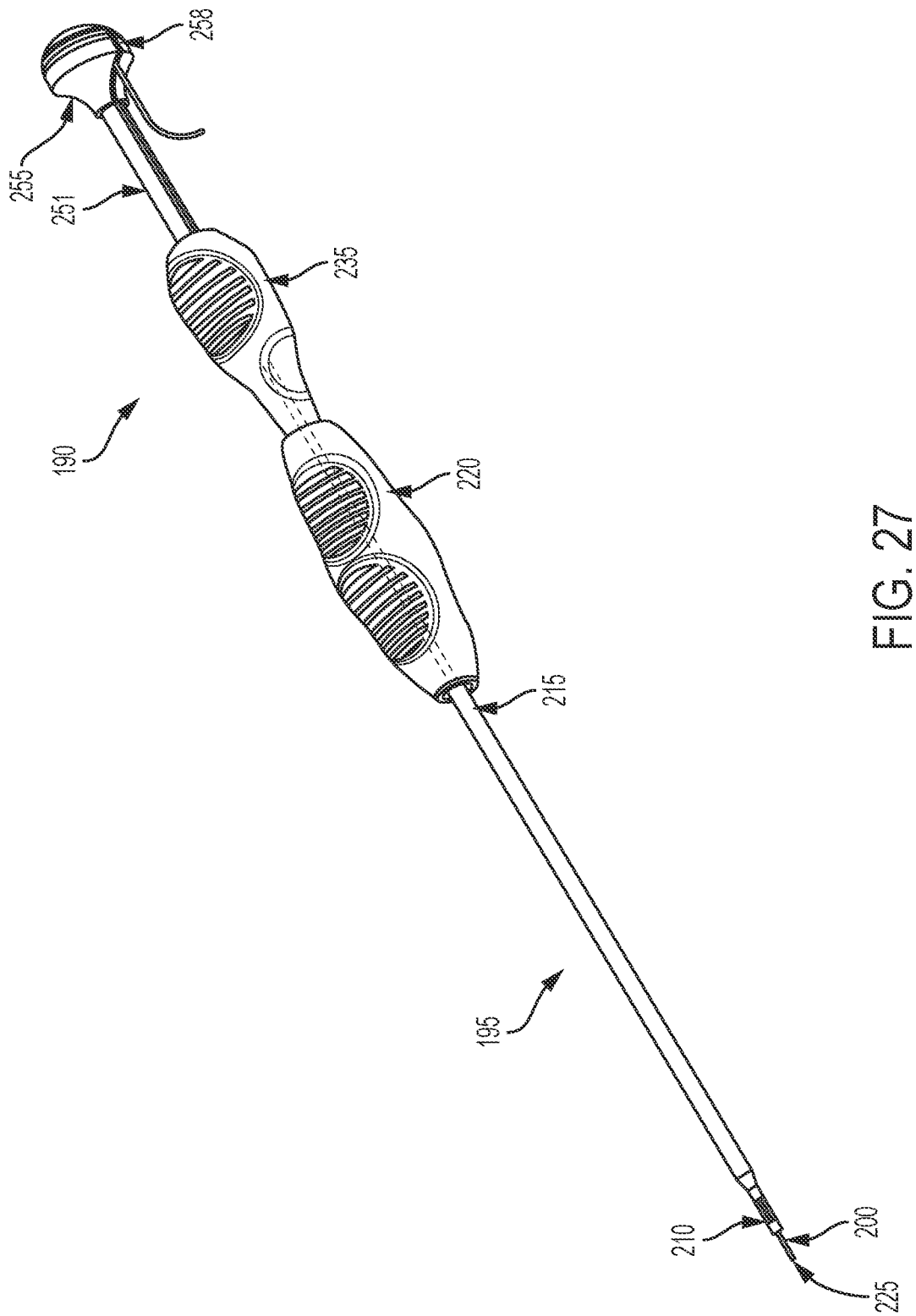
FIGS. 27-31 are schematic views showing another inserter assembly and associated cannulated drill guide assembly which may be used to deploy the novel suture assembly of FIG. 2 in a bone.
Figure 28:
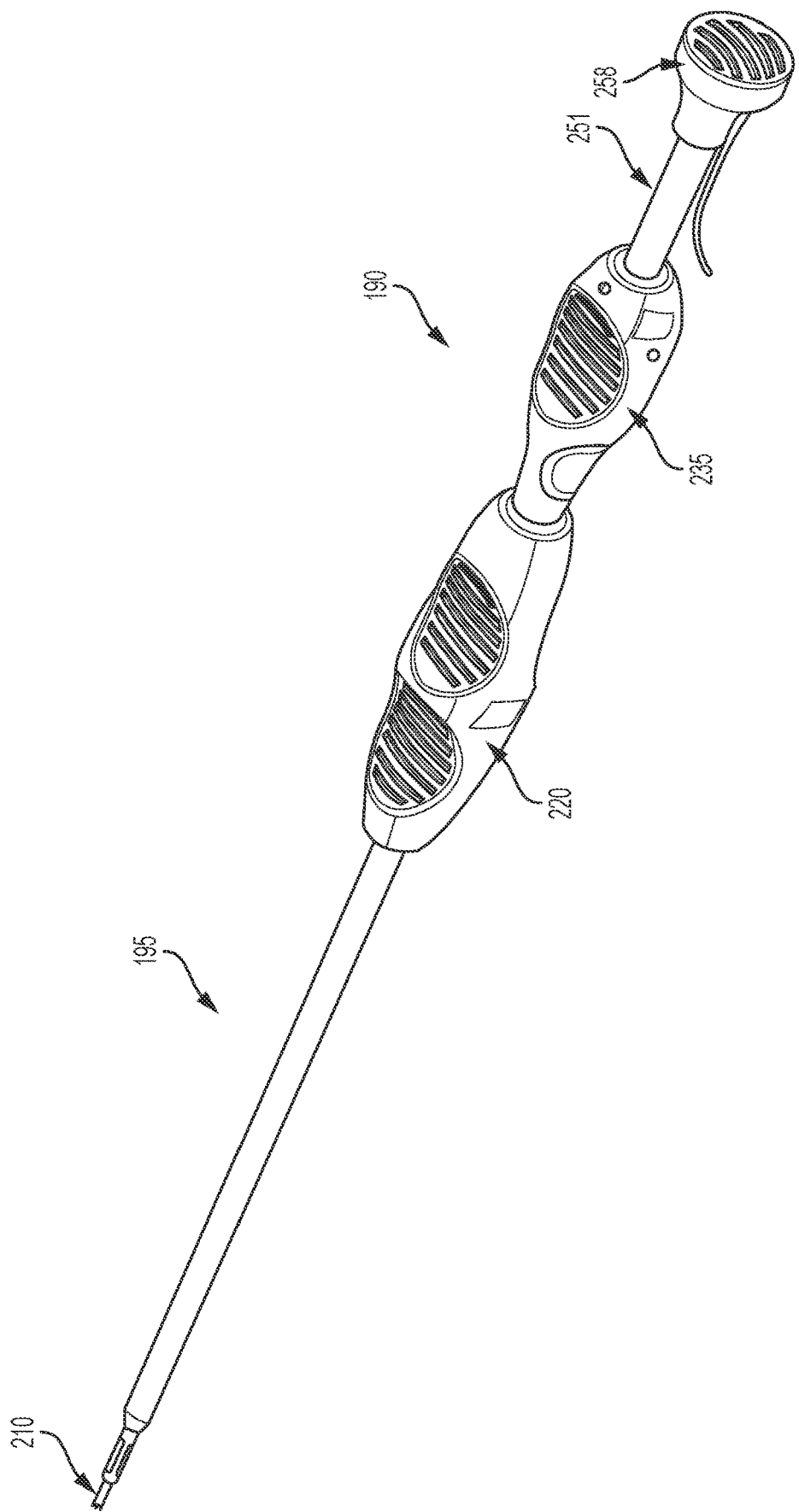
Figure 29:
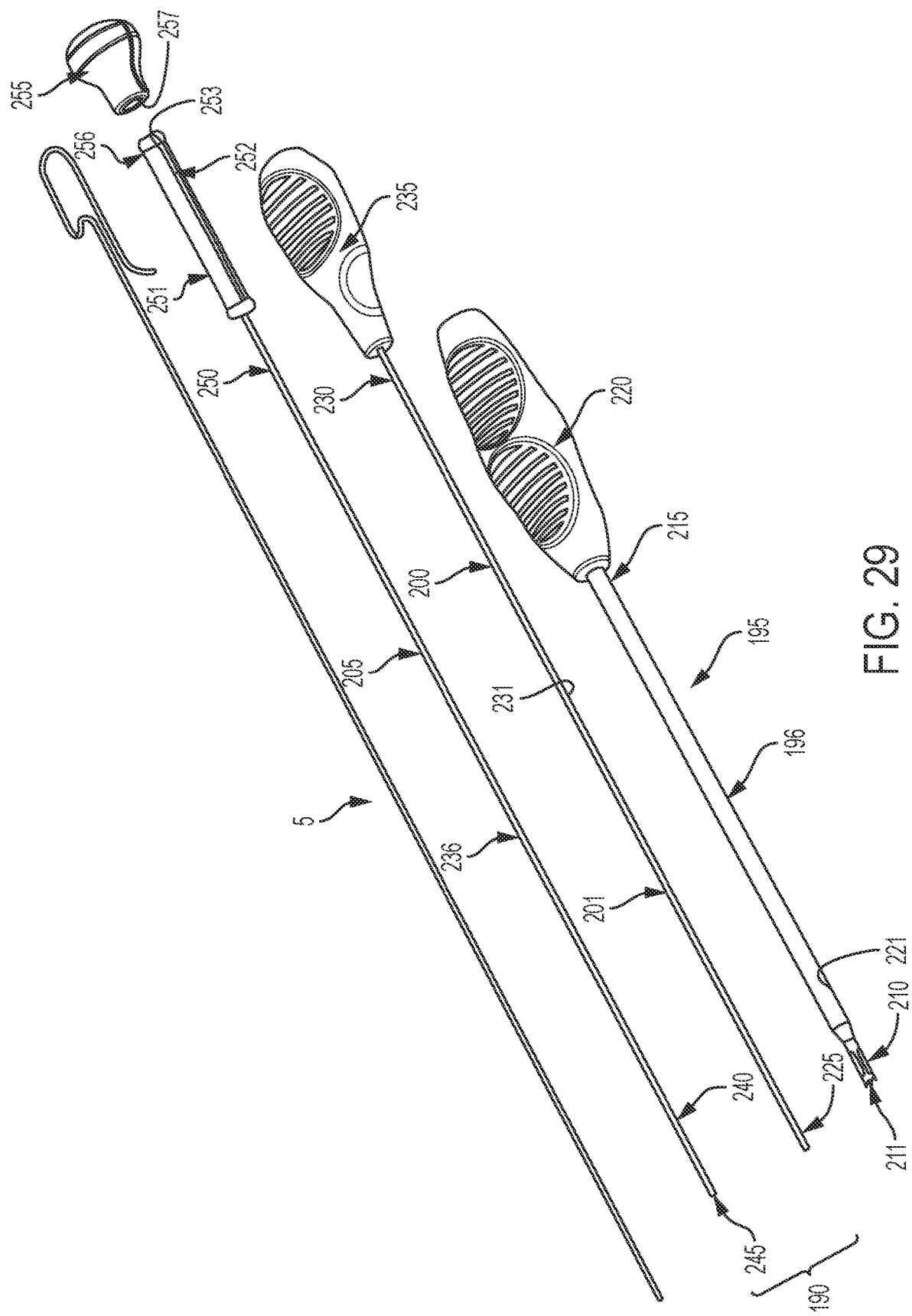
Figure 30:
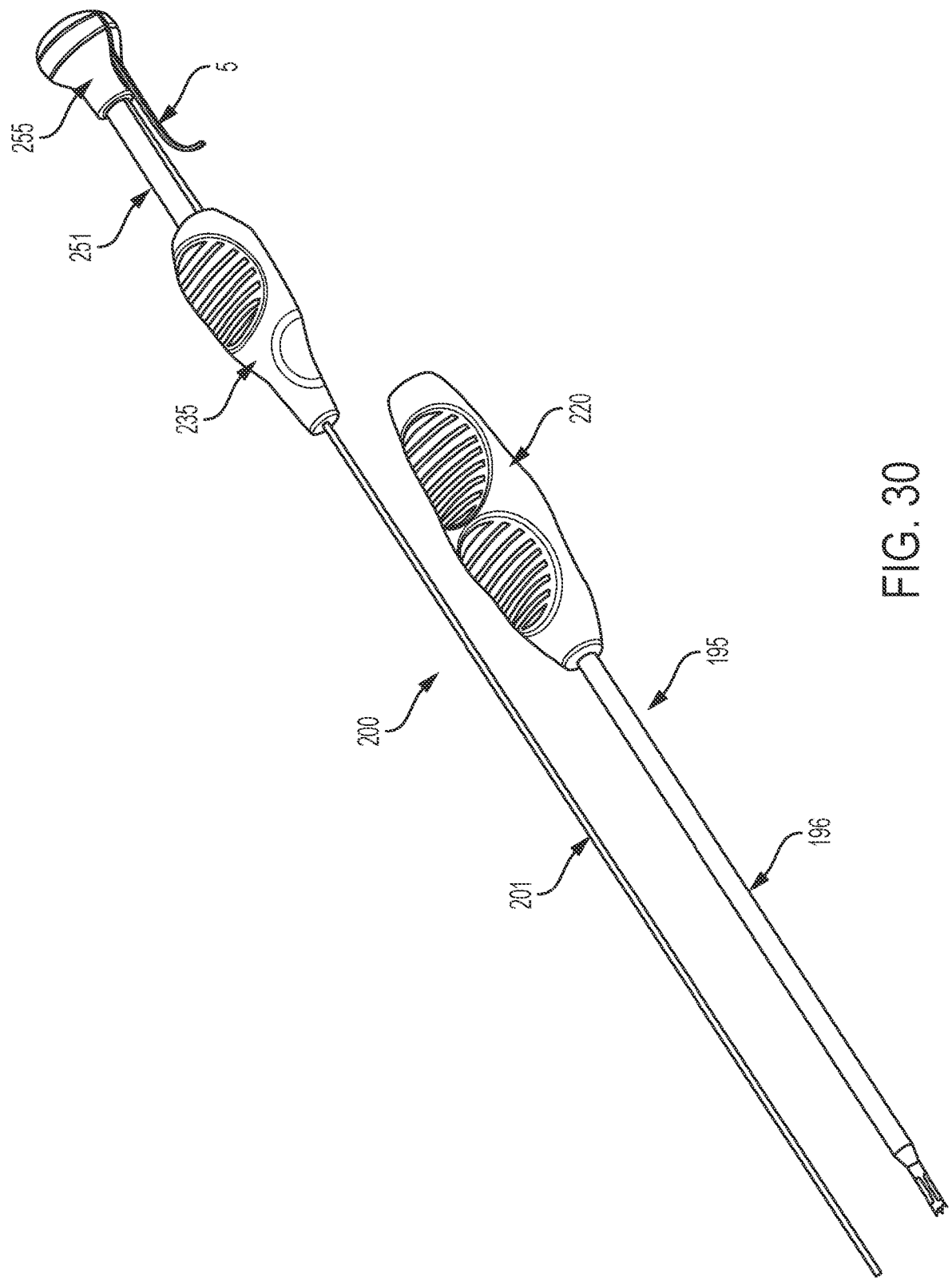
Figure 31:
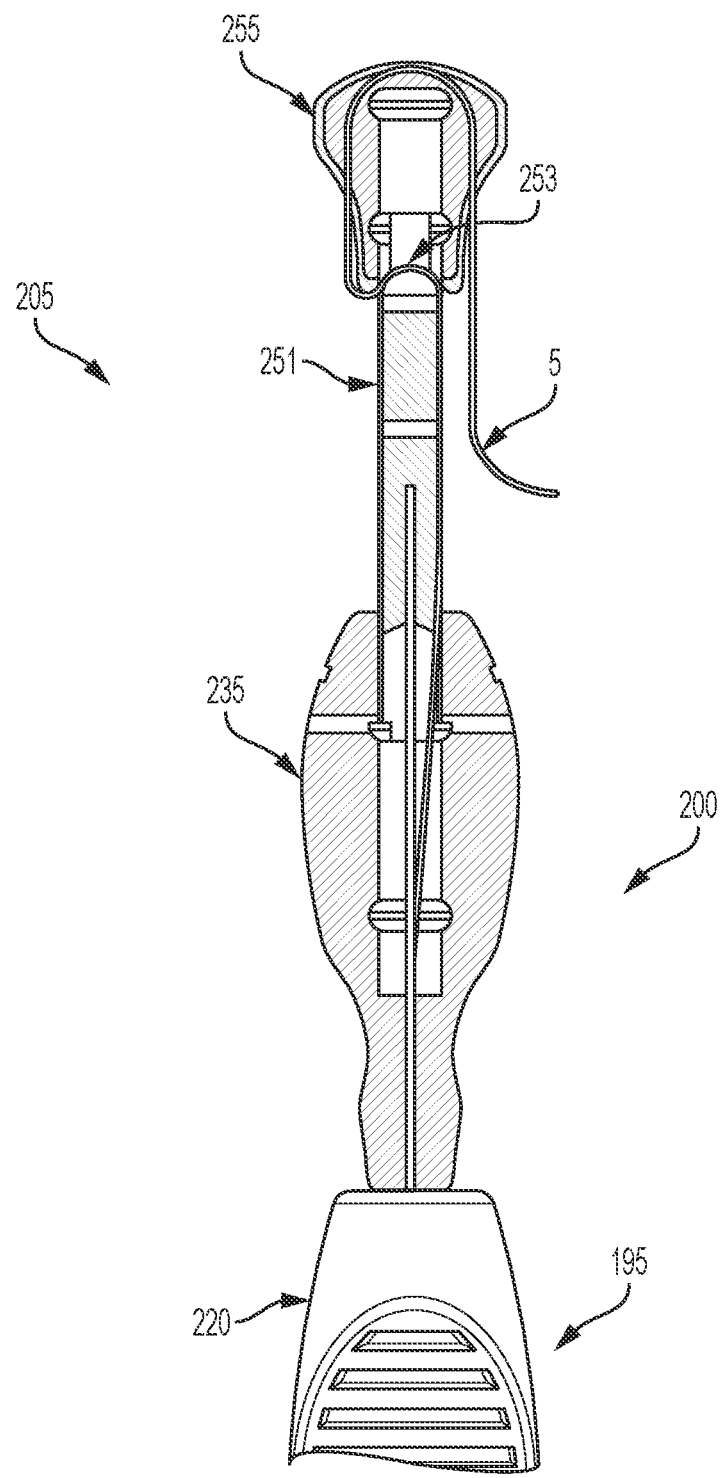
Figure 32:
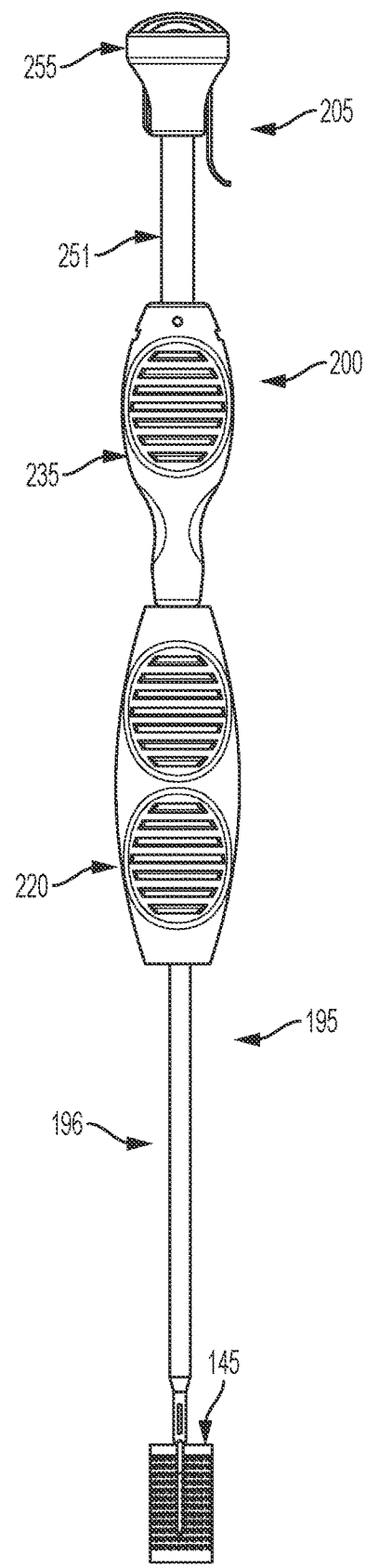
FIGS. 32-49 are schematic views showing the inserter assembly and associated cannulated drill guide assembly of FIGS. 27-31 deploying the novel suture assembly of FIG. 2 in a bone, with FIG. 49 showing the novel suture assembly released from the inserter assembly and in its longitudinally-contracted, radially-expanded second configuration so as to be secured to the bone.
Figure 33:
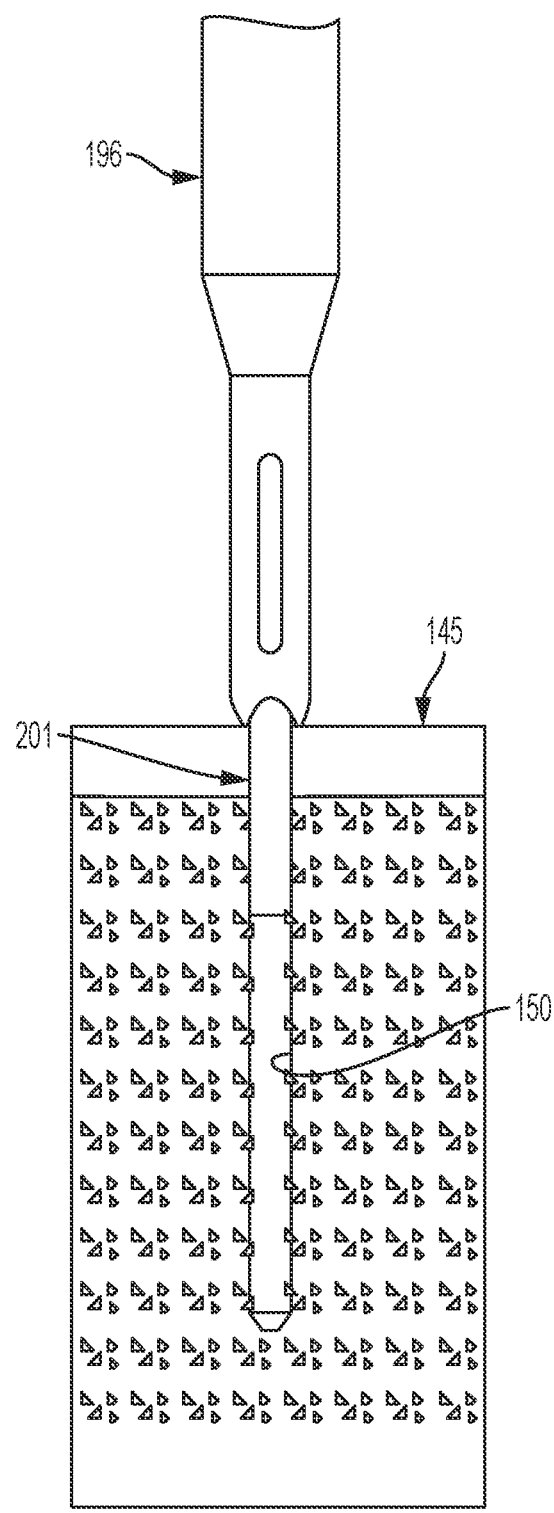
Figure 34:
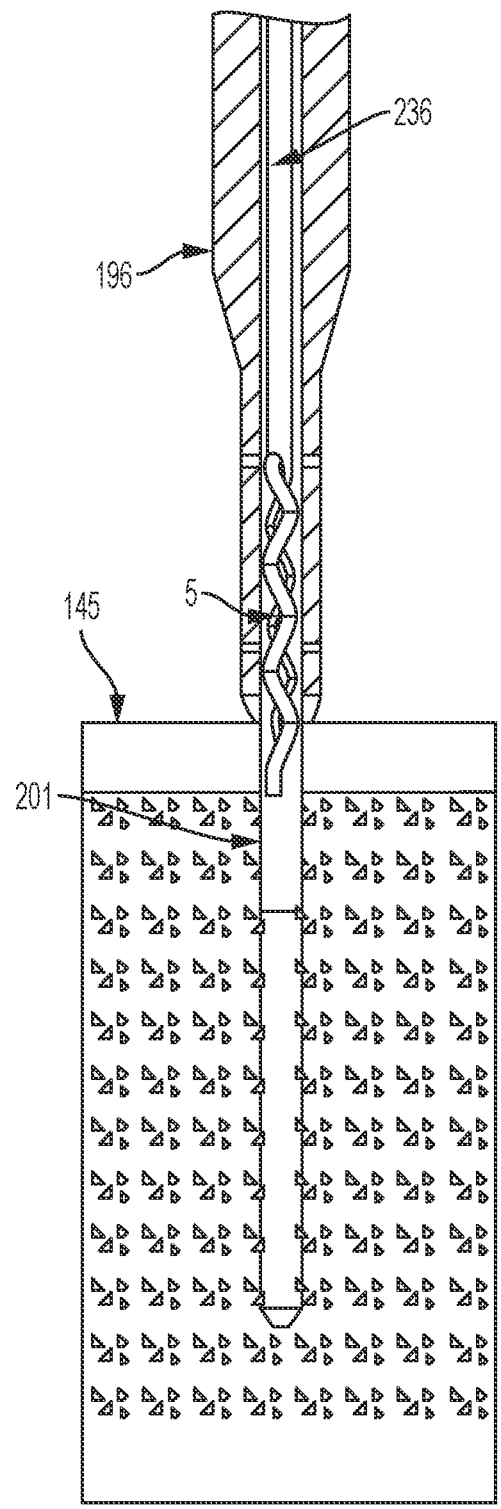
Figure 35:
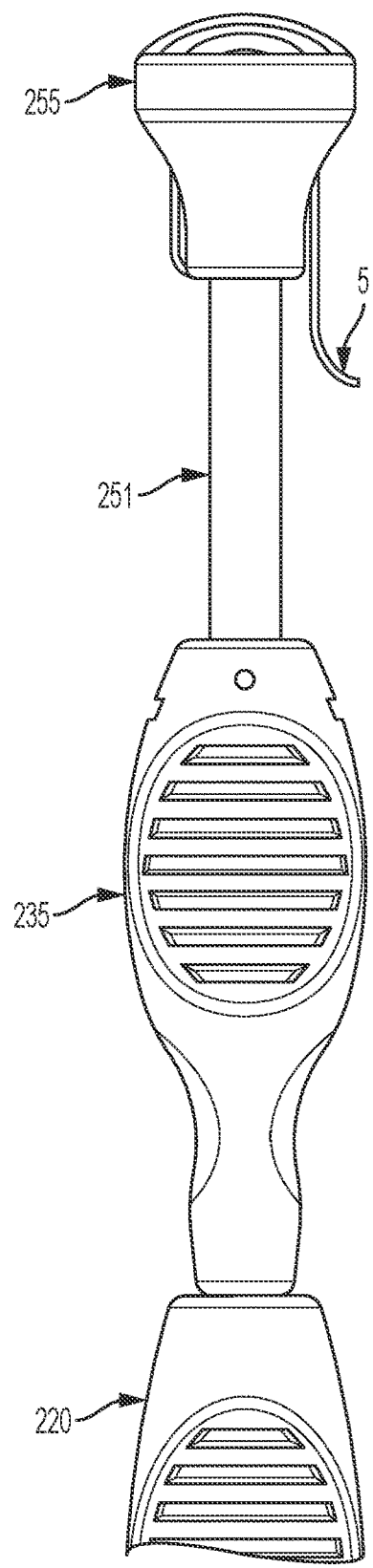
Figure 36:
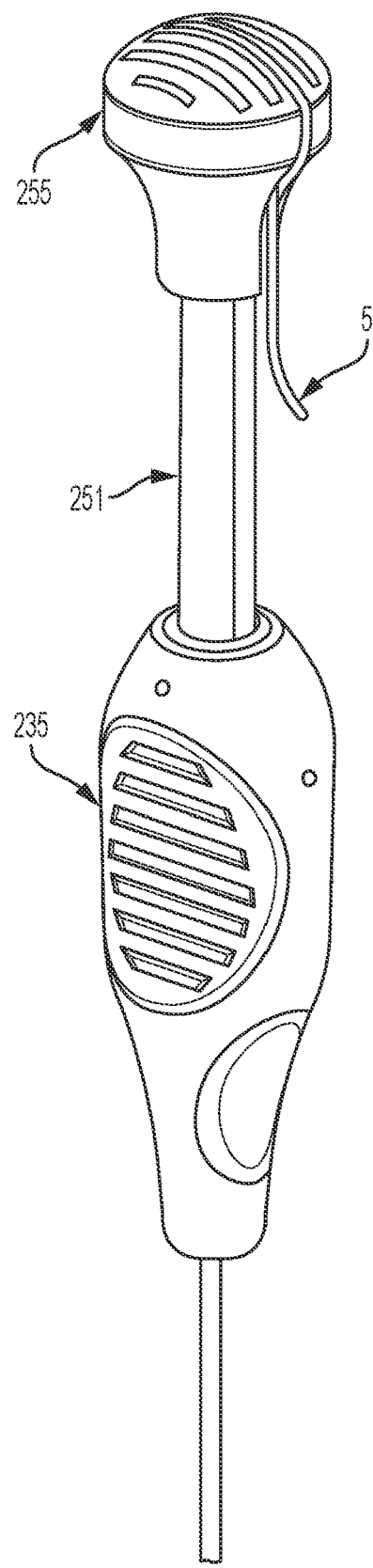
Figure 37:
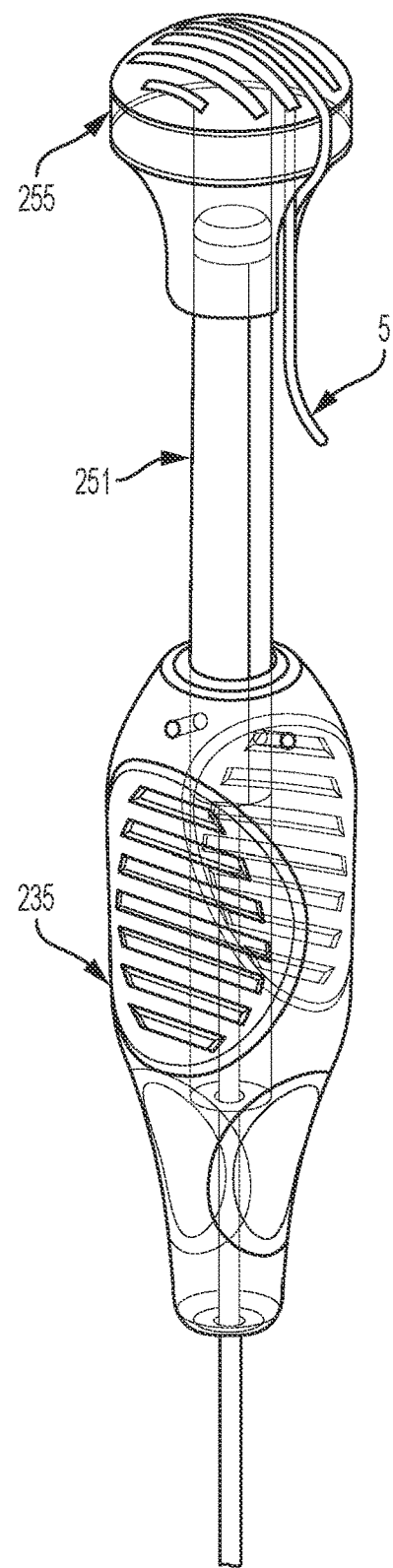
Figure 38:
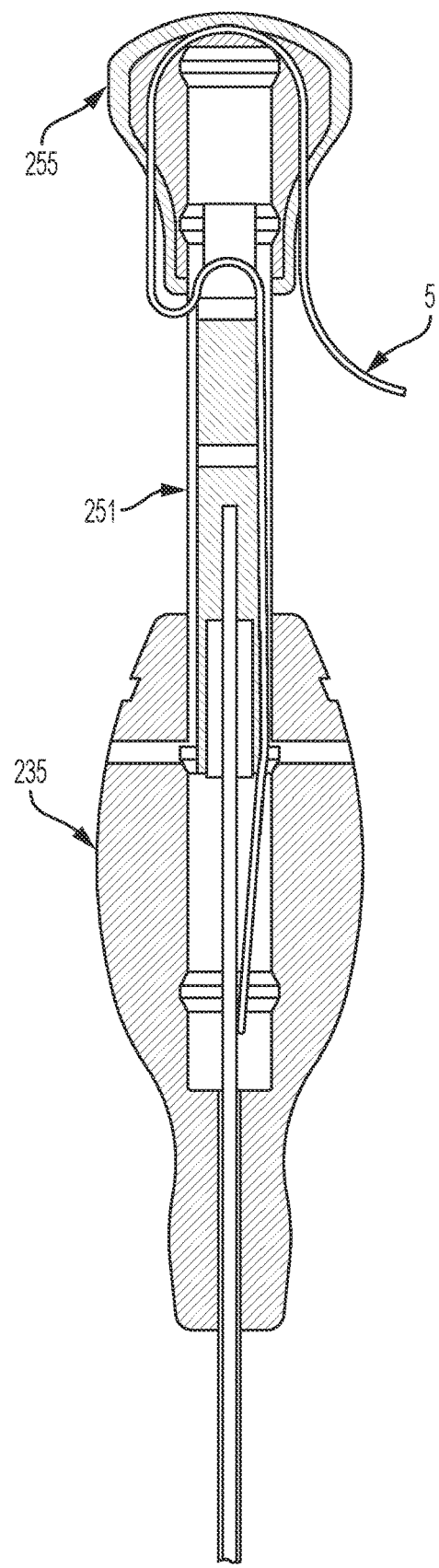
Figure 39:
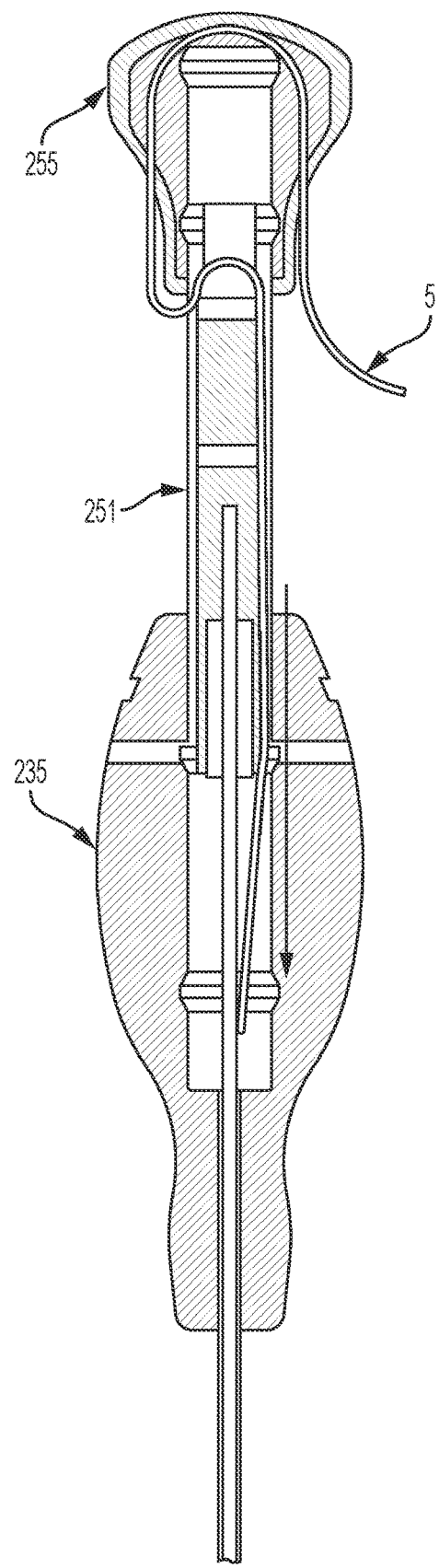
Figure 40:
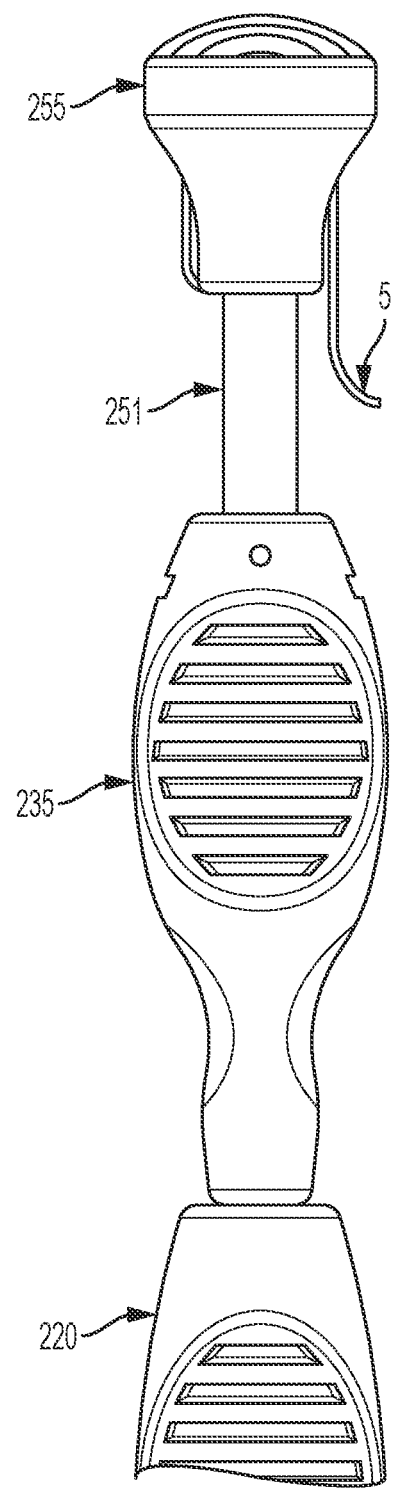

Next, push rod assembly 85 is advanced distally, against bridge 65 of second suture 15, so that novel suture assembly 5 is ejected from the distal end 110 of insertion tube assembly 80 (FIGS. 21 and 22).

Then, with push rod assembly 85 still in position against bridge 65 of second suture 15, first arm 30 and second arm 35 of first suture 10 are tensioned, thereby transforming novel suture assembly 5 from its longitudinally-extended, radially-contracted first configuration into its longitudinally-contracted, radially-expanded second configuration (FIGS. 23 and 24), whereby to expand novel suture assembly 5 laterally into the cancellous region 160 of bone 145.

At this point, inserter assembly 70 and cannulated drill guide assembly 75 are removed from the surgical site (FIG. 25), and first arm 30 and second arm 35 of first suture 10 are tensioned further so as to further laterally expand novel suture assembly 5 and cause the laterally-expanded novel suture assembly to seat against the underside of cortical layer 155 of bone 145 (FIG. 26), whereby to secure the novel suture assembly 5 within bone hole 150 (FIG. 26), with first arm 30 and second arm 35 of first suture 10 extending out of the bone hole.

Again, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), it is possible to form the highly defined, appropriately shaped structure shown in FIGS. 5 and 6 in a highly consistent manner when suture assembly 5 is transformed from its longitudinally-expanded, radially-contracted first configuration (FIGS. 3 and 4) into its longitudinally-contracted, radially-expanded second configuration (FIGS. 5 and 6).

And again, the highly defined, appropriately shaped and consistently reproducible structure shown in FIGS. 5 and 6 is capable of carrying substantial loads without losing its defined shape when loads are applied to the first and second ends 20, 25 of first suture 10. As a result, when suture assembly 5 is inserted into a bone hole while in its longitudinally-expanded, radially contracted first configuration and is thereafter transformed into its longitudinally-contracted, radially-expanded second configuration, novel suture assembly 5 will provide an excellent suture anchor with high holding strength.

In one test configuration, a suture assembly 5 constructed as previously described was delivered into a 2 mm foam bone hole approximately 20-25 mm deep. The media was a 3 mm thick, 55-60 durometer foam bone layer over a 20 durameter foam bone block (Pacific Research Sawbones). The ultimate tensile strength of the suture assembly after insertion into foam bone was approximately 77 pounds. The ultimate tensile strength for another suture assembly after insertion into a 1.5 mm foam bone hole was approximately 50 pounds.

Thereafter, one or both of first arm 30 and second arm 35 of first suture 10 may be used to secure an object (e.g., soft tissue) to the bone. By way of example but not limitation, one or both of first arm 30 and second arm 35 may be passed through a piece of soft tissue (e.g., a ligament) and then tied together so as to secure the soft tissue to the bone.

Again, it should be appreciated that, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), the novel suture assembly 5 does not form a knot in either its longitudinally-expanded, radially-contracted first configuration (FIGS. 3 and 4) or its longitudinally-contracted, radially-expanded second configuration (FIGS. 5 and 6). In either configuration, the novel suture assembly 5 may be disassembled by simply pulling first arm 30 of first suture 10, or by pulling second arm 35 of first suture 10, away from second suture 15, whereby to "undo" the suture assembly. As a result, if at any time it should be desired to remove the novel suture assembly 5 from bone hole 150, first arm 30 of first suture 10, or second arm 35 of first suture 10, is simply pulled away from second suture 15, whereby to "undo" the suture assembly. Once first suture 10 has been pulled clear of the surgical site, second suture 15 may be extracted from bone hole 150 (e.g., with a narrow suture grasper) and removed from the surgical site.

Significantly, the novel suture assembly of the present invention can be sized in accordance with a wide range of anatomical applications. By way of example but not limitation, the novel suture assembly can be formed with relatively fine suture, and with a relatively small number of suture loops, so as to provide a relatively small structure for use with small and delicate anatomical structures. And a novel suture assembly of this type can be delivered through extremely small bone holes, e.g., on the order of 1 mm. Correspondingly, the novel suture assembly can be formed with relatively large suture, and with a relatively large number of suture loops, so as to provide a relatively large structure for use with robust anatomical structures. Significantly, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), it is possible to form the highly defined, appropriately shaped structure shown in FIGS. 5 and 6 in a highly consistent manner when suture assembly 5 is transformed from its longitudinally-expanded, radially-contracted first configuration (FIGS. 3 and 4) into its longitudinally-contracted, radially-expanded second configuration (FIGS. 5 and 6). And, since the highly defined, appropriately shaped and consistently reproducible structure shown in FIGS. 5 and 6 is capable of carrying substantial loads without losing its defined shape when loads are applied to the first and second ends 20, 25 of first suture 10, the suture assembly 5 will provide an excellent suture anchor with high holding strength relative to its size (and relative to the size of the hole made in the host bone).

Furthermore, the novel suture assembly of the present invention can be used to attach objects to structures other than bone, e.g., the novel suture assembly can be used to attach skin to muscle.

Alternative Inserter Assembly for Deploying the Novel Suture Assembly

Looking next at FIGS. 27-31, there is shown an inserter assembly 190 and associated cannulated drill guide assembly 195 which may be used to deploy novel suture assembly 5 in bone. Inserter assembly 190 in turn comprises an insertion tube assembly 200 and a push rod assembly 205.

More particularly, drill guide assembly 195 generally comprises an elongated drill guide tube 196 having a distal end 210 carrying distal end prongs 211, and a proximal end 215 carrying a drill guide handle 220. A lumen 221 extends through elongated drill guide tube 196 and drill guide handle 220.

Figure 3:
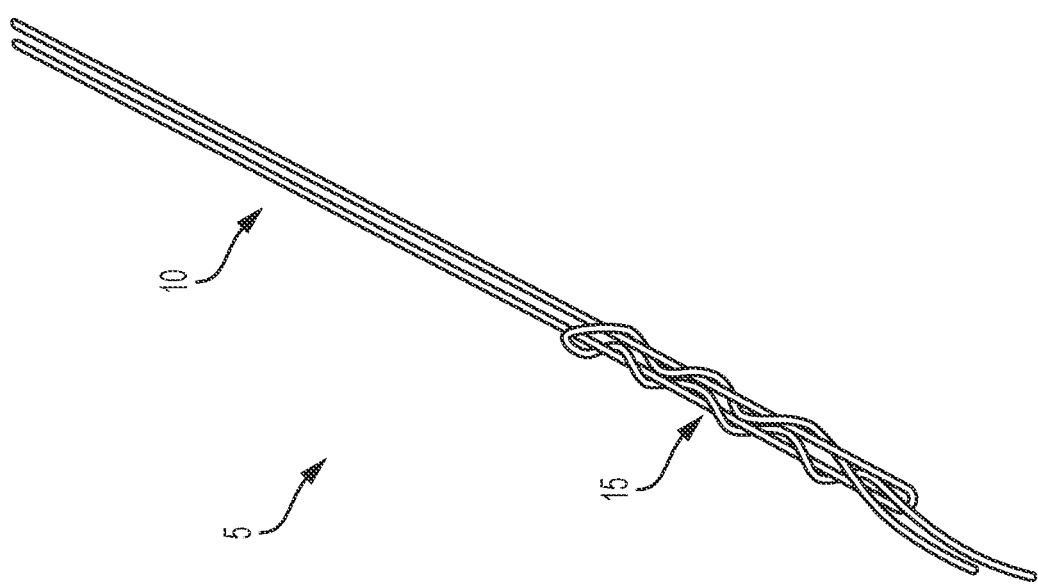
Figure 7:
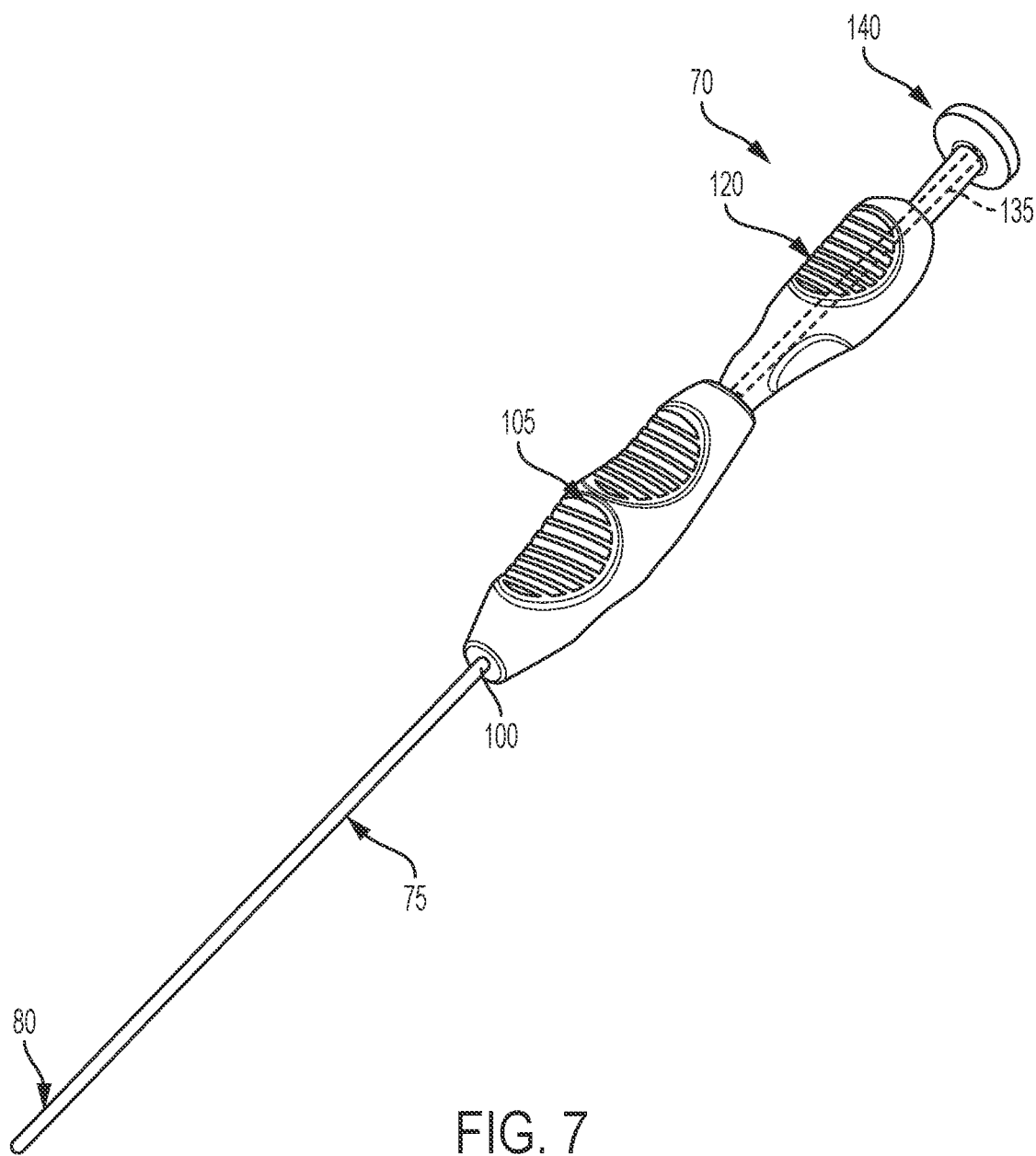
FIG. 7 is a schematic view showing an inserter assembly and associated cannulated drill guide assembly which may be used to deploy the novel suture assembly of FIG. 2 in a bone.
Figure 8:
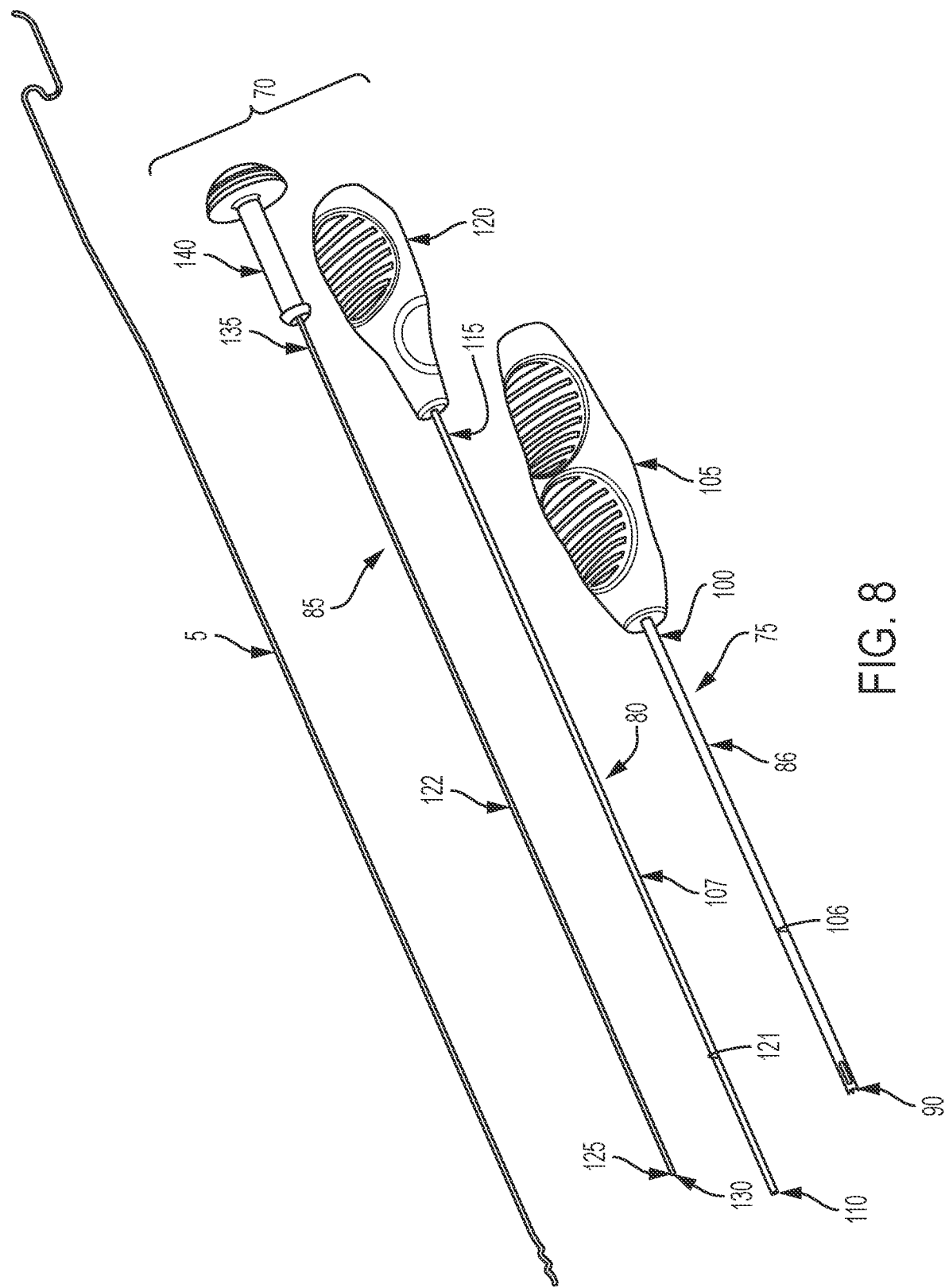
FIGS. 8-11 are schematic views showing various aspects of the inserter assembly and associated cannulated drill guide assembly of FIG. 7, and showing the novel suture assembly of FIG. 2 in its longitudinally-expanded, radially-contracted first configuration and loaded in the inserter assembly.
Figure 9:
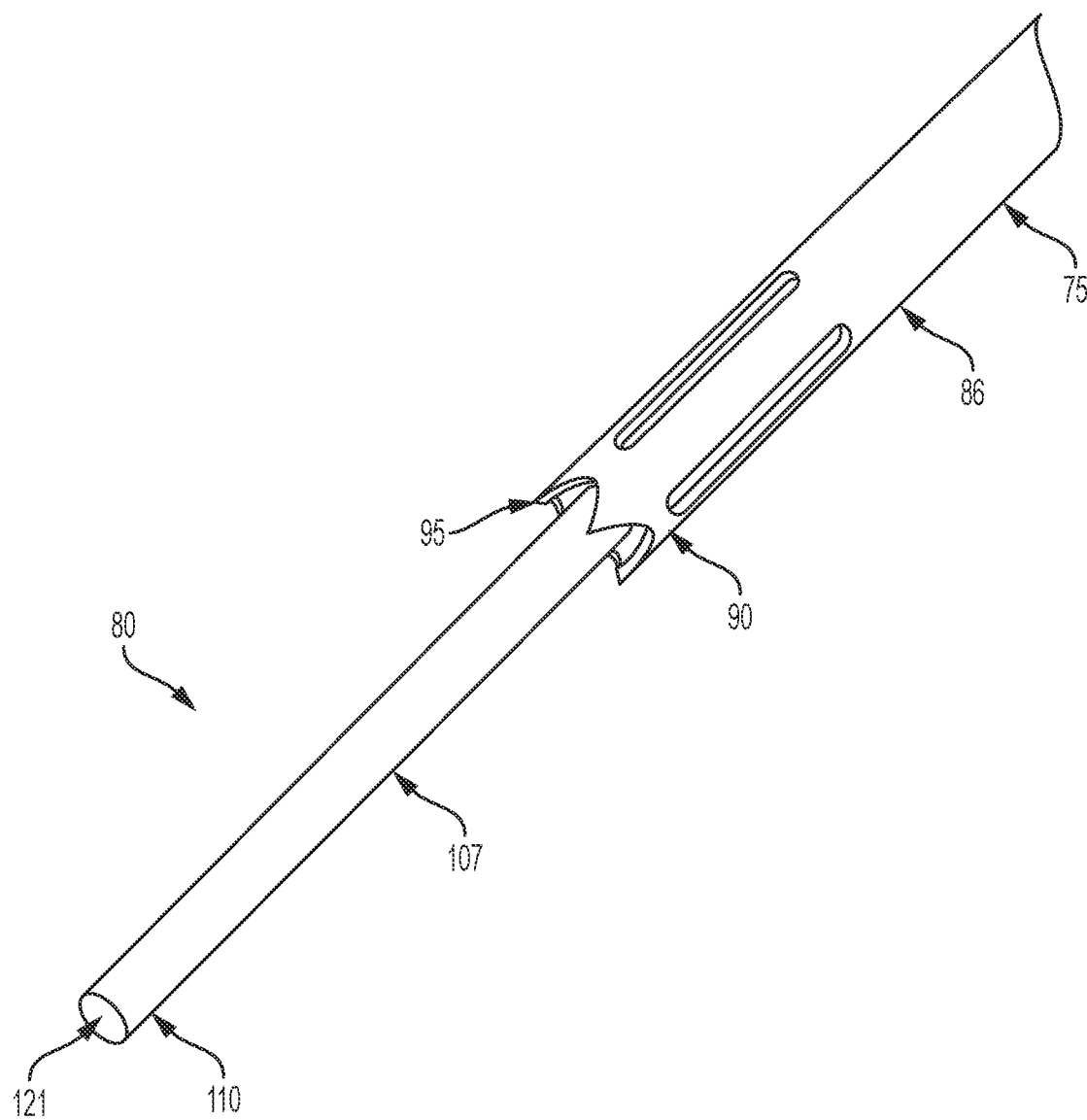
Figure 10:
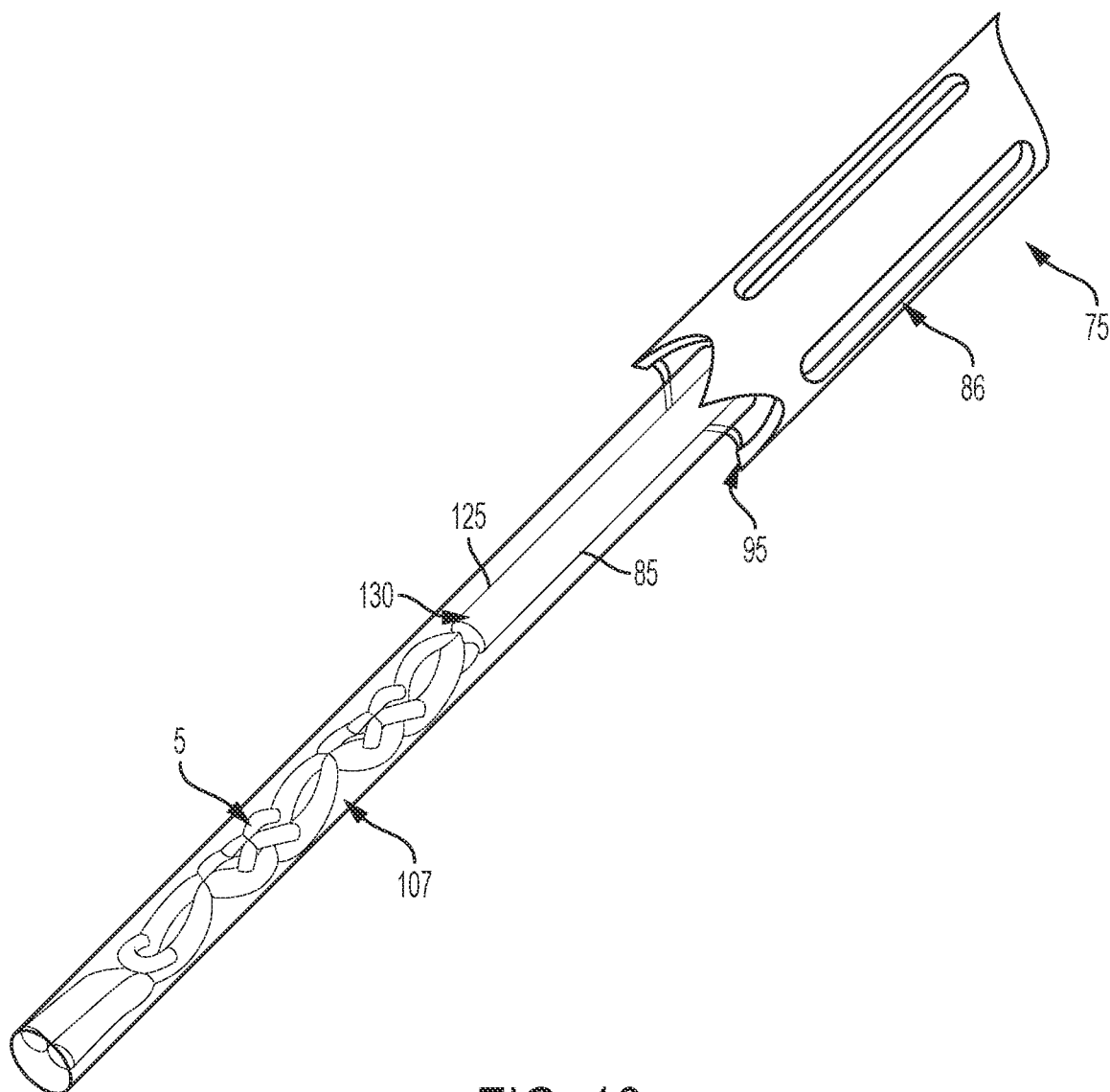
Figure 11:
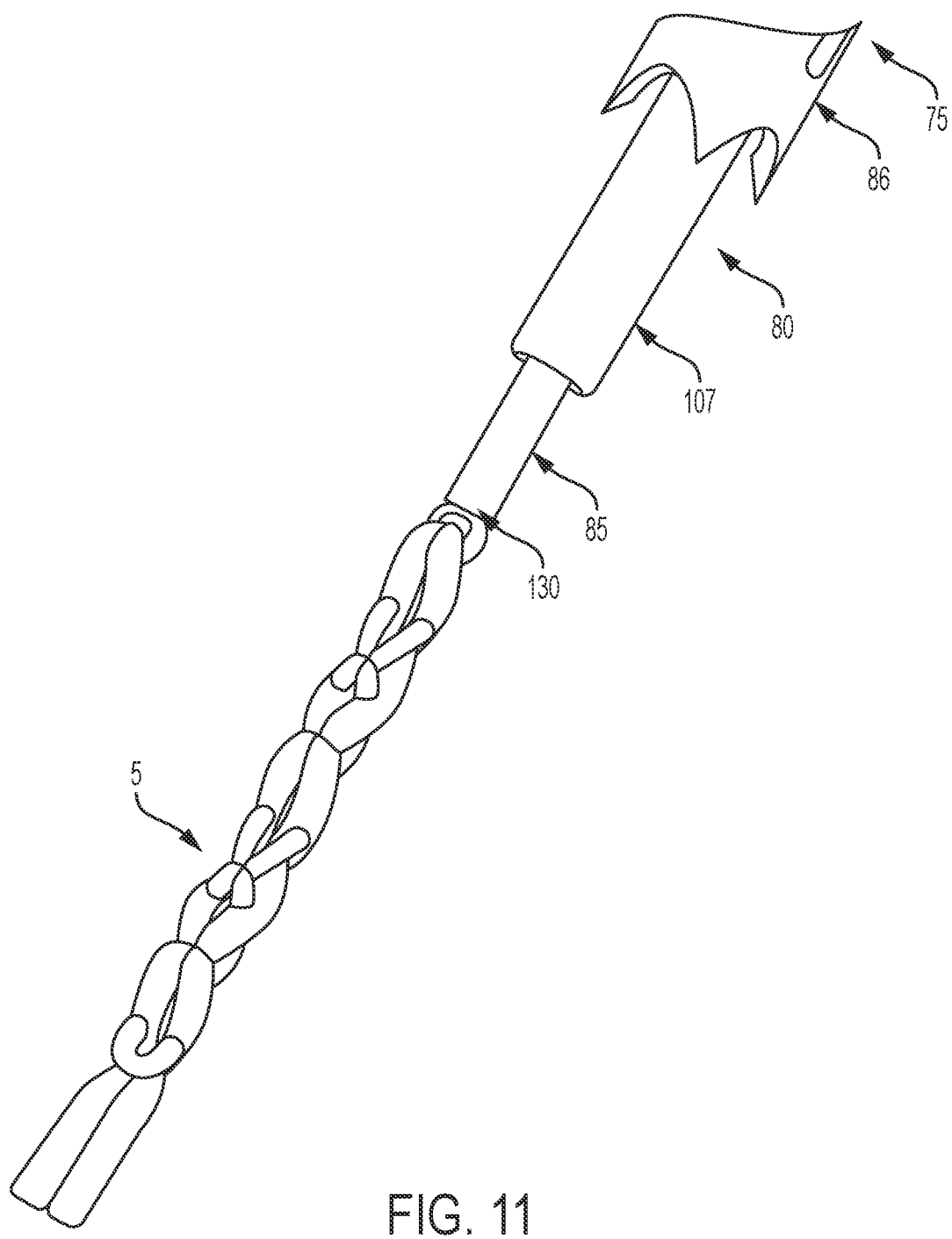
Figure 12:
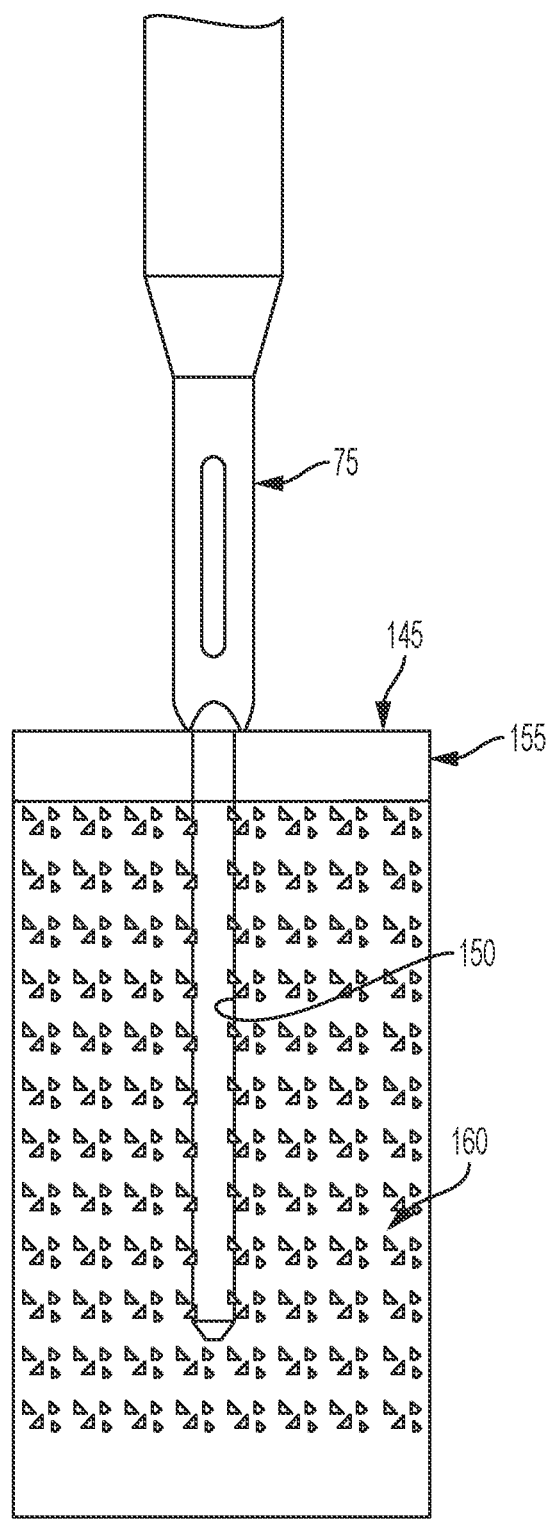
FIGS. 12-18 are schematic views showing one manner in which the inserter assembly and associated cannulated drill guide assembly of FIG. 7 can be used to deploy the novel suture assembly of FIG. 2 in a bone, with FIG. 18 showing the novel suture assembly released from the inserter assembly and in its longitudinally-contracted, radially-expanded second configuration so as to be secured to the bone.

Insertion tube assembly 200 generally comprises an elongated insertion tube 201 having a distal end 225 sized to receive novel suture assembly 5 (either loosely or, more preferably, tightly compressed) when the novel suture assembly is in its aforementioned longitudinally-extended, radially-contracted first configuration (FIGS. 3 and 4). Elongated insertion tube 201 of insertion tube assembly 200 also comprises a proximal end 230 carrying an insertion tube handle 235. A lumen 231 extends through elongated insertion tube 201 and insertion tube handle 235.

Push rod assembly 205 generally comprises a push rod 236 having a distal end 240 terminating in a distal end surface 245, and a proximal end 250 terminating in a push rod slide 251. Push rod slide 251 includes a suture slot 252 and suture saddle 253 which will hereinafter be discussed. A push rod handle 255 is slidably mounted on push rod slide 251 so that the push rod handle is longitudinally movable relative to the push rod slide. A detent mechanism comprising a radial projection 256 on push rod slide 251, which engages a counterpart element 257 on push rod handle 255, keeps push rod handle 255 in position on push rod slide 251 until a force of appropriate magnitude is applied to push rod handle 255, whereupon push rod handle 255 will move relative to push rod slide 251, as will hereinafter be discussed. Push rod handle 255 includes an undersized slot 258 for releasably binding a suture to the push rod handle.

Insertion tube assembly 200 is sized so that its elongated insertion tube 201 can be received within lumen 221 of cannulated drill guide assembly 195 such that, when cannulated drill guide assembly 195 is used to form a hole in a bone, the distal end of insertion tube assembly 200 can be delivered to that hole in a bone, as will hereinafter be discussed.

Push rod assembly 205 is sized so that its push rod 236 can be slidably received within lumen 231 of insertion tube assembly 200 such that, when novel suture assembly 5 is disposed within the distal end 225 of elongated insertion tube 201 of insertion tube assembly 200, advancement of push rod assembly 205 relative to insertion tube assembly 200 will cause novel suture assembly 5 to be ejected from distal end 225 of elongated insertion tube 201 of insertion tube assembly 200, as will hereinafter be discussed. Once novel suture assembly 5 has been ejected from distal end 225 of insertion tube 201 of insertion tube assembly 200, tensioning first arm 30 and second arm 35 of first suture 10, while push rod assembly 205 holds bridge 65 of second suture 15 from moving proximally, will cause novel suture assembly 5 to transform from its longitudinally-elongated, radially-contracted first configuration (FIGS. 3 and 4) into its longitudinally-contracted, radially-expanded second configuration (FIGS. 5 and 6). Such tensioning of first arm 30 and second arm 35 of first suture 10 is applied by moving push rod handle 255 longitudinally along push rod slide 251 (i.e., by applying a force of appropriate magnitude to the aforementioned detent mechanism), as will hereinafter be discussed.

Insertion tube assembly 200 is also sized so that its lumen 231 will accommodate first and second arms 30, 35 of first suture 10 alongside push rod 236 of push rod assembly 205 when push rod 236 is disposed in lumen 231 of insertion tube assembly 200.

Novel suture assembly 5 is intended to be disposed within the distal end of insertion tube assembly 200, distal to push rod assembly 205, with first arm 30 and second arm 35 of first suture 10 extending up lumen 231 of insertion tube assembly 200 (and alongside push rod 236 of push rod assembly 205), along suture slot 252 of push rod slide 251, around suture saddle 253 of push rod slide 251 and then into undersized slot 258 of push rod handle 255, whereby to releasably bind first and second arms 30, 35 of first suture 10 to push rod handle 255. Preferably novel suture assembly 5 is tightly compressed within the distal end of insertion tube assembly 200, so as to provide the largest possible differential between the diameter of the radially-elongated, radially-contracted first configuration (FIGS. 3 and 4) and the longitudinally-contracted, radially-expanded second configuration (FIGS. 5 and 6), whereby to minimize the size of the bone hole and thereby increase holding power in the bone. In this respect it should be appreciated that by winding first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively, it is possible for the first and second sutures 10, 15 to "self-accommodate" within the interior of insertion tube assembly 200, thereby permitting maximum compression of the novel suture assembly within the insertion tube. Furthermore, by leaving first end 45 and second end 50 of second suture 15 free (i.e., unconnected) relative to one another, the first and second sutures 10, 15 can further self-accommodate within the interior of insertion tube assembly 200, thereby permitting maximum compression of the novel suture assembly within the insertion tube assembly. Thus it will be appreciated that, by forming novel suture assembly 5 in the specific manner discussed above, the suture assembly is capable of self-accommodating itself into the smallest possible diameter within the insertion tube assembly, thereby permitting maximum compression of the novel suture assembly within the insertion tube assembly, and hence permitting use of a smaller bone hole and thus providing maximum holding power within the bone.

Significantly, push rod handle 255 is slidably mounted to push rod slide 251 using a detent mechanism, and the first arm 30 and second arm 35 of first suture 10 are releasably secured to push rod handle 255 after first passing over suture saddle 253 of push rod slide 251, such that (i) by initially applying a force to push rod handle 255 which is below the trigger magnitude of the aforementioned detent mechanism, push rod handle 255 will initially cause push rod assembly 205 to be moved distally relative to insertion tube assembly 200, whereby to eject suture assembly 205 from insertion tube assembly 200, and (ii) by thereafter applying a force to push rod handle 255 which is above the trigger magnitude of the aforementioned detent mechanism, push rod handle 255 will thereafter move relative to push rod slide 251, whereby to cause tension to be applied to first arm 30 and second arm 35 of first suture 10 without causing further distal motion of push rod 236.

Thus, with this form of the invention, once novel suture assembly 5 has been ejected from distal end 225 of insertion tube assembly 200, first arm 30 and second arm 35 of first suture 10 are automatically tensioned, while push rod assembly 205 holds bridge 65 of second suture 15 from moving proximally, whereby to cause novel suture assembly 5 to transform from its longitudinally-elongated, radially-contracted first configuration (FIGS. 3 and 4) into its longitudinally-contracted, radially-expanded second configuration (FIGS. 5 and 6).

In essence, in this form of the invention, progressive distal movement of push rod handle 255 causes novel suture assembly 5 to first be ejected into a bone hole and then transformed from its longitudinally-elongated, radially-contracted first configuration into its longitudinally-contracted, radially-expanded second configuration.

Using the Alternative Inserter Assembly for Deploying the Novel Suture Assembly, in Order to Secure an Object to Bone The alternative inserter assembly 190 shown in FIGS. 27-31 and its associated cannulated drill guide assembly 195 may be used to deploy novel suture assembly 5 in bone, in order to secure an object to bone.

Thus, in another preferred form of the present invention, and looking now at FIGS. 32-49, the distal end of cannulated drill guide assembly 195 is first placed against the surface of bone 145, then a bone drill (not shown) of the sort well known in the art is advanced through lumen 221 of the cannulated drill guide assembly and into the bone so that a bone hole 150 of appropriate size (diameter and depth) is formed in the bone, then the bone drill is removed from lumen 221 of cannulated drill guide assembly 195 while leaving the cannulated drill guide assembly in position against bone 145, and then the distal end 225 of insertion tube assembly 200, carrying novel repair contruct 5 therein, is advanced through cannulated drill guide assembly 195 and into bone hole 150 formed in bone 145 (FIGS. 32-38). It will be appreciated that push rod 236 of push rod assembly 205 is already disposed within lumen 231 of insertion tube assembly 200 as this occurs, with distal end 240 of push rod assembly 205 sitting against bridge 65 of second suture 15.

Figure 41:
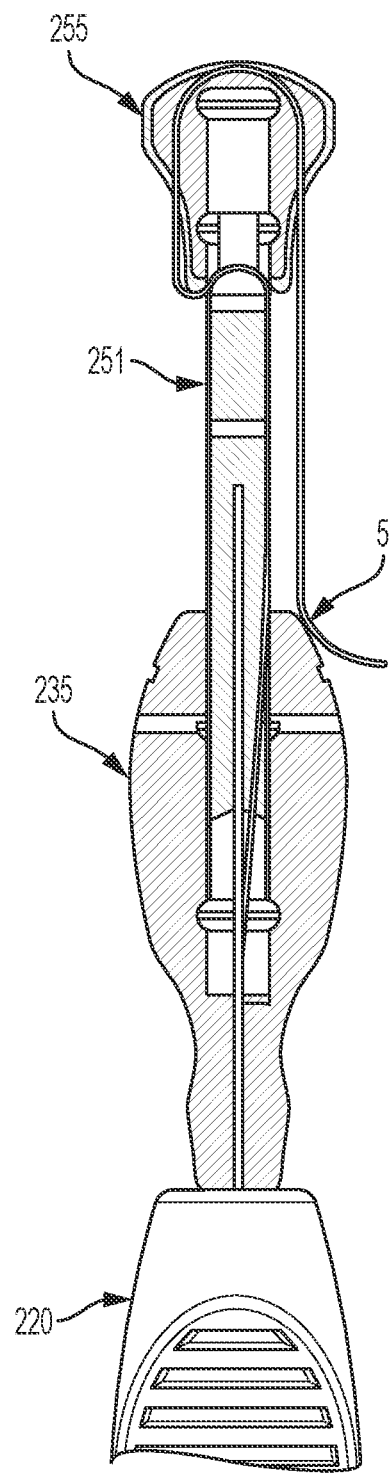
Figure 42:
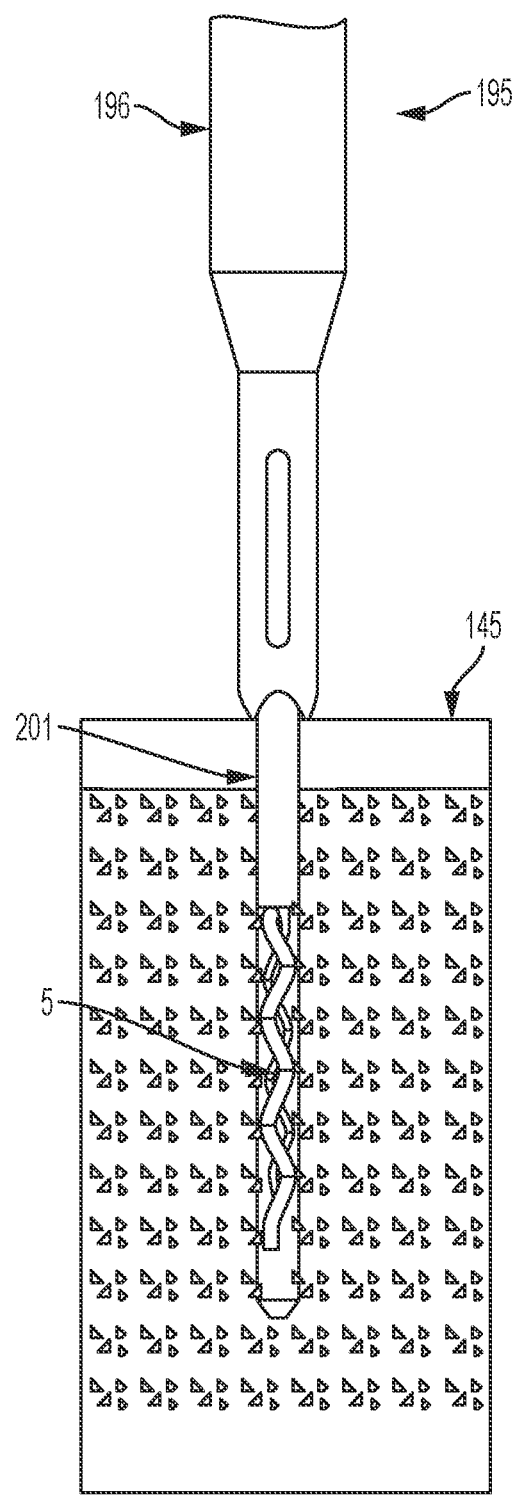
Figure 43:
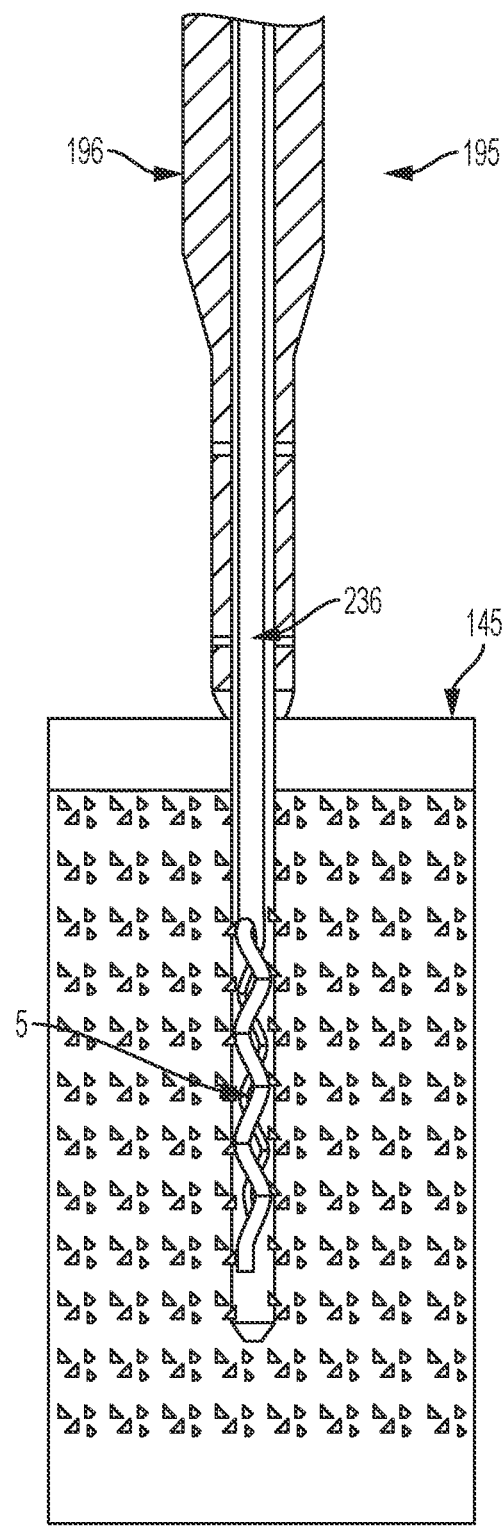
Figure 44:
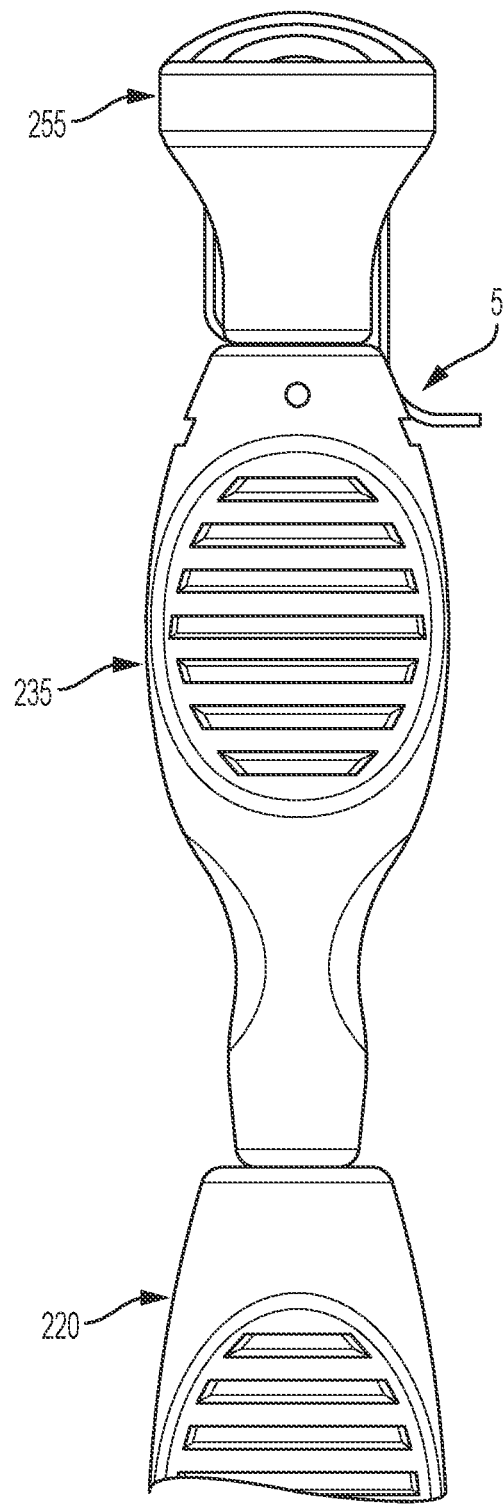
Figure 45:
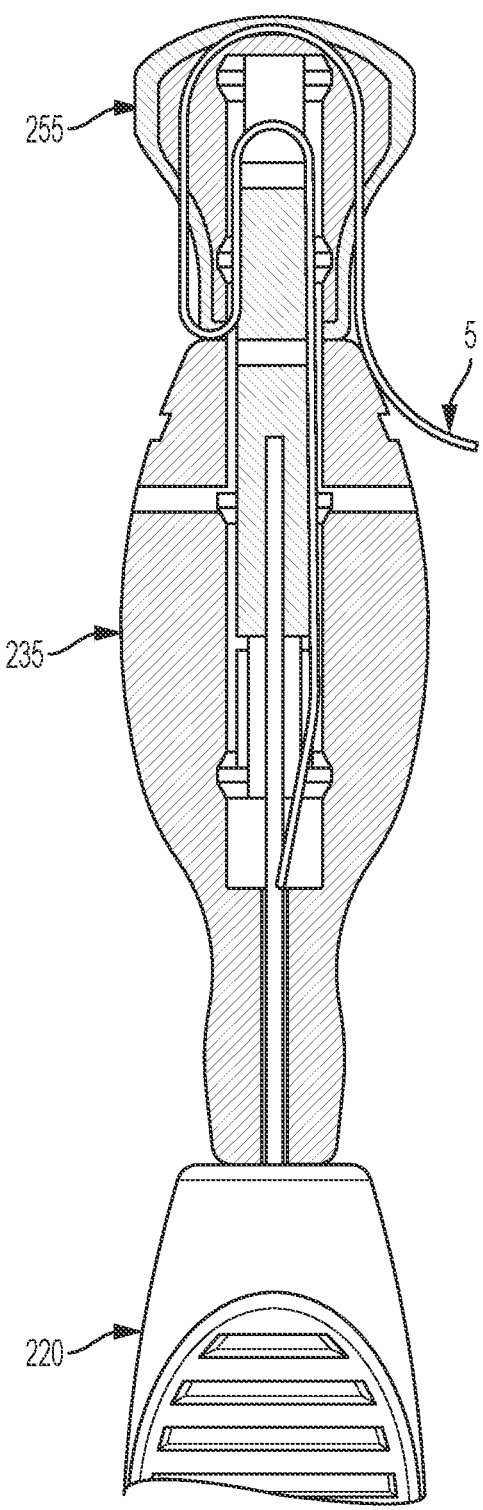
Figure 46:
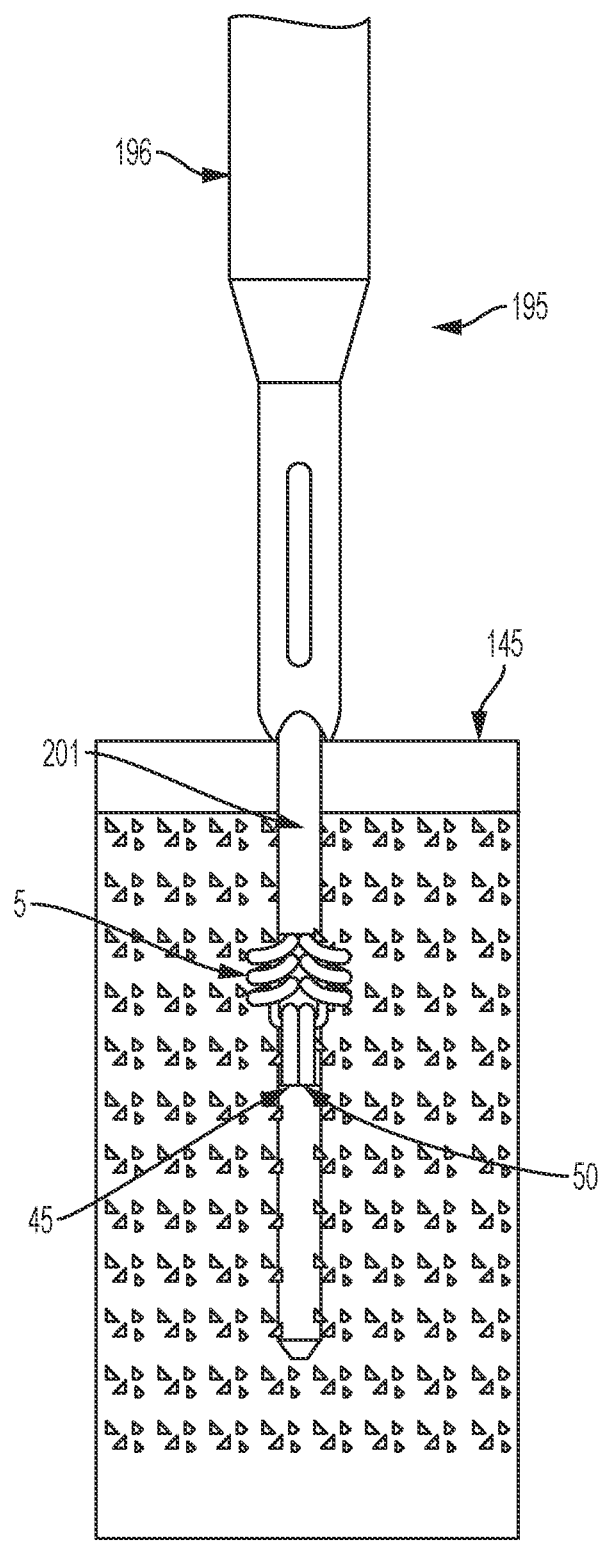
Figure 47:
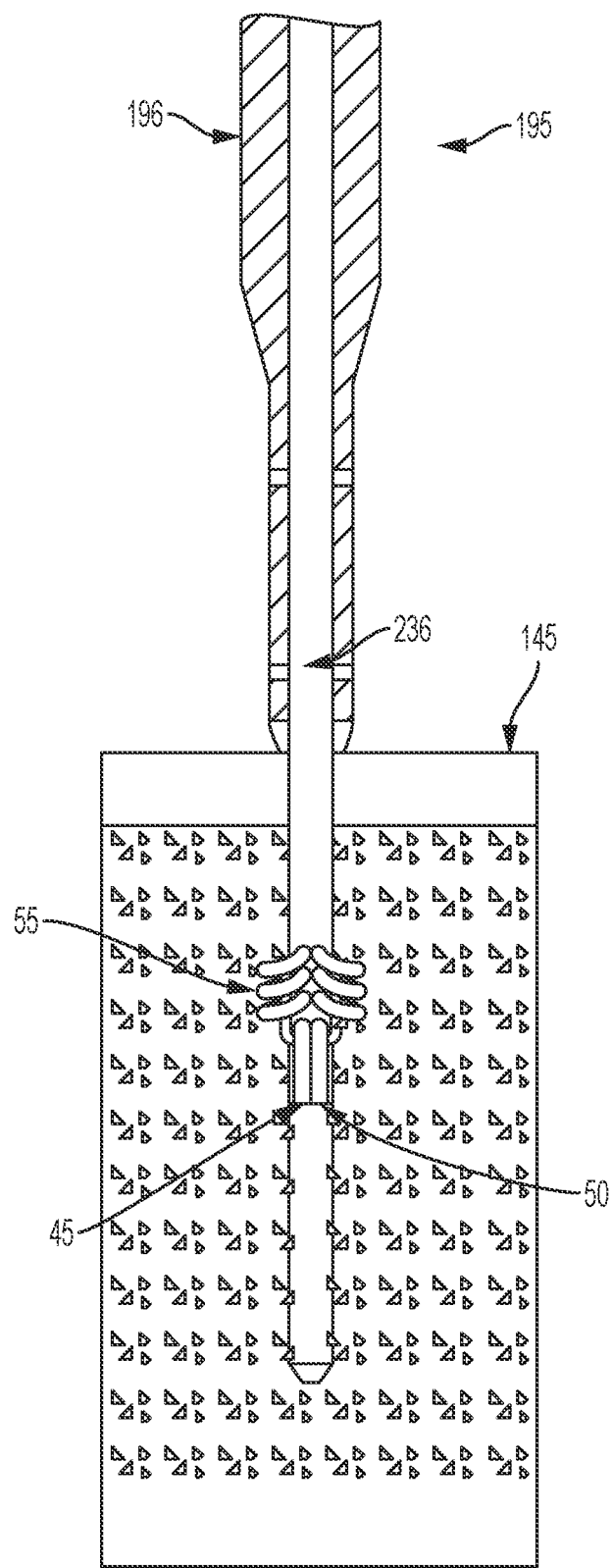
Figure 48:
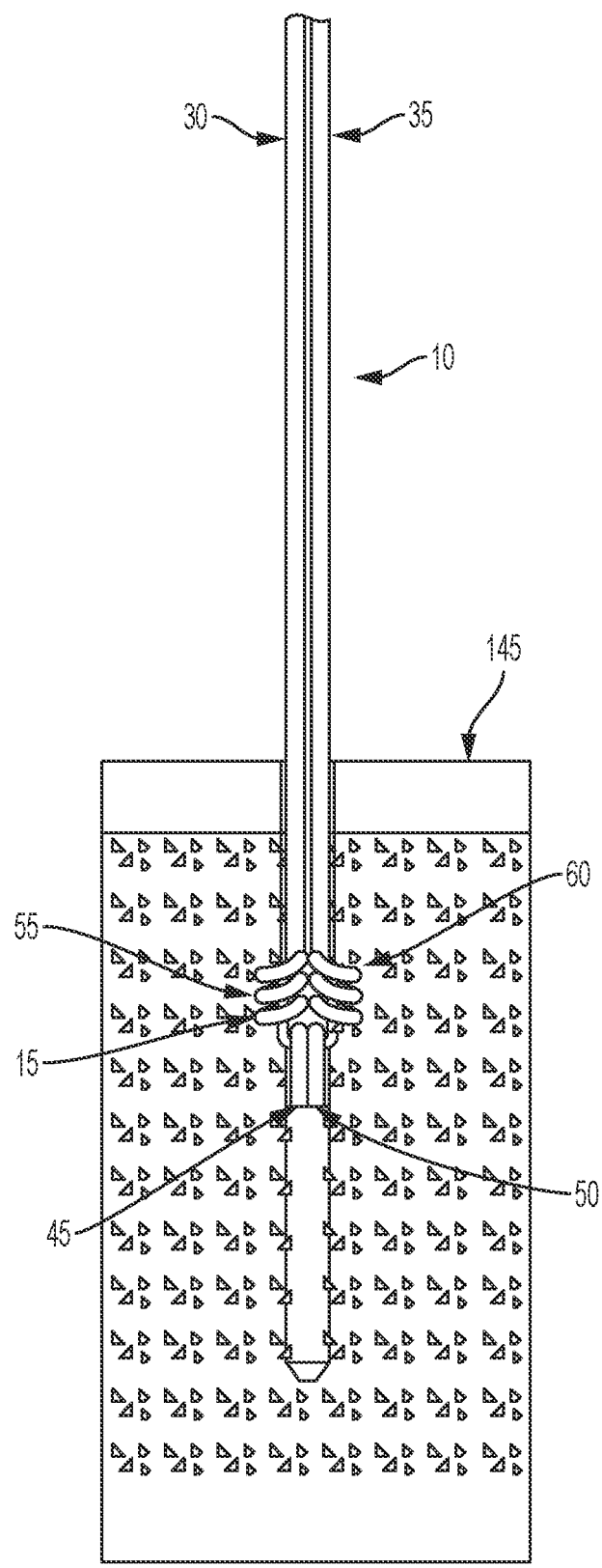
Figure 49:
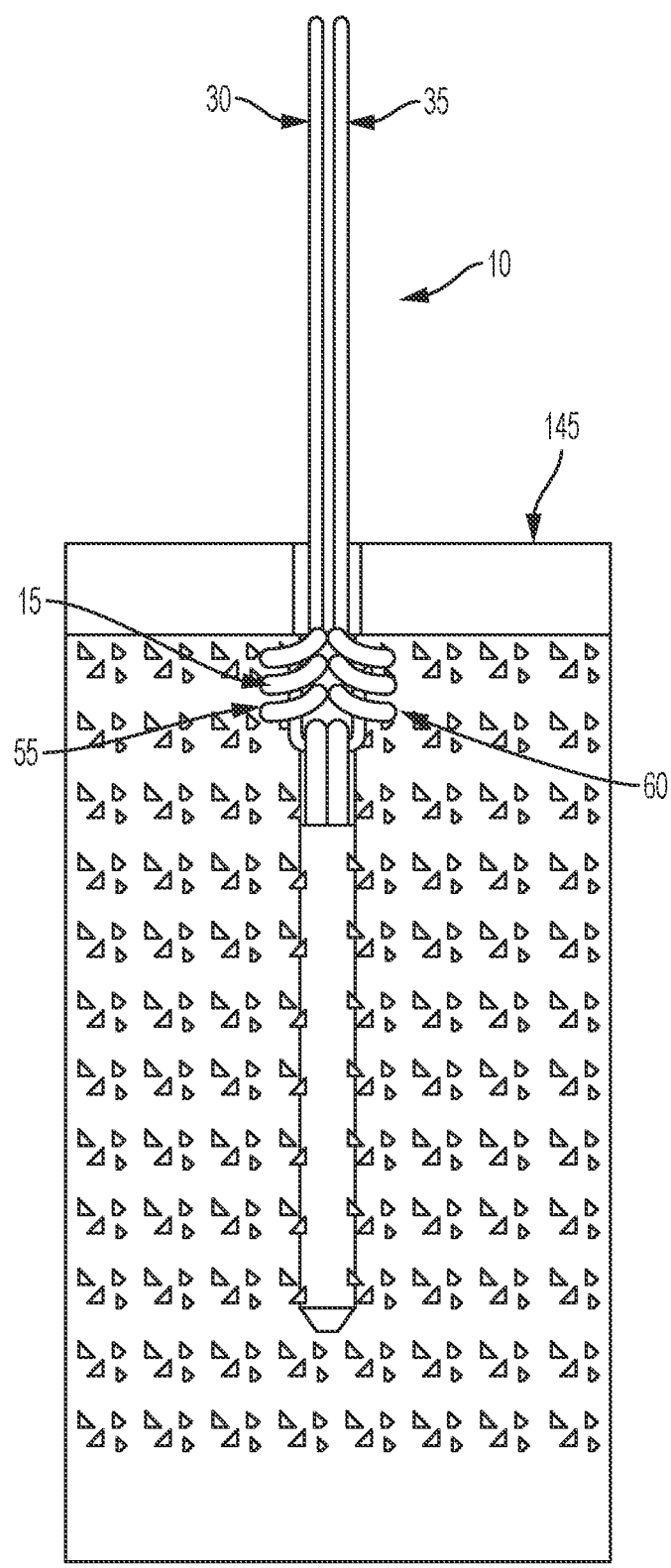

Next, push rod assembly 205 is advanced distally, against bridge 65 of second suture 15, so that novel suture assembly 5 is ejected from the distal end 225 of insertion tube assembly 200 (FIGS. 39-43). This is done by pressing push rod handle 255 distally so that push rod assembly 205 advances distally relative to insertion tube 200. As this occurs, push rod handle 255 remains fixed in position on push rod slide 251 due to the detent mechanism of radial projection 256 on push rod slide 251 and counterpart element 257 on push rod handle 255. Push rod assembly 205 advances distally until push rod slide 251 bottoms out in its seat on insertion tube handle 235 (FIG. 41).

Then, with push rod assembly 205 still in position against bridge 65 of second suture 15, first arm 30 and second arm 35 of first suture 10 are tensioned, thereby transforming novel suture assembly 5 from its longitudinally-extended, radially-contracted first configuration into its longitudinally-contracted, radially-expanded second configuration (FIGS. 44-47), whereby to expand novel suture assembly 5 laterally into the cancellous region 160 of bone 145. This is done by pressing push rod handle 255 further distally so that push rod handle 255 overcomes the aforementioned detent mechanism with push rod slide 251, thereby causing push rod handle 255 to move distally along push rod slide 251, relative to insertion tube assembly 200 and push rod assembly 205. As this occurs, the first and second arms 30, 35 of first suture 10 are tensioned, due to the increasing length of the suture path created around suture saddle 253.

At this point, first arm 30, 35 of first suture 10 are released from inserter assembly 190 (e.g., by dismounting the suture arms from undersized slot 258 of push rod handle 255), inserter assembly 190 is removed from the surgical site (FIG. 48), and then first arm 30 and second arm 35 of first suture 10 are tensioned further so as to further laterally expand novel suture assembly 5 and cause the laterally-expanded novel suture assembly to seat against the underside of cortical layer 155 of bone 145 (FIG. 49), whereby to secure the novel suture assembly 5 within bone hole 150, with first arm 30 and second arm 35 of first suture 10 extending out of the bone hole.

Significantly, by forming novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), it is possible to form the highly defined, appropriately shaped structure shown in FIGS. 5 and 6 in a highly consistent manner when suture assembly 5 is transformed from its longitudinally-expanded, radially-contracted first configuration (FIGS. 3 and 4) into its longitudinally-contracted, radially-expanded second configuration (FIGS. 5 and 6).

And significantly, the highly defined, appropriately shaped and consistently reproducible structure shown in FIGS. 5 and 6 is capable of carrying substantial loads without losing its defined shape when loads are applied to the first and second ends 20, 25 of first suture 10. As a result, when suture assembly 5 is inserted into a bone hole while in its longitudinally-expanded, radially-contracted first configuration and is thereafter transformed into its longitudinally-contracted, radially-expanded second configuration, novel suture assembly 5 will provide an excellent suture anchor with high holding strength.

Thereafter, one or both of first arm 30 and second arm 35 of first suture 10 may be used to secure an object (e.g., soft tissue) to the bone. By way of example but not limitation, one or both of first arm 30 and second arm 35 may be passed through a piece of soft tissue (e.g., a ligament) and then tied together so as to secure the soft tissue to bone.

Again, it should be appreciated that, by forming the novel suture assembly 5 in the manner previously described (e.g., by wrapping first arm 55 of second suture 15 around first arm 30 of first suture 10, and by wrapping second arm 60 of second suture 15 around second arm 35 of first suture 10, with first arm 55 and second arm 60 being wound in opposite directions on first arm 30 and second arm 35, respectively), the novel suture assembly 5 does not form a knot in either its longitudinally-expanded, radially-contracted first configuration (FIGS. 3 and 4) or its longitudinally-contracted, radially-expanded second configuration (FIGS. 5 and 6). In either configuration, the novel suture assembly 5 may be disassembled by simply pulling first arm 30 of first suture 10, or by pulling second arm 35 of first suture 10, away from second suture 15, whereby to "undo" the suture assembly. As a result, if at any time it should be desired to remove the novel suture assembly 5 from bone hole 150, first arm 30 of first suture 10, or second arm 35 of first suture 10, is simply pulled away from second suture 15, whereby to "undo" the suture assembly. Once first suture 10 has been pulled clear of the surgical site, second suture 15 may be extracted from bone hole 150 (e.g., with a narrow suture grasper) and removed from the surgical site.

Significantly, since the novel suture assembly 5 is a relatively flexible structure while it is in its aforementioned longitudinally-elongated, radially-contracted first configuration, it is capable of conforming to some extent to the geometry of the bone hole in which it is received as it is ejected from insertion tube assembly 200 and before it is transformed into its longitudinally-contracted, radially-expanded second configuration. As a result, the novel suture assembly 5 can be deployed in relatively shallow bone holes, since it is relatively pliable when it is in its longitudinally-elongated, injection-state configuration and before it is transformed into its longitudinally-contracted, anchoring-state configuration.

Alternative Forms of the Novel Suture Assembly

FIG. 2 shows the preferred manner of forming novel suture assembly 5.

Figure 50:
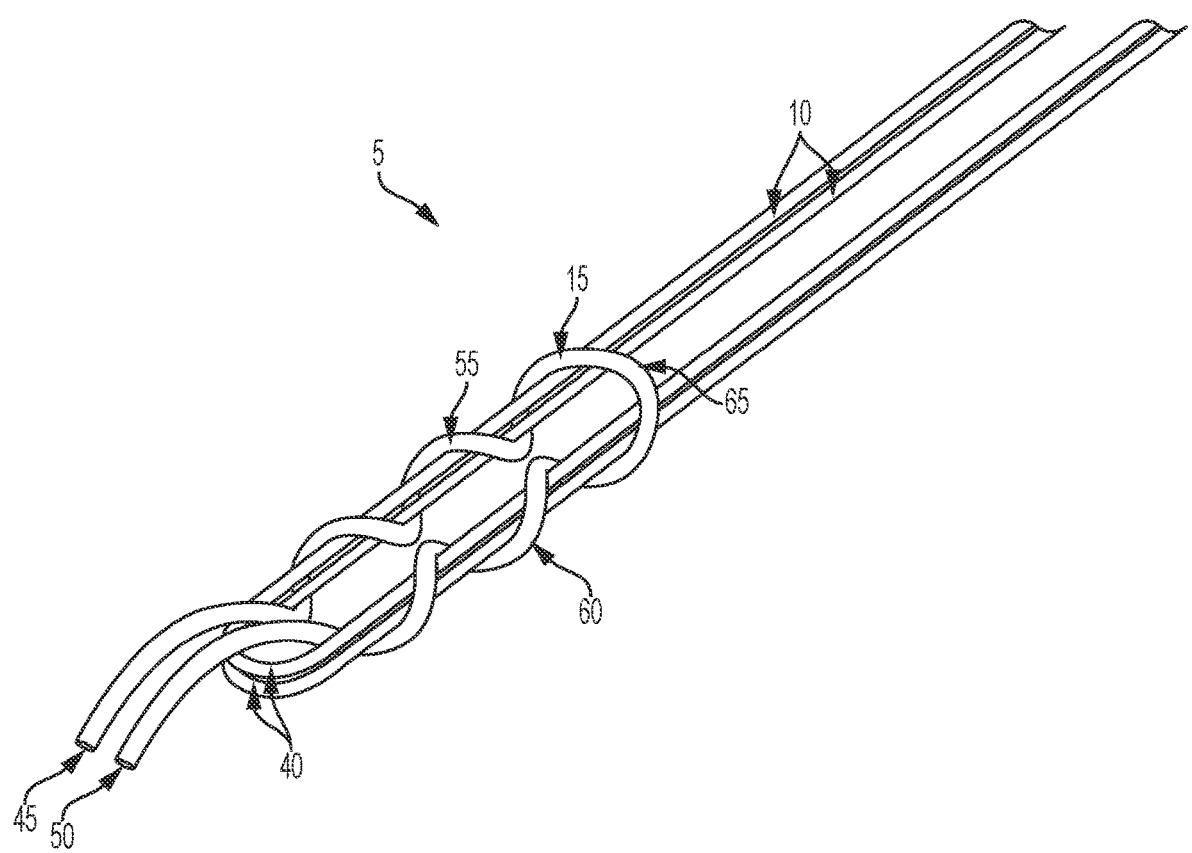
FIGS. 50-54 are schematic views showing alternative forms of the novel suture assembly of FIG. 2.

FIG. 50 shows an alternative manner of forming novel suture assembly 5. In this form of the invention, suture assembly 5 is substantially the same as the suture assembly shown in FIG. 2, except that two first sutures 10, disposed in a parallel arrangement, are provided. This construction can be highly advantageous in some situations since it provides four strands of suture emerging from the bone hole.

Figure 51:
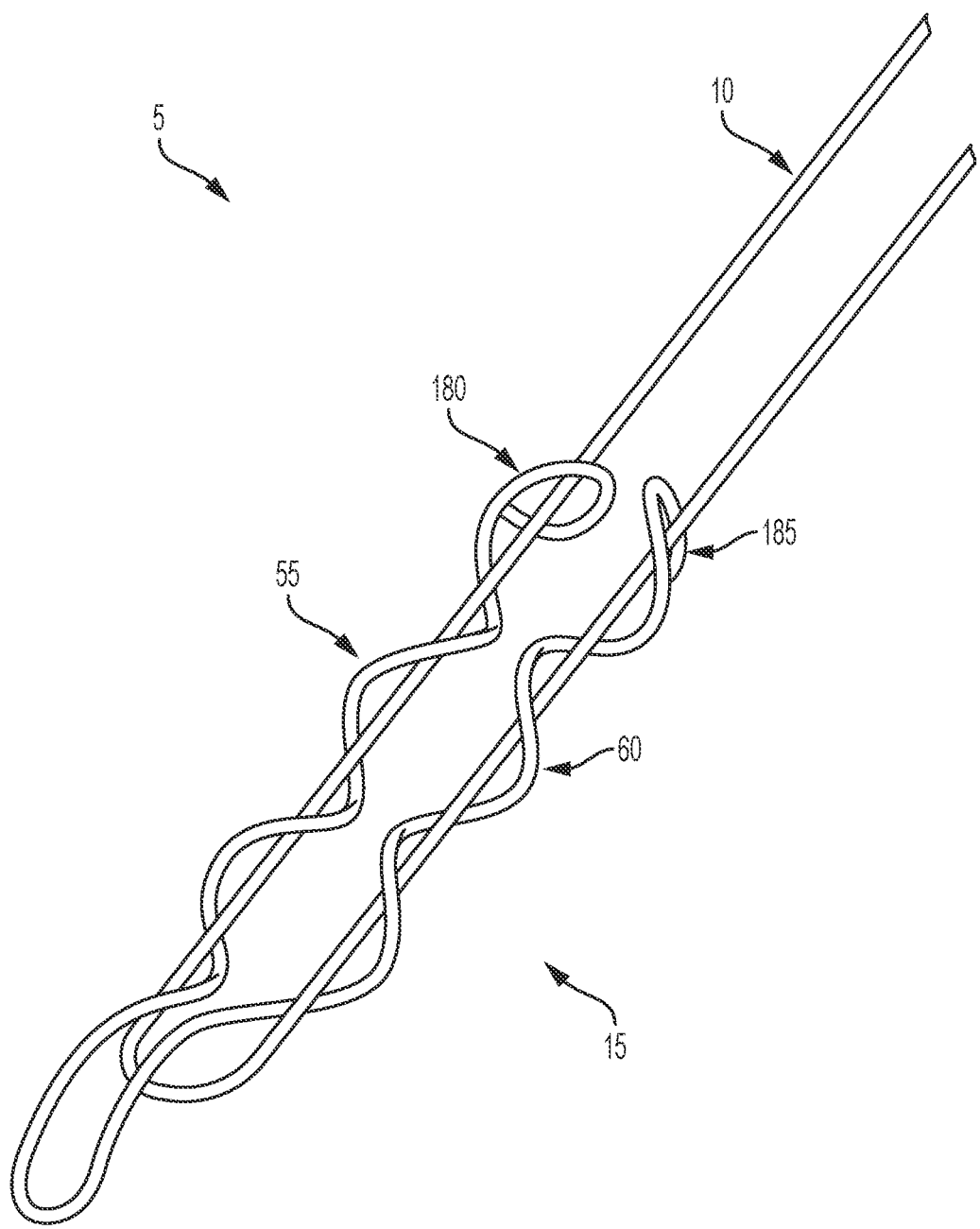

FIG. 51 shows another manner of forming the novel suture construct 5. In this form of the invention, second suture 15 has an eyelet 180 formed on the end of first arm 55 and an eyelet 185 formed on the end of second arm 60. First arm 55 of second suture 15 is wrapped (e.g., three times) around first arm 30 of first suture 10, with first arm 30 of first suture 10 passing through eyelet 180 of second suture 15, and second arm 60 of second suture 15 is wrapped (e.g., three times) around second arm 35 of first suture 10, with second arm 35 of first suture 10 passing through eyelet 185 of second suture 15. Again, first arm 55 of second suture 15 is wrapped in the opposite direction from second arm 60 of second suture 15. In this form of the invention, bridge 65 of second suture 15 may be positioned close to, and extend substantially parallel to, bridge 40 of first suture 10. While this form of the invention may permit enhanced compression of the novel suture assembly within the insertion tube, it is generally not preferred since it presents separate eyelets 180, 185 to the distal end of the push rod assembly, rather than an integrated bridge 65, and can be more difficult to reliably engage with the distal end of the push rod assembly.

Figure 52:
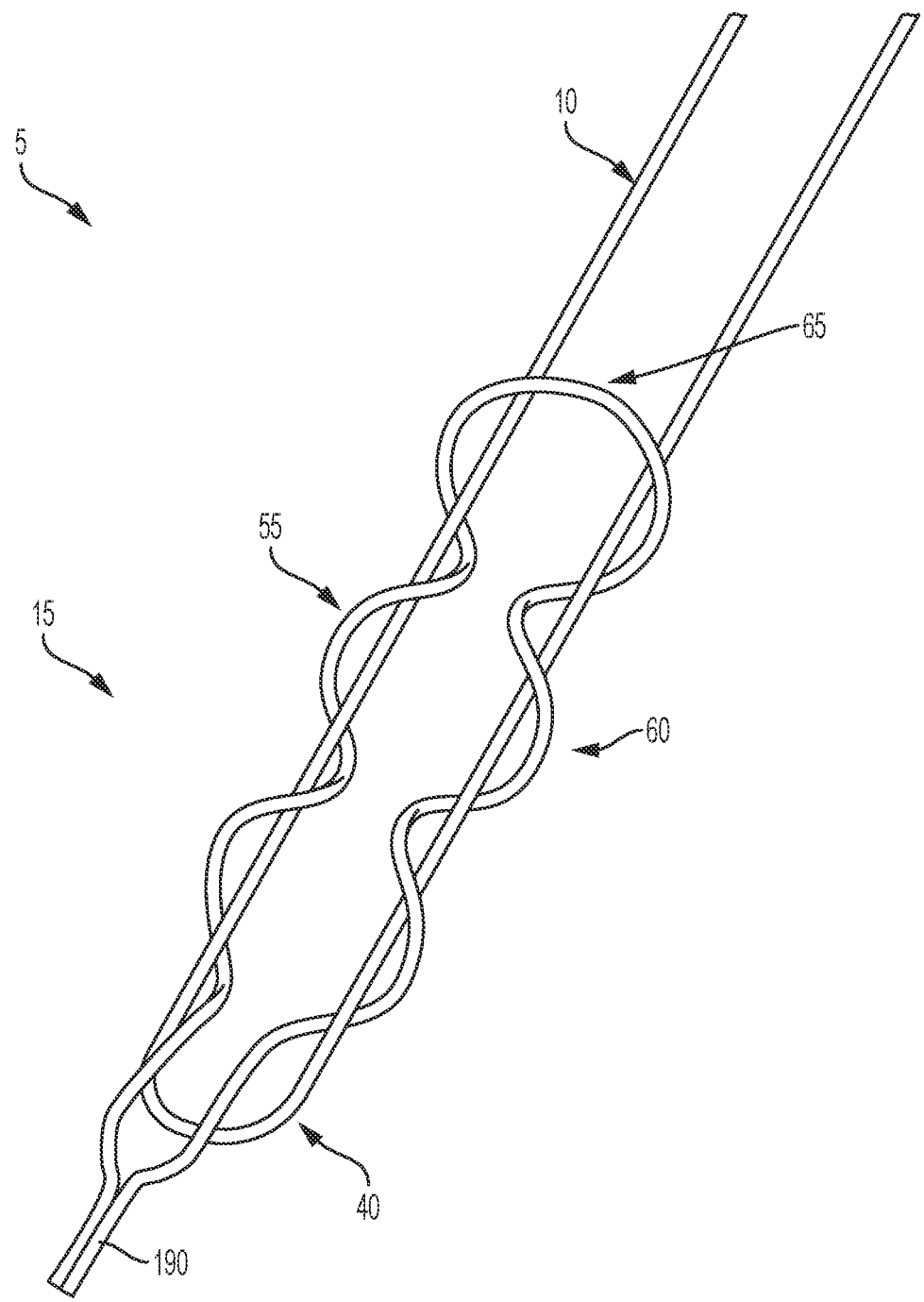
Figure 53:
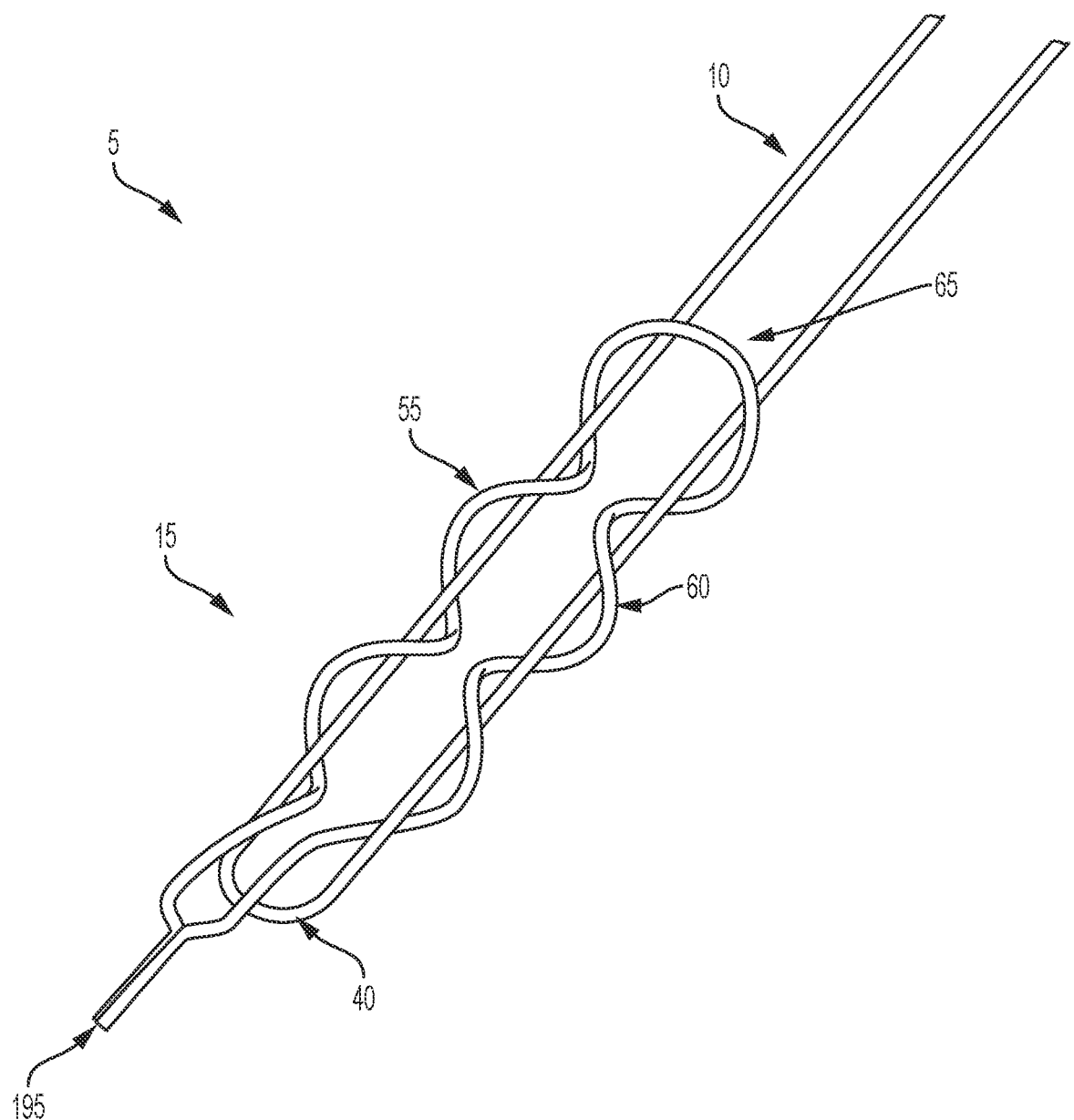
Figure 54:
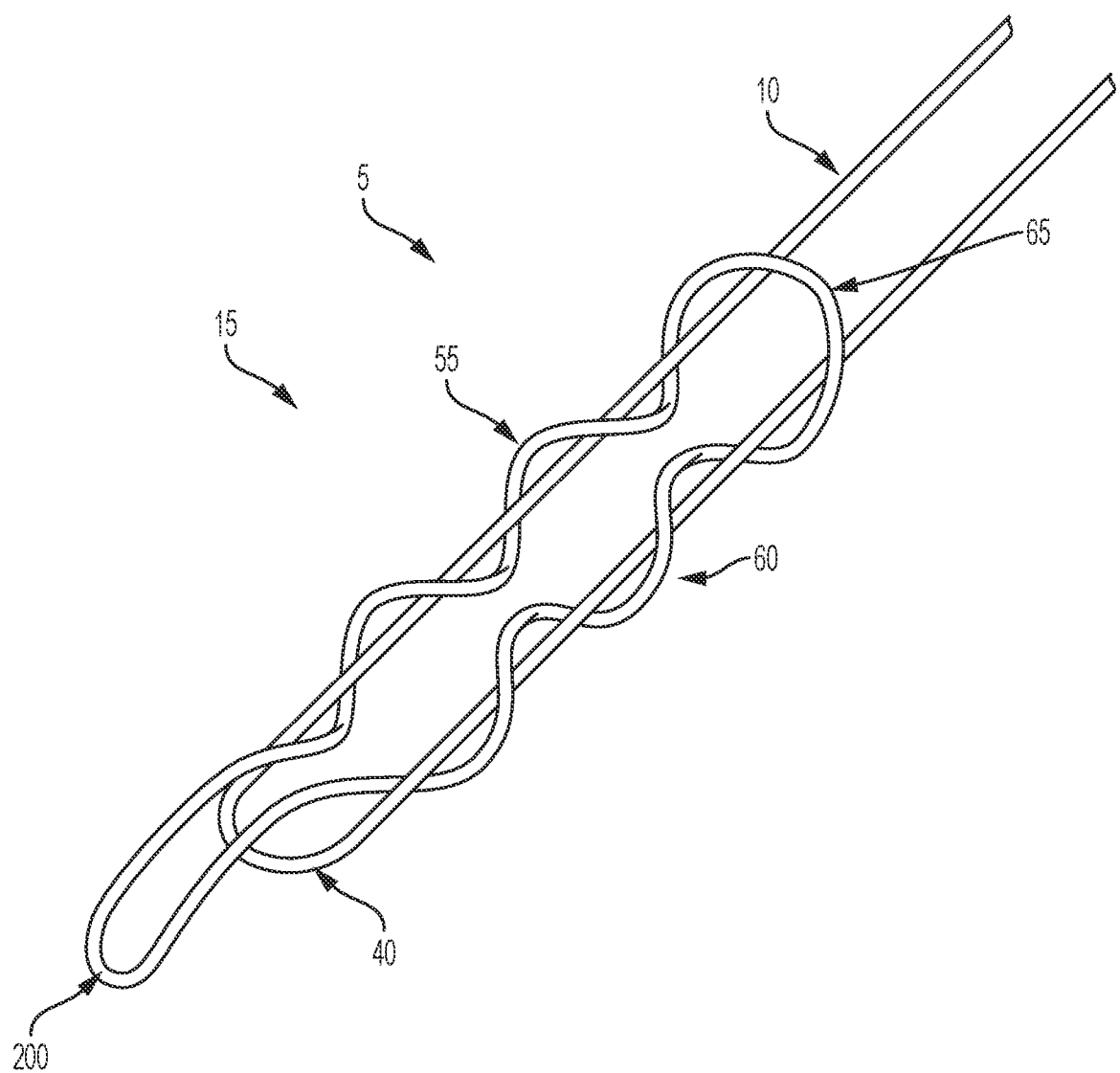

Additional configurations are shown in FIGS. 52-54. More particularly, the suture construct shown in FIG. 52 is substantially the same as the suture assembly shown in FIG. 2, except that the first and second ends 45, 50 of second suture 15 are joined together at 190 such that the second suture forms a substantially closed loop. Various means may be used to join together the first and second ends of second suture 15, e.g., simply tying the ends into a knot (not shown); gluing or thermal welding, the use of a mechanical means or device such as a pledget that joins the ends together (not shown), etc. Additionally, one end of second suture 15 can be inserted through the body of the other end so as to form a single strand 195 (FIG. 53). Furthermore, second suture 15 can be manufactured as a closed loop, i.e., so as to provide a distal bridge 200 (FIG. 54).

The constructions shown in FIGS. 52-54 can work adequately in some situations, e.g., where a larger bone hole size is acceptable and lower holding strengths can be tolerated. However, it must be emphasized that the suture assemblies shown in FIGS. 52-54 are not equivalent to the suture assembly shown in FIGS. 1-6 in either form or function. More particularly, with the suture assemblies shown in FIGS. 52-54, second suture 15 effectively forms a substantially closed loop, whereas with the suture assembly of FIGS. 1-6, the second suture 15 provides two free ends. The provision of two free ends with the suture assembly of FIGS. 1-6 is a significant advantage over the suture assemblies shown in FIGS. 52-54, inasmuch as it permits the suture assembly to self-accommodate within the insertion tube, thereby permitting substantially better compression of the suture assembly within the insertion tube. Again, this is significant, since better compression of the suture assembly within the insertion tube permits the use of a smaller bone hole, a smaller insertion tube and provides significantly better binding to the bone.

Using the Novel Suture Assembly to Suspend a Graft Ligament in a Bone Tunnel

As noted above, in some circumstances it may be desirable to attach a graft ligament (e.g., a graft anterior cruciate ligament, also known as an ACL) to bone (e.g., the femur) by fixing a portion of the graft ligament in a bone tunnel formed in the bone. As will hereinafter be discussed, novel suture assembly 5 can be used for this purpose. For purposes of clarity of description, novel suture assembly 5 will hereinafter be discussed in the context of an ACL reconstruction, however, it should be appreciated that novel suture assembly 5 may also be used for other forms of ligament reconstruction where a portion of the graft ligament must be fixed in a bone tunnel formed in the bone.

Figure 55:
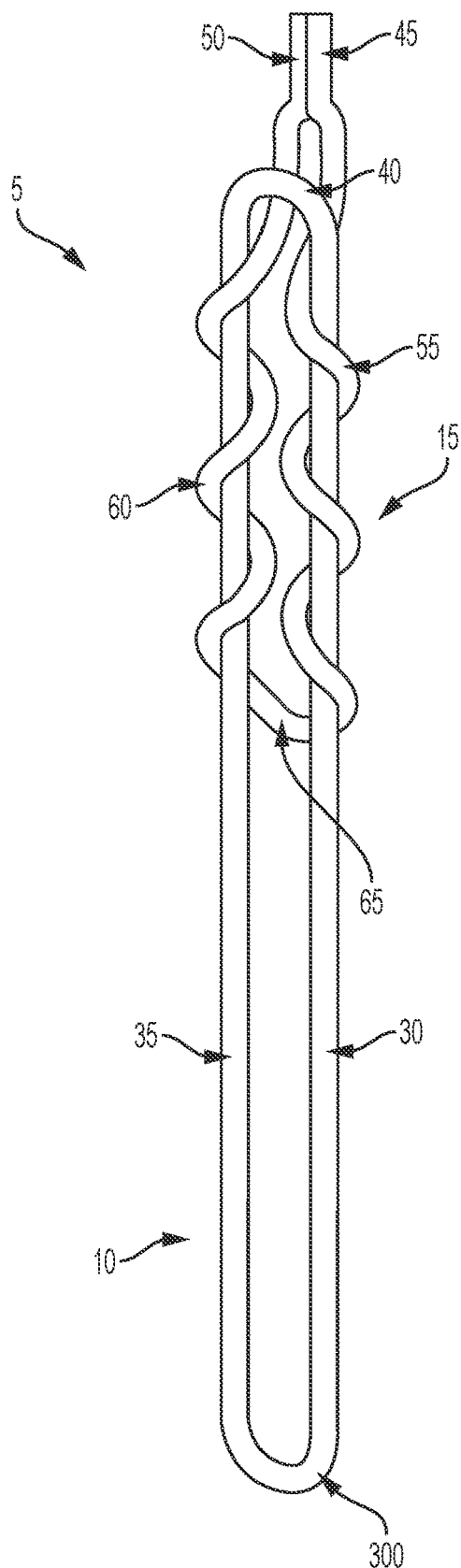
FIG. 55 is a schematic view showing another form of the novel suture assembly of the present invention.

As noted previously, and looking now at FIG. 55, novel suture assembly 5 generally comprises a first suture 10 and a second suture 15, wherein second suture 15 is wrapped around first suture 10 by (i) folding second suture 15 back on itself so as to provide first arm 55 and second arm 60, with first arm 55 being connected to second arm 60 via a bridge 65; (ii) positioning bridge 65 of second suture 15 across first arm 30 and second arm 35 of first suture 10, with bridge 65 of second suture 15 being spaced from bridge 40 of first suture 10; and (iii) wrapping first arm 55 of second suture 15 around first arm 30 of first suture 10, and wrapping second arm 60 of second suture 15 around second arm 35 of first suture 10, with first arm 55 of second suture 15 and second arm 60 of second suture 15 being wrapped in opposite directions, in the manner previously described and as shown in FIG. 55.

In this form of the invention, first arm 30 and second arm 35 of first suture 10 are also joined to one another at a bridge 300, such that first suture 10 forms a closed loop.

Figure 56:
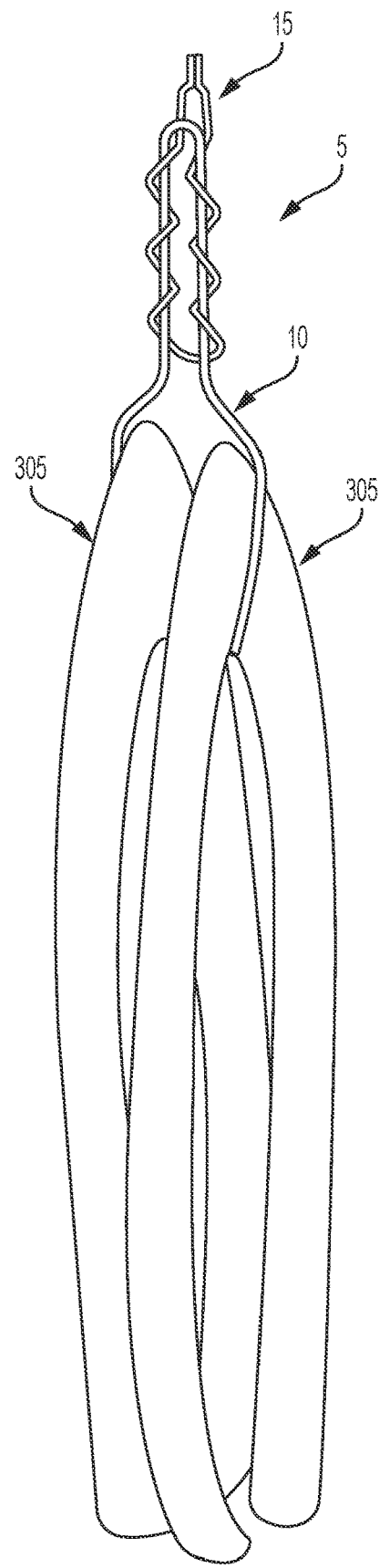
FIG. 56 is a schematic view showing the novel suture assembly of FIG. 55 supporting a plurality of graft ligaments.

Furthermore, in this form of the invention, and looking now at FIG. 56, first suture 10 is sized so that one or more graft ligaments 305 may be looped through the closed loop of first suture 10, in order that novel suture assembly 5 may be used to support the one or more graft ligaments 305 within a bone tunnel, as will hereinafter be discussed. For purposes of illustration but not limitation, the present invention will hereinafter be discussed in the context of supporting two graft ligaments 305 within a bone tunnel, wherein each of the graft ligaments comprises a pair of ligament strands, such that four ligament strands are supported within a bone tunnel.

Figure 57:
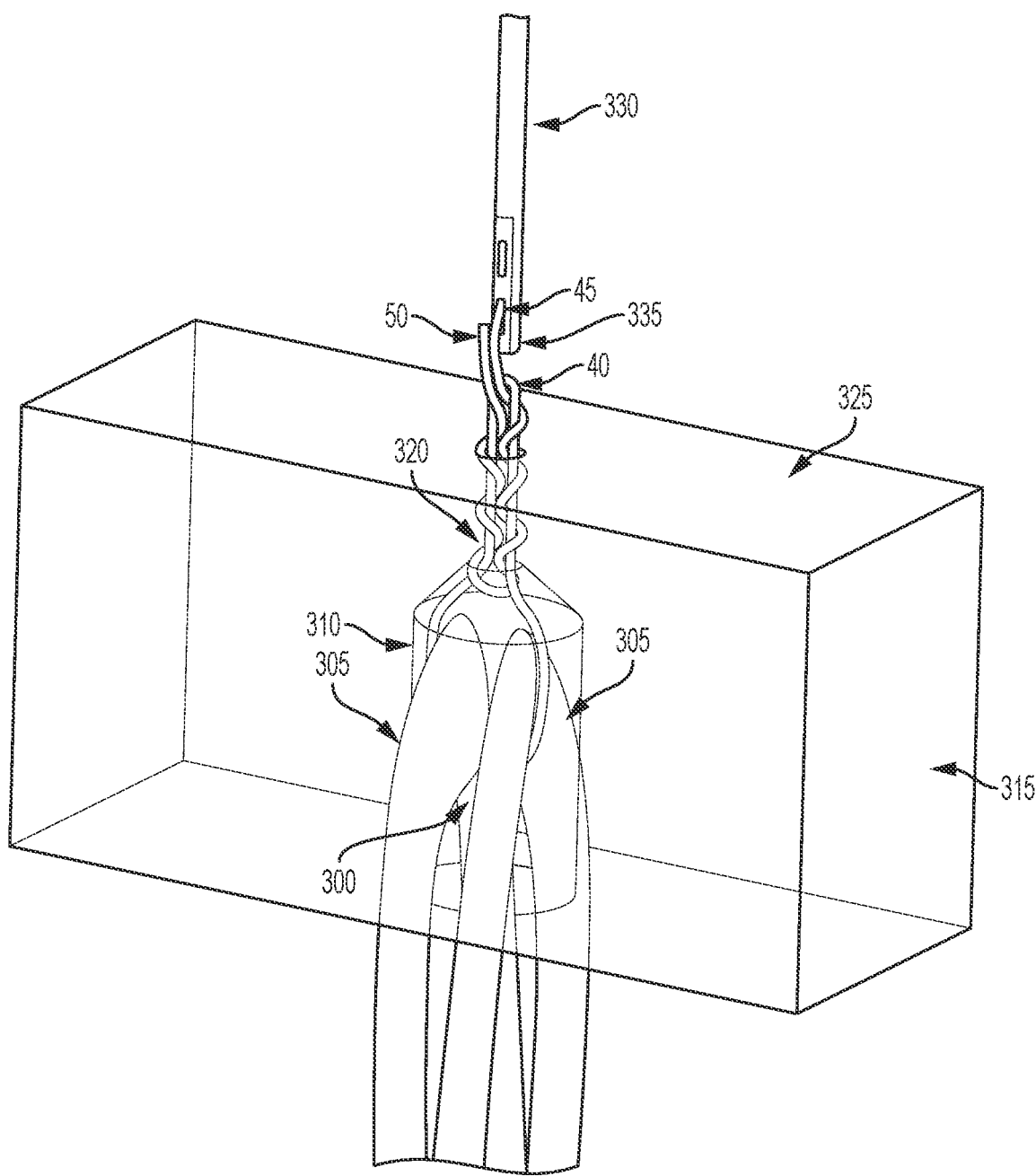

More particularly, in this form of the invention, and looking now at FIG. 57, a bone tunnel (i.e., hole) 310 is formed within the bone 315 which is to receive the graft ligament. In the case of an ACL reconstruction, bone 315 typically comprises the femur, and bone tunnel 310 typically comprises a bone tunnel opening on the base of the femur and extending upward into the femur. Bone tunnel 310 preferably has a diameter which is substantially the same as, or even undersized slightly relative to, the combined diameter of the two graft ligaments 305 which are to be attached to bone 315. In other words, bone tunnel 310 preferably has a diameter which is substantially the same as (or slightly smaller than) the combined diameter of the four ligament strands which make up the two graft ligaments 305. In any case, bone tunnel 310 has a diameter which is sufficient to accommodate the two graft ligaments 305 without requiring the application of excessive force to move the two graft ligaments within the bone tunnel.

At the base of bone tunnel 310, a second bone tunnel 320 (of lesser diameter than that of bone tunnel 310) is formed. Bone tunnel 320 extends upward from bone tunnel 310 and opens on the cortical bone surface 325 of bone 315. In the case of an ACL reconstruction, where bone 315 typically comprises the femur and bone tunnel 310 typically comprises a bone tunnel opening on the base of the femur and extending upward into the femur, second bone tunnel 320 opens on the anterior surface of the femur, just above the knee joint. In essence, the small diameter bone tunnel 320 and the large diameter bone tunnel 310 form a bore/counterbore construct.

If desired, bone tunnel 320 may be formed in bone 315 before bone tunnel 310 is formed in bone 315, e.g., bone tunnel 320 may be formed by passing a guidewire through the bone, and then bone tunnel 310 may be formed by passing a cannulated drill over the guidewire.

Graft ligaments 305 are looped through the closed loop of first suture 10, and second suture 15 is attached to a passing pin 330, e.g., by attaching first end 45 and second end 50 of second suture 15 to the proximal end 335 of passing pin 330. This is done while novel suture assembly 5 is in its aforementioned longitudinally-expanded, radially-contracted first configuration. Then, with novel suture assembly 5 remaining in its aforementioned longitudinally-expanded, radially-contracted first configuration, passing pin 330 is used to pull novel suture assembly along bone tunnel 310 and bone tunnel 320, until bridge 65 of second suture 15 emerges on the distal side of cortical bone surface 325. At this point, bridge 40 of first suture 10 will also reside on the distal side of cortical bone surface 325, with the remainder of first suture 10 extending proximally along bone tunnel 320 and bone tunnel 310, and with graft ligaments 305 extending proximally along bone tunnel 310.

Figure 58:
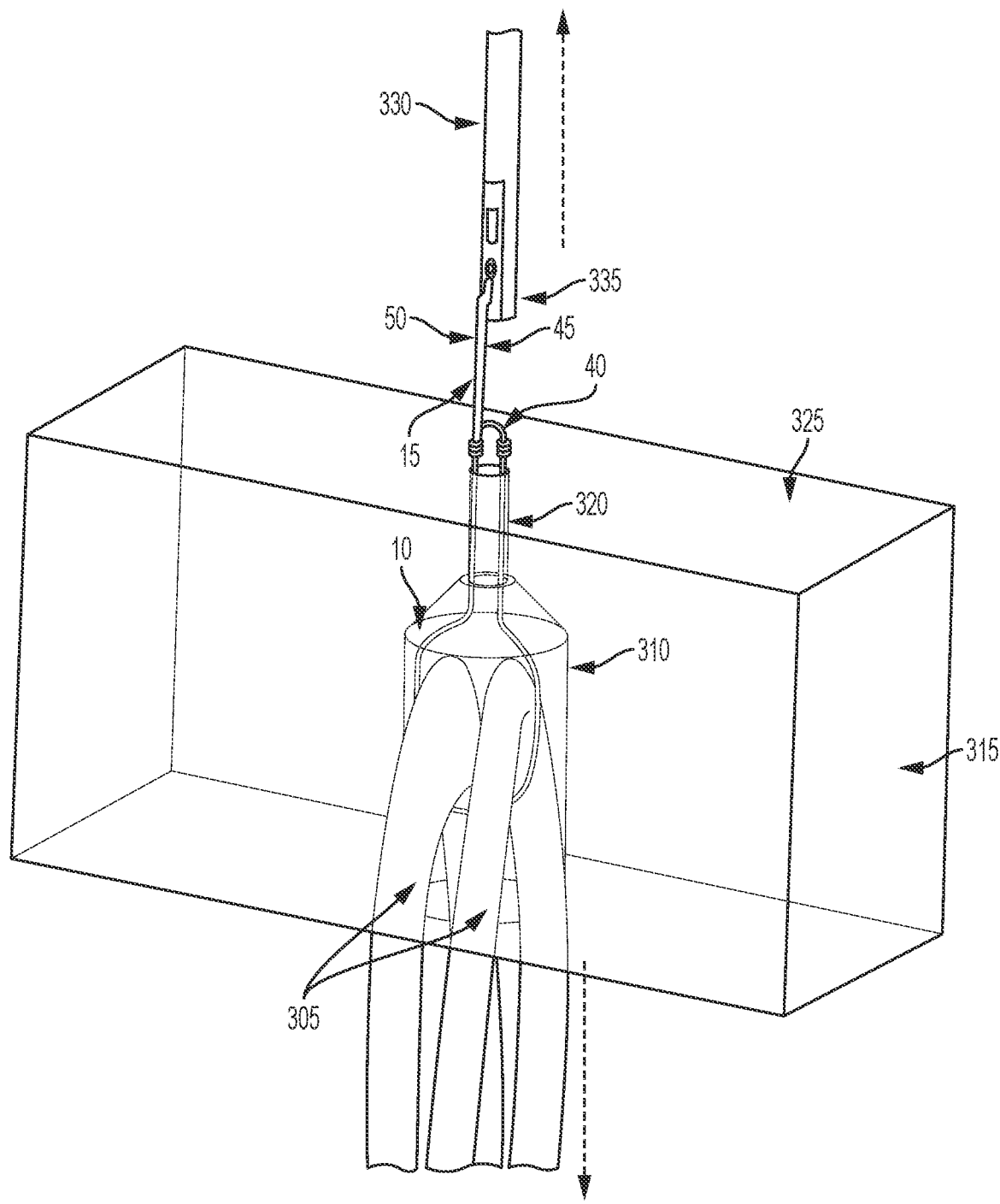

Next, graft ligaments 305 are tensioned proximally while first end 45 and second end 50 of second suture 15 are held taut outside the bone, thereby transforming novel suture assembly 5 from its longitudinally-expanded, radially-contracted first configuration (FIG. 57) into its longitudinally-contracted, radially-expanded second configuration (FIG. 58). This second configuration has a larger cross-sectional area than the first configuration and, significantly, a larger cross-sectional area than the smaller diameter bone tunnel 320, thereby providing a structure which is too large to be pulled back into the smaller diameter bone tunnel. Thus, novel suture assembly 5 effectively provides an enlarged structure on the distal side of bone 315 which bears against cortical bone surface 325 and supports the load of graft ligaments 305 carried by the closed loop of first suture 10.

Thereafter, passing pin 330 is released from the novel suture assembly 5, e.g., by cutting first end 45 and second end 50 of second suture 15, and the proximal ends of graft ligaments 305 may be made fast in ways well known in the art so as to complete the ligament reconstruction procedure. By way of example but not limitation, the proximal ends of graft ligaments 305 may be made fast in a bone tunnel formed in the adjacent tibia (not shown).

Thus it will be seen that novel suture assembly 5 can be used to provide a suspension-type fixation device for ligament repair.

Significantly, using novel suture assembly 5 to provide suspension-type fixation for ligament repair is highly advantageous, e.g., it allows bone/soft tissue ingrowth about the entire circumference of the bone hole, it is fast and easy to effect, and it eliminates certain deployment complications which may be encountered with prior art graft ligament fixation devices (e.g., difficulty in deploying a button on the far side of the bone). Furthermore, suture assembly 5 can be formed out of absorbable suture, enabling the suture assembly to be eliminated from the surgical site after bone/soft tissue ingrowth is complete.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A suture assembly comprising:
    a suture anchor comprising:
        a first suture having a generally U-shaped configuration comprising a first arm, a second arm and a bridge connecting the first arm to the second arm;
        a second solid and cylindrically shaped suture comprising a first arm, a second arm and a bridge connecting the first arm to the second arm, and forming a plurality of holes, wherein at least two of the plurality of holes is formed by the first arm of the second suture through which the first arm of the first suture is passed and through which a first central longitudinal axis extends, and at least two of the plurality of holes is formed by the second arm of the second suture through which the second arm of the first suture is passed and through which a second central longitudinal axis extends, wherein the second central longitudinal axis is a different axis from the first central longitudinal axis;
        the second suture being capable of sliding along the first suture from a first configuration to a second configuration.

2. The suture assembly according to claim 1, wherein the first arm of the second suture terminates in a first end, the second arm of the second suture terminates in a second end, and further wherein the first and second ends are free relative to one another.

3. The suture assembly according to claim 1, wherein the first and second arms of the second suture are connected to one another so as to form a loop.

4. The suture assembly according to claim 1, wherein the first suture comprises woven suture.

5. The suture assembly according to claim 1, wherein the second suture comprises woven suture.

6. The suture assembly according to claim 1, wherein the first suture comprises a hollow tubular structure.

7. The suture assembly according to claim 1, further comprising an inserter assembly for deploying the suture anchor in an anatomical structure, the inserter assembly comprising:
    an insertion tube for carrying at least a portion of the suture assembly within the insertion tube when the second suture is in its first configuration; and
    a push rod for engaging the suture assembly when the suture assembly is disposed within the insertion tube.

* * * * *